US012702650B2

(12) # United States Patent
Zou et al.

(10) Patent No.: US 12,702,650 B2
(45) Date of Patent: Aug. 11, 2026

(54) METHODS AND COMPOSITIONS FOR TREATING SMITH-MAGENIS SYNDROME

(71) Applicant: The Regents of the University of California, Oakland, CA (US)

(72) Inventors: Yimin Zou, La Jolla, CA (US); John Scott, La Jolla, CA (US); Sonal Thakar, La Jolla, CA (US)

(73) Assignee: The Regents of the University of California, Oakland, CA (US)

(*) Notice: Subject to any disclaimer, the term of this patent is extended or adjusted under 35 U.S.C. 154(b) by 1214 days.

(21) Appl. No.: 17/622,027

(22) PCT Filed: Jun. 26, 2020

(86) PCT No.: PCT/US2020/039898

§ 371 (c)(1),
(2) Date: Dec. 22, 2021

(87) PCT Pub. No.: WO2020/264350

PCT Pub. Date: Dec. 30, 2020

(65) Prior Publication Data

US 2022/0280452 A1 Sep. 8, 2022

Related U.S. Application Data

(60) Provisional application No. 62/867,068, filed on Jun. 26, 2019.

(51) Int. Cl.

| | |
|---|---|
| ***A61K 31/135*** | (2006.01) |
| ***A61K 31/13*** | (2006.01) |
| ***A61K 31/165*** | (2006.01) |
| ***A61K 31/403*** | (2006.01) |
| ***A61K 31/439*** | (2006.01) |
| ***A61K 31/4453*** | (2006.01) |
| ***A61K 31/451*** | (2006.01) |
| ***A61K 31/485*** | (2006.01) |
| ***A61K 33/00*** | (2006.01) |
| ***A61K 45/06*** | (2006.01) |
| ***A61P 25/00*** | (2006.01) |
| ***A61P 25/04*** | (2006.01) |
| ***A61P 25/18*** | (2006.01) |
| ***A61P 25/28*** | (2006.01) |
| ***A61P 43/00*** | (2006.01) |
| *G01N 33/50* | (2006.01) |

(52) U.S. Cl.

CPC ............ *A61K 31/135* (2013.01); *A61K 31/13* (2013.01); *A61K 31/439* (2013.01); *A61K 31/451* (2013.01); *A61K 31/485* (2013.01); *A61K 33/00* (2013.01); *A61K 45/06* (2013.01); *A61P 25/00* (2018.01)

(58) Field of Classification Search

CPC .... A61K 31/135; A61K 31/13; A61K 31/439; A61K 31/451; A61K 31/485; A61K 33/00; A61K 45/06; A61K 31/165; A61K 31/403; A61K 31/4453; A61P 25/00; A61P 25/04; A61P 25/18; A61P 25/28; A61P 43/00

See application file for complete search history.

(56) References Cited

U.S. PATENT DOCUMENTS

| | | | |
|---|---|---|---|
| 4,994,467 | A | 2/1991 | Zimmerman |
| 2009/0048348 | A1 | 2/2009 | Chez |
| 2011/0065645 | A1 | 3/2011 | Zou |
| 2015/0335702 | A1 | 11/2015 | Atwood et al. |

FOREIGN PATENT DOCUMENTS

| | | | |
|---|---|---|---|
| WO | WO-95/21612 | A2 | 8/1995 |
| WO | WO-2007/029063 | A2 | 3/2007 |

OTHER PUBLICATIONS

Andrade C. Intranasal drug delivery in neuropsychiatry: focus on intranasal ketamine for refractory depression. J Clin Psychiatry. May 2015;76(5):e628-31. doi: 10.4088/JCP.15f10026. PMID: 26035196. (Year: 2015).*

Liu et al. Developmental protein kinase C hyper-activation results in microcephaly and behavioral abnormalities in zebrafish. Transl Psychiatry. Oct. 23, 2018;8(1):232. doi: 10.1038/s41398-018-0285-5. PMID: 30352990; (Year: 2018).*

Wang R, Reddy PH. Role of Glutamate and NMDA Receptors in Alzheimer's Disease. J Alzheimers Dis. 2017;57(4):1041-1048. doi: 10.3233/JAD-160763. PMID: 27662322; PMCID: PMC5791143. (Year: 2017).*

Sharma A, Couture J. A review of the pathophysiology, etiology, and treatment of attention-deficit hyperactivity disorder (ADHD). Ann Pharmacother. Feb. 2014;48(2):209-25. doi: 10.1177/1060028013510699. Epub Nov. 1, 2013. PMID: 24259638. (Year: 2014).*

Elsea et al. Smith-Magenis syndrome, European Journal of Human Genetics, 2008, 16, 412-421 (Year: 2008).*

Extended European Search Report dated Jun. 30, 2023, for application No. 20831239.7, 10 pages.

Scott, John Thomas, "Novel signaling mechanisms of glutamatergic synapse formation and maintenance", UC San Diego Electronic Theses and Dissertations, Jun. 1, 2017, 106 pages.

Staples et al., "The cell polarity scaffold Lethal Giant Larvae regulates synapse morphology and function", Jan. 4, 2013, Journal of Cell Science, 126, pp. 1992-2003.

International Search Report and Written Opinion dated Sep. 30, 2020, from application No. PCT/US2020/039898.

(Continued)

*Primary Examiner* — Bruck Kifle
*Assistant Examiner* — Kevin S Martin
(74) *Attorney, Agent, or Firm* — Foley & Lardner LLP

(57) ABSTRACT

The present invention is based on the finding that subanesthetic doses of N-methyl-D-aspartate (NMDA) receptor antagonists alleviate social interaction deficits associated with behavioral disorders, such as Smith-Magenis Syndrome (SMS). The invention therefore provides methods and compositions for treating SMS. Also provided are methods of selecting NMDA receptor agonists useful in alleviating social interaction deficits associated with such behavioral disorders.

5 Claims, 24 Drawing Sheets

Specification includes a Sequence Listing.

(56) References Cited

OTHER PUBLICATIONS

Scott, et al. "Apical-Basal Polarity Signaling Components, Lgl1 and aPKCs, Control Glutamatergic Synapse Number and Function," iScience, Oct. 25, 2019, vol. 20, pp. 25-41.
Scott, J. "Novel signaling mechanisms of glutamatergic synapse formation and maintenance," Thesis, University of California, San Diego, Jun. 1, 2017, pp. 1-106.
Antunes et al., "The novel object recognition memory: neurobiology, test procedure, and its modifications," Cogn Process, 2012, vol. 13, pp. 93-110.
Berkel et al., "Mutations in the SHANK2 synaptic scaffolding gene in autism spectrum disorder and mental retardation," Nature Genetics, 2010, vol. 42, pp. 489-491.
Betschinger et al., "The Par complex directs asymmetric cell division by phosphorylating the cytoskeletal protein," Lgl. Nature, 2003, vol. 422, pp. 326-330.
Bochner et al., "Blocking PirB up-regulates spines and functional synapses to unlock visual cortical plasticity and facilitate recovery from amblyopia," Sci Transl Med, 2014, vol. 6, 258ra140.
Calfa et al., "HDAC activity is required for BDNF to increase quantal neurotransmitter release and dendritic spine density in CA1 pyramidal neurons," Hippocampus, 2012, vol. 22, pp. 1493-1500.
Chen et al., "Homologous recombination of a flanking repeat gene cluster is a mechanism for a common contiguous gene deletion syndrome," Nature Genetics, 1997, vol. 17, pp. 154-163.
Chen et al., The Smith-Magenis Syndrome [del(17)p11.2]: Clinical Review and Molecular Advances., Mental Retardation and Developmental Disabilities Research Reviews, 1996, vol. 2, pp. 122-129.
Cohen et al., "The structure of postsynaptic densities isolated from dog cerebral cortex: I. overall morphology and protein composition," Journal of Cell Biology, 1977, vol. 74, pp. 181-203.
Collingridge et al., "Excitatory amino acids in synaptic transmission in the Schaffer collateral-commissural pathway of the rat hippocampus," Journal of Physiology, 1983, vol. 334, pp. 33-46.
Dominquez et al., "The Imaginary Part of Coherency in Autism: Differences in Cortical Functional Connectivity in Preschool Children," PLOS One, 2013, vol. 8, pp. 1-13.
Dumitriu et al, "High-throughput, detailed, cell-specific neuroanatomy of dendritic spines using microinjection and confocal microscopy," Nature Protocols, 2011, vol. 6, 1391-1411.
Durand et al., "Mutations in the gene encoding the synaptic scaffolding protein SHANK3 are associated with autism spectrum disorders," Nature Genetics, 2007, vol. 39, pp. 25-27.
Dykens et al., Distinctiveness and correlates of maladaptive behaviour in children and adolescents with Smith-Magenis syndrome. Journal of Intellectual Disability Research, 1998, vol. 42, pp. 481-489.
Ebnet et al., "The junctional adhesion molecule (JAM) family members JAM-2 and JAM-3 associate with the cell polarity protein PAR-3: a possible role for JAMs in endothelial cell polarity," Journal of Cell Science, 2003, vol. 116, pp. 3879-3891.
Edelman et al., "Gender, genotype, and phenotype differences in Smith-Magenis syndrome: a meta-analysis of 105 cases," 2007, Clin Genet, vol. 71, pp. 540-550.
Ehrlich et al., "Postsynaptic Density 95 controls AMPA Receptor Incorporation during Long-Term Potentiation and Experience-Driven Synaptic Plasticity," J Neurosci, 2004, vol. 24, pp. 916-927.
Georgiou et al., "Cdc42, Par6, and aPKC Regulate Arp2/3-Mediated Endocytosis to Control Local Adherens Junction Stability," Current Biology, 2008, pp. 1631-1638.
Girirajan et al., "Genotype-phenotype correlation in Smith-Magenis syndrome: Evidence that multiple genes in 17p11.2 contribute to the clinical spectrum," Genetics in Medicine, 2006, vol. 8, No. 7, pp. 417-427.
Greenberg et al., "Multi-Disciplinary Clinical Study of Smith-Magenis Syndrome (Deletion 7p11.2)," American Journal of Medical Genetics, 1996, vol. 32, pp. 247-254.
Gropman et al., "New developments in Smith-Magenis syndrome (del 17p11.2)," Current Opinion in Neurology, 2007, vol. 20, pp. 125-134.
Harris et al., "Three-Dimensional Structure of Dendritic Spines and Synapses in Rat Hippocampus (CA1) at Postnatal Day 15 and Adult Ages: Implications for the Maturation of Synaptic Physiology and Long-Term Potentiation," The Journal of Neuroscience, 1992, vol. 12, No. 7, pp. 2685-2705.
Heimer-McGinn et al., "Efficient Inducible Pan-Neuronal Cre-Mediated Recombination in SLICK-H Transgenic Mice," Genesis, 2011, vol. 49, pp. 942-949.
Huang et al., "Molecular and Neural Functions of Rai1, the Causal Gene for Smith-Magenis Syndrome," Neuron, 2016, vol. 92, pp. 1-15.
Hung et al., "Smaller Dendritic Spines, Weaker Synaptic Transmission, but Enhanced Spatial Learning in Mice Lacking Shank1," The Journal of Neuroscience, 2008, vol. 28, pp. 1697-1708.
Irifune et al., "Ketamine-Induced Hyperlocomotion Associated With Alteration of Presynaptic Components of Dopamine Neurons in the Nucleus Accumbens of Mice," Pharmacology Biochemistry and Behavior, 1991, vol. 40, pp. 399-407.
Jeyifous et al., "SAP97 and CASK mediate sorting of NMDA receptors through a previously unknown secretory pathway," Nature Neuroscience, 2009, vol. 12, No. 8, pp. 1011-1021.
Karner et al., "Apical-basal polarity, Wnt signaling and vertebrate organogenesis," Seminars in Cell & Developmental Biology, 2006, vol. 17, pp. 214-222.
Keown et al., "Local Functional Overconnectivity in Posterior Brain Regions Is Associated with Symptom Severity in Autism Spectrum Disorders," Cell Reports, 2013, vol. 5, pp. 567-572.
Kim et al., "PDZ Domain Proteins of Synapses," Nature Reviews Neuroscience, 2004, vol. 5, pp. 771-781.
Kim et al., "Surface Trafficking of Sodium Channels in Cells and in Hippocampal Slices," Methods Mol Biol., 2011, vol. 793, pp. 351-361.
Koyama et al., "The human homologue of the murine Liglh gene (LLGL) maps within the Smith-Magenis syndrome region in 17p11. 2," Cytogenetic and Genome Research, 1996, vol. 72, pp. 72-82.
Laje et al., "Autism Spectrum Features in Smith-Magenis Syndrome," Am J Med Genet C Semin Med Genet, 2010, vol. 154, pp. 456-462.
Leonard et al., "SAP97 Is Associated with the a-Amino-3-hydroxy-5-methylisoxazole-4-propionic Acid Receptor GluR1 Subunit," Journal of Biological Chemistry, 1998, vol. 273, pp. 19518-19524.
Li et al., "Decreases in nestlet shredding of mice by serotonin uptake inhibitors: Comparison with marble burying," Life Sciences, 2006, Vo. 78, pp. 1933-1939.
Li et al., "Some Assembly Required: The Development of Neuronal Synapses," Nature Reviews, Molecular Cell Biology, 2003, vol. 4, pp. 833-841.
Lin et al., "Postsynaptic Density Protein-95 Regulates NMDA Channel Gating and Surface Expression," The Journal of Neuroscience, 2004, vol. 24, No. 45, pp. 10138-10148.
Macara et al., "Parsing the Polarity Code," Nature Reviews Molecular Cell Biology, 2004, vol. 5, pp. 220-231.
Martin et al., "Adaptive and Maladaptive Behavior in Children with Smith-Magenis Syndrome," Journal of Autism and Developmental Disorders, 2006, vol. 36, pp. 541-552.
Meffert et al., NF-kappa B functions in synaptic signaling and behavior, Nature Neuroscience, 2003, vol. 6, No. 10, pp. 1072-1078.
Mei et al., "Adult restoration of Shank3 expression rescues selective autistic-like phenotypes," Nature, 2016, vol. 530, pp. 481-484.
Monaghan et al., "The Excitatory Amino Acid Receptors: Their Classes, Pharmacology, and Distinct Properties In the Function of the Central Nervous System," Annual Review of Pharmacology and Toxicology, 1989, vol. 29, pp. 365-402.
Muller et al., "SAP102, a Novel Postsynaptic Protein That Interacts with NMDA Receptor Complexes In Vivo," Neuron, 1996, vol. 17, pp. 255-265.
Patel et al., An open-source toolbox for automated phenotyping of mice in behavioral tasks, Frontiers in Behavioral Neuroscience, 2014, vol. 8, pp. 1-16.
Peca et al., "Shank3 mutant mice display autistic-like behaviours and striatal dysfunction," Nature, 2011, vol. 472, pp. 437-442.
Phelan et al., "22q13 deletion syndrome," Am J Med Genet, 2001, vol. 101, pp. 91-99.

(56) References Cited

OTHER PUBLICATIONS

Potocki et al., "Variability in clinical phenotype despite common chromosomal deletion in Smith-Magenis syndrome [del(17)(p11.2p11.2)]," Genetics in Medicine, 2003, vol. 5, No. 6, pp. 430-434.
Prybylowski et al., "The Synaptic Localization of NR2B-Containing NMDA Receptors Is Controlled by Interactions with PDZ Proteins and AP-2," Neuron, 2005, vol. 47, pp. 845-857.
Sans et al., "A Developmental Change in NMDA Receptor-Associated Proteins at Hippocampal Synapses," The Journal of Neuroscience, 2000, vol. 20, No. 3, pp. 1260-1271.
Sato et al., "SHANK1 Deletions in Males with Autism Spectrum Disorder," The American Journal of Human Genetics, 2012, vol. 90, pp. 879-887.
Schmeisser et al., "Autistic-like behaviours and hyperactivity in mice lacking ProSAP1/Shank2," Nature, 2012, vol. 486, pp. 256-260.
Smith et al., "Interstitial Deletion of (17)(p11.2p11.2) in Nine Patients," American Journal of Medical Genetics, 1986, vol. 24, pp. 393-414.
Soorya et al., "Prospective investigation of autism and genotype-phenotype correlations in 22q13 deletion syndrome and SHANK3 deficiency," Molec Autism, 2013, vol. 4, No. 18, pp. 1-18.
Sudhof et al., "The Presynaptic Active Zone," Neuron, 2012, vol. 75, pp. 11-25.
Supekar, et al., "Brain Hyperconnectivity in Children with Autism and its Links to Social Deficits," Cell Reports, 2013, vol. 5, pp. 738-747.
Tang et al., "Loss of mTOR-Dependent Macroautophagy Causes Autistic-like Synaptic Pruning Deficits," Neuron, 2014, vol. 83, pp. 1131-1143.
Tao et al., "Impaired NMDA Receptor-Mediated Postsynaptic Function and Blunted NMDA Receptor-Dependent Persistent Pain in Mice Lacking Postsynaptic Density-93 Protein," The Journal of Neuroscience, 2003, Vo. 23, No. 17, pp. 6703-6712.
Thakar et al., "Evidence for opposing roles of Celsr3 and Vangl2 in glutamatergic synapse formation," PNAS, 2017, pp. E610-E618.
Vlangos et al., "Refinement of the Smith-Magenis syndrome critical region to 950 kb and assessment of 17p11.2 deletions. Are all deletions created equally?" Molecular Genetics and Metabolism, 2003, vol. 79, pp. 134-141.
Vogel-Ciernia et al., "The neuron-specific chromatin regulatory subunit BAF53b is necessary for synaptic plasticity and memory," Nature Neuroscience, 2013, vol. 16, No. 5, pp. 552-563.
Wang et al., "Changes in Hippocampal Synapses and Learning-Memory Abilities in Age-Increasing Rats and Effects of Tetrahydroxystilbene Glucoside in Aged Rats," Neuroscience, 2007, vol. 149 pp. 739-746.
Watkins et al., "Excitatory Amino Acid Transmitters," Ann. Rev. Pharmacol. Toxicol., 1981, vol. 21, pp. 165-204.
Wessel et al., "A Method for the Quantitative Recovery of Protein in Dilute Solution in the Presence of Detergents and Lipids," Analytical Biochemistry, 1984, vol. 138, pp. 141-143.
Xiao et al., "Homer Regulates the Association of Group 1 Metabotropic Glutamate Receptors with Multivalent Complexes of Homer-Related, Synaptic Proteins," Neuron, 1998, vol. 21, pp. 707-716.
Yamanaka et al., "Lgl mediates apical domain disassembly by suppressing the PAR-3 ?? PKC-PAR-6 complex to orient apical membrane polarity," Journal of Cell Science, 2006, vol. 119, No. 10, pp. 2107-2118.
Yamanaka et al., "Mammalian Lgl Forms a Protein Complex with PAR-6 and aPKC Independently of PAR-3 to Regulate Epithelial Cell Polarity," Current Biology, 2003, vol. 13, pp. 734-743.
Yang et al., "Automated Three-Chambered Social Approach Task for Mice," Curr Protoc Neurosci, 2011, Ch. 8, Unit 8.26, pp. 1-23.
Young et al., "Single-neuron labeling with inducible Cre-mediated knockout in transgenic mice," Nature Neuroscience, 2008, vol. 11, No. 6, pp. 721-728.
Zarnescu et al., "Fragile X protein functions with Lgl and the PAR complex in flies and mice," Dev Cell, 2005, vol. 8, pp. 43-52.
Zhu et al., "Mechanistic basis of MAGUK-organized complexes in synaptic development and signalling," Nat Rev Neuroscience, 2016, vol. 17, pp. 209-223.
Klezovitch et al., "Loss of cell polarity causes severe brain dysplasia in Lgl1 knockout mice," Genes & Development, vol. 18, pp. 559-571, Dec. 15, 2003; revised version accepted Feb. 5, 2004.

* cited by examiner

Sample

Recognition

Distance (m)
150
100
50
0
Control dcKO

Thigmotaxis
1.0
0.5
0.0
•Control
•dcKO
0'-5' 5'-10'

Sample

Control
aPKC dcKO
Preference
1.0
0.5
0.0
-0.5
-1.0
Control dcKO

Recognition

Control
aPKC dcKO
*
Preference
1.0
0.5
0.0
-0.5
-1.0
Control dcKO

**
Cumulative Percent
100
50
0
0 200 400 600
PSD Length (nm)
Lgl1 +/+
Lgl1 +/-

****
Cumulative Percent
100
50
0
0 50 100 150
PSD Width (nm)

****
Cumulative Percent
100
50
0
0 10 20 30 40
Cleft (nm)

**
Nestlet Shredded
1.0
0.8
0.6
0.4
0.2
0.0
Lgl1 +/+ Lgl1 +/-

Recognition
Lgl1 +/+
Lgl1 +/-
*
Preference
1.0
0.5
0.0
-0.5
-1.0
Lgl1 +/+
Lgl1 +/-

2 weeks
Control
Lgl1 cKO
Proximal
synapses/100μm²
40
30
20
10
0
•Control
◦cKO
Spine Shaft 8 weeks
Control
Lgl1 cKO
synapses/100μm²
60
40
20
0
Spine Shaft Lgl1 +/+
Lgl1 -/-
MAP2 / PSD95 / vGlut1

Puncta/100um
● Lgl1 +/+
◆ Lgl1 -/-
**
vGlut1 PSD95 Colocalized

Decay Tau (ms) — Control cKO
Rise Tau (ms) — Control cKO
Max Slope (pA/ms) — Control cKO
Area (pA*ms) — Control cKO Decay Tau (ms) — Control cKO *
Rise Tau (ms) — Control cKO
Max Slope (pA/ms) — Control cKO
Area (pA*ms) — Control cKO synapses/100μm2
Control
dcKO
Spine
Shaft synapses/100μm2
***
Spine
Shaft synapses/100μm2
Control
tcKO
Spine
Shaft synapses/100μm2
Spine
Shaft Grooming (s)
Control
cKO Rearing
**
Control
cKO

METHODS AND COMPOSITIONS FOR TREATING SMITH-MAGENIS SYNDROME

CROSS-REFERENCE TO RELATED APPLICATIONS

This application is a U.S. National Stage Application under 35 U.S.C. § 371 of International Patent Application No. PCT/US2020/039898, filed on Jun. 26, 2020, which claims the benefit of priority under 35 U.S.C. § 119 (e) to U.S. Provisional Application No. 62/867,068, filed on Jun. 26, 2019, the contents of each of which are hereby incorporated by reference into the present application in their entireties.

GRANT INFORMATION

This invention was made with government support under MH099082 awarded by the National Institutes of Health. The government has certain rights in the invention.

SEQUENCE LISTING

The instant application contains a Sequence Listing which has been submitted electronically in ASCII format and is hereby incorporated by reference in its entirety Said ASCII copy, created on Dec. 22, 2021, is named 114198-7002 SL.txt and is 61 kilobytes in size.

BACKGROUND OF THE INVENTION

Field of Invention

The invention relates generally to behavioral disorders and more specifically to methods of treating such disorders with NMDA receptor antagonists.

Background Information

Glutamatergic synapses are the major class of excitatory synapses in the mammalian central nervous system and most projection neurons are glutamatergic neurons (Collingridge et al., 1983; Monaghan et al., 1989; Watkins and Evans, 1981). Normal development and plasticity of glutamatergic synapses are essential to behavioral functions, the disruption of which causes various disorders. A recent study showed that components of planar cell polarity (PCP) signaling pathway are key regulators of glutamatergic synapse formation (Thakar et al., 2017). Celsr3 is essential for glutamatergic synapse formation, whereas Vang12 negatively regulates glutamatergic synapse formation. Therefore, PCP signaling components can both positively and negatively regulate glutamatergic synapse numbers.

Lethal giant larvae (Lgl1) is a key component of the highly conserved apical-basal polarity signaling pathway, which polarizes epithelial cells and tissues along the apical and basolateral axis (Kamer et al., 2006). Lgl1 is frequently deleted in a Chromosome 17 p11.2 microdeletion disorder, called Smith-Magenis Syndrome (SMS). Smith-Magenis Syndrome (SMS) is a de novo genetic disorder arising very early in embryonic development through homologous recombination (Chen et al., 1997). A deletion interval of 3.5 Mb occurs in approximately 70% of patients (Gropman et al., 2007). Individuals with the deletion are frequently diagnosed with Autism Spectrum Disorders (ASDs), attention-deficit/hyperactivity disorder (ADHD), obsessive-comulsive disorder (OCD), or other behavioral disorders (Dykens et al., 1997; Dykens and Smith, 1998; Laje et al., 2010; Martin et al., 2006; Smith A C et al., 1998). Symptoms vary between individuals despite common deletions (Edelman et al., 2007; Potocki et al., 2003) and multiple genes likely contribute to the syndrome (Girirajan et al., 2006). Recent work has implicated Rai 1 in non-ASD symptoms of SMS (Huang et al., 2016). There are unmet needs for the better understanding of molecular mechanisms underlying Lgl1-mediated excitotoxic neurodegeneration and ensuing conditions and disease, as well as methods for the identification and designing of effective modulators for research and therapeutic uses based on the mechanisms. There are also unmet needs for the provisions of therapeutic methods and agents for preventing, managing and treating conditions and diseases associated with Lgl1-mediated excitotoxicity, such as neurodegenerative diseases resulting from loss of synapses. The present disclosure meets these needs.

SUMMARY OF THE INVENTION

Accordingly, the invention provides a method for reducing or preventing lethal giant larvae (Lgl1) induced increase in synapses in a population of neurons, comprising contacting the neurons with a subanesthetic amount of an N-methyl-D-aspartate (NMDA) receptor antagonist. In various embodiments, the NMDA receptor antagonist increases the AMPA/NMDA ratio in the neurons. In various embodiments, the NMDA receptor antagonist is selected from the group consisting of ketamine, memantine, dizocilpine (MK-801), dextromethorphan (DXM), phencyclidine (PCP), methoxetamine (MXE), nitrous oxide ($N_2$), and any combination thereof.

In various embodiments, the method may also include contacting the population of neurons with an atypical protein kinase c (aPKC) inhibitor. In various embodiments, the aPKC inhibitor is a small molecule compound, a nucleic acid molecule or polypeptide. In various embodiments, the aPKC inhibitor is an antibody or antigen binding fragment that binds to one or more of protein kinase c ζ (aPKCζ) and protein kinase c ι/λ (aPKCι/λ) isoforms. In various embodiments, the aPKC inhibitor reduces or inhibits expression of aPKCλ and aPKCι/λ in the neurons.

In various embodiments, the method may also include contacting the population of neurons with a Lgl1 agonist. In various embodiments, the Lgl1 agonist is a small molecule compound, a nucleic acid molecule or polypeptide that induces expression of Lgl1. In various embodiments, the Lgl1 agonist is a small molecule compound, a nucleic acid molecule or polypeptide that induces a signaling pathway that induces expression of Lgl1.

In various embodiments, the population of neurons is in a subject, and wherein the step of contacting is performed by administering NMDA receptor antagonist and/or the aPKC inhibitor and/or the Lgl1 agonist to the subject. In various embodiments, the population of neurons is in the brain of the subject. In various embodiments, the subject has or is at risk of developing a neurodegenerative disease or behavioral disorder, such as Smith-Magenis Syndrome (SMS), autism, or attention deficit hyperactivity disorder (ADHD). In various embodiments, the NMDA receptor antagonist alleviates social interaction deficits associated with the behavioral disorder.

In another aspect, the invention provides a method of managing, preventing, or treating a neurodegenerative disease or behavioral disorder in a subject, comprising administering to the subject a subanesthetic amount of an N-methyl-D-aspartate (NMDA) receptor antagonist. In various embodiments, the NMDA receptor antagonist increases the AMPA/NMDA ratio in the neurons. In various embodiments, the NMDA receptor antagonist is selected from the group consisting of ketamine, memantine, dizocilpine (MK-801), dextromethorphan (DXM), phencyclidine (PCP), methoxetamine (MXE), nitrous oxide ($N_2$), and any combination thereof.

In various embodiments, the method may also include administering to the subject an atypical protein kinase c (aPKC) inhibitor. In various embodiments, the aPKC inhibitor is a small molecule compound, a nucleic acid molecule or polypeptide. In various embodiments, the aPKC inhibitor is an antibody or antigen binding fragment that binds to one or more of protein kinase c ξ (aPKCξ) and protein kinase c ι/λ (aPKCι/λ) isoforms. In various embodiments, the aPKC inhibitor reduces or inhibits expression of aPKCξ and aPKCι/λ in the neurons.

In various embodiments, the method may also include administering to the subject a Lgl1 agonist. In various embodiments, the Lgl1 agonist is a small molecule compound, a nucleic acid molecule or polypeptide that induces expression of Lgl1. In various embodiments, the Lgl1 agonist is a small molecule compound, a nucleic acid molecule or polypeptide that induces a signaling pathway that induces expression of Lgl1.

In various embodiments, the number of synapses in a population of neurons in the subject is decreased. In various embodiments, the synapses are excitatory synapses. In various embodiments, the synapses are glutamatergic synapses. In various embodiments, the NMDA receptor antagonist alleviates social interaction deficits associated with the behavioral disorder. In various embodiments, the population of neurons comprises a cerebellar granule neuron, a dorsal root ganglion neuron, a cortical neuron, a sympathetic neuron, or a hippocampal neuron.

In another aspect, the invention provides a method of treating behavioral disorders, such as SMS, through modulation of Lgl1. In various embodiments, the method includes administering to a subject in need thereof an N-methyl-D-aspartate (NMDA) receptor antagonist, such as ketamine, at a subanesthetic dose, thereby alleviating social interaction deficits associated with the behavioral disorder. By blocking NMDA receptors, ketamine may mitigate abnormal activity patterns arising from over connectivity and increased NMDAR activity.

Exemplary NMDA receptor antagonists useful in the methods provided herein include, but are not limited to, as ketamine, memantine (NAMZARIC®), dizocilpine (MK-801), dextromethorphan (DXM), phencyclidine (PCP), methoxetamine (MXE), and nitrous oxide ($N_2$).

In yet another aspect, the invention provides a method of selecting a modulator of synapse formation or a modulator of synapse maintenance. In various embodiments, the method includes providing a population of neurons having a heterozygous or homozygous deletion, inactivation or knock-out of Lgl1; measuring a first level of the AMPA/NMDA ratio in the neurons; contacting a candidate agent with the population of neurons; measuring a second level of the AMPA/NMDA ratio in the neurons; and selecting the candidate agent as the modulator if the second level of association is different from the first level of association. In various embodiments, the candidate agent is a small-molecule compound, a nucleic acid, or a peptide. In various embodiments, the nucleic acid is a microRNA, siRNA or CRISPR-based gene editing construct. In various embodiments, the candidate agent is an antibody or antigen binding fragment thereof. In various embodiments, the method is performed in the presence of aPKC. In various embodiments, the population of the cells is in a non-human mammal, and wherein the step of contacting is performed by administering the candidate agent to the non-human mammal.

BRIEF DESCRIPTION OF THE DRAWINGS

FIG. 1A shows electron micrographs taken 150-200 μm (top) or 50 μm (bottom) ventral to the CA1 pyramidal neuron layer in the schaffer collateral region of P14 mice. Light arrows denote asymmetric synapses. Black arrows denote symmetric synapses. Scale bar: 500 nm. Quantification of synapse numbers corresponding to each region: N=6 control, 6 Lgl1 cKO animals. FIG. 1B shows electron micrographs taken 150-200 μm (top) or 50 μm (bottom) ventral to the CA1 pyramidal neuron layer in the schaffer collateral region of 8-week-old mice. Light arrows denote asymmetric synapses. Black arrows denote symmetric synapses. Quantification of synapse numbers corresponding to each region: N=5 control, 5 Lgl1 cKO animals. FIG. 1C shows representative traces of mEPSC recordings from acute slices from P13-P15 control and Lgl1 cKO mice. Quantification of mEPSC frequency and amplitude: n=22 control, 19 Lgl1 cKO neurons. FIG. 1D shows representative traces of mIPSC recordings from acute slices from P14 control and Lgl1 cKO mice. Quantification of mIPSC frequency and amplitude: n=20 control, 19 Lgl1 cKO neurons. FIG. 1E shows representative shows representative confocal images of oblique CA1 dendrites filled with Alexa Fluor 555 Hydrazide. Scale bar: 10 μm. FIG. 1F shows quantification of spine density and FIG. 1G shows distribution of spin morphology. FIG. 1H shows quantification of cumulative distributions of synapse ultrastructure measurements in P14 control and cKO animals: n=194 control, 174 Lgl1 cKO synapses. Quantification of cumulative distributions of synapse ultrastructure measurements in 8-week old control and cKO animals: n=194 control, 208 Lgl1 cKO synapses. FIG. 1I shows biochemical fractionation from wild-type P14 mice. P2, crude synaptosomal; SMF, synaptic membrane fraction; PSD, postsynaptic density. FIG. 1J shows representative traces of NMDAR currents and combined AMPAR/NMDAR currents from acute slices taken from P14 control and Lgl1 cKO mice following Lgl1 deletion at P7. Scale bar, 100 pA (vertical); 100 ms (horizontal). Quantification of the calculated ratio of AMPAR current to NMDAR current: n=13 control, 13 Lgl1 cKO neurons. *$p<0.05$; $p<0.01$; *$p<0.001$; ****$p<0.0001$.

FIG. 2A shows electron micrographs taken 150-200 mm (top) or 50 mm (bottom) ventral to the CA1 pyramidal neuron layer in the schaffer collateral region of P14 mice. Light arrows denote asymmetric synapses. Black arrows denote symmetric synapses. Scale bar, 500 nm. Quantification of synapse numbers corresponding to each region: N=8 control, 5 aPKC dcKO animals. FIG. 2B shows electron micrographs taken 150-200 mm (top) or 50 mm (bottom) ventral to the CA1 pyramidal neuron layer in the schaffer collateral region of 8-week-old mice. Light arrows denote asymmetric synapses. Black arrows denote symmetric synapses. Quantification of synapse numbers corresponding to each region: N=5 control, 8 aPKC dcKO animals. FIG. 2C shows quantification of cumulative distribution of synapse ultrastructure measurements in P14 control and cKO animals: n=194 control, 129 aPKC dcKO synapses. Quantification of cumulative distribution of synapse ultrastructure measurements in 8-week-old control and cKO animals: n=87 control, 168 aPKC dcKO synapses. FIG. 2D shows electron micrographs taken 150-200 mm (top) or 50 mm (bottom) ventral to the CA1 pyramidal neuron layer in the schaffer collateral region of P14 mice. Light arrows denote asymmetric synapses. Black arrows denote symmetric synapses. Scale bar, 500 nm. Quantification of synapse numbers corresponding to each region: N=7 control, 6 Lgl1:PKCι/λ: PKCλ tcKO animals. FIG. 2E shows electron micrographs taken 150-200 mm (top) or 50 mm (bottom) ventral to the CA1 pyramidal neuron layer in the schaffer collateral region of 8-week-old mice. Light arrows denote asymmetric synapses. Black arrows denote symmetric synapses. Quantification of synapse numbers corresponding to each region: N=8 control, 10 Lgl1:PKCι/λ: PKCξ tcKO animals. FIG. 2F shows levels of Vang12 and JAM-C proteins in P2 fractions by Western blots. FIG. 2G shows quantification of Vang12 and JAM-C protein levels in P2 fraction. N=5 for Vang12. N=4 for JAM-C. *p<0.05; p<0.01; *p<0.001; ****p<0.0001.

FIG. 3A shows electron micrographs of the schaffer collateral (SC) 150-200 mm ventral to the CA1 pyramidal cell layer of slices from 10-week-old control and Lgl1 cKO mice following deletion of Lgl1 beginning at 6 weeks of age. Light arrows denote asymmetric synapses. Scale bar, 500 nm. N=6 control, 8 Lgl1 cKO animals. FIG. 3N shows quantification of paired-pulse ratio from control and Lgl1 cKO animals deleted at 6 weeks. N=6 Lgl1 control, 6 Lgl1 cKO. *p<0.05; p<0.01; **p<0.0001.

FIG. 4A shows the results from Open field analysis following P7 deletion of Lgl1 showing representative trajectories (left) and heat maps (right) of control and Lgl1 cKO animals.

FIG. 5A shows the results of open-field analysis following P7 deletion of Lgl1 showing representative trajectories (left) and heatmaps (right) of control and aPKC dcKO animals. FIG. 5H shows quantification of time spent in and FIG. 51 shows preference for ROIs containing either the novel mouse or novel object. Positive value indicates preference for the novel mouse. N=35 control, 27 aPKC dcKO animals. *p<0.05; p<0.01.

N=21 control, 15 Lgl1:PKCι/λ: PKCξ tcKO animals.

FIG. 6A shows electron micrographs taken 150-200 μm (top) or 50 μm (bottom) ventral to the CA1 pyramidal neuron layer in the schaffer collateral region of 8-week-old control and $Lgl1^{+/-}$ mice. Light arrows denote asymmetric synapses. Black arrows denote symmetric synapses. Scale bar, 500 nm. Quantification of synapse numbers corresponding to each region: N=10 $Lgl1^{+/-}$, 7 $Lgl1^{+/-}$ animals. FIG. 6B shows quantification of cumulative distribution of synapse ultrastructure measurements in 8-week old $Lgl1^{+/+}$ and $Lgl1^{+/-}$ animals: n=265 $Lgl1^{+/+}$ synapses, 140 $Lgl1^{+/-}$ synapses. FIG. 6C shows Representative heatmaps from the 1-h extended-duration open-field test for $Lgl1^{+/+}$ and $Lgl1^{+/-}$ animals and quantification for distance traveled in the extended open-field test. N=30 $Lgl1^{+/+}$, 33 $Lgl1^{+/-}$. FIG. 6D shows quantification of nestlet-shredding activity. N=19 $Lgl1^{+/+}$, 30 $Lgl1^{+/-}$ animals. FIG. 6E shows representative heatmaps from the recognition test phase of the novel object recognition (NOR) test 24 h after the sample phase of the object. Quantification of object preference during the test phase 24 h after the sample phase. N=25 $Lgl1^{+/+}$, 32 $Lgl1^{+/-}$. FIG. 6F shows representative heatmaps during the social interaction phase of the social interaction (SI) test. White asterisk denotes location of the novel mouse. Quantification of interaction preference in the SI test. N=25 $Lgl1^{+/+}$, 33 $Lgl1^{+/-}$ animals. $^{*}p<0.05$; $^{}p<0.01$; $^{*}p<0.001$; $^{****}p<0.0001$.

FIG. 7A shows quantification of the occurrence of jerking/jumping, Straub tail, and clonic-tonic seizures in $Lgl1^{+/+}$ and $Lgl1^{+/-}$ animals following 50 mg/kg PTZ administration. Fisher's exact test. FIG. 7B shows quantification of the latency to the first observation of behaviors following 50 mg/kg PTZ administration. N=17 $Lgl1^{+/+}$, 15 $Lgl1^{+/-}$ animals. Mann-Whitney U statistic test. FIG. 7C shows representative heatmaps during the social interaction phase of the social interaction test following intraperitoneal injection with 50 mL saline, 30 mg/kg ketamine, 0.3 mg/kg MK-801, or 20 mg/kg memantine. White asterisk denotes location of the novel mouse. FIG. 7D shows quantification of time spent in social (S) or nonsocial (NS) regions of interest and FIG. 7E shows interaction preference of treated animals. N=(saline) 17 $Lgl1^{+/+}$, 19 $Lgl1^{+/-}$ animals; (ketamine) 14 $Lgl1^{+/+}$, 17 $Lgl1^{+/-}$ animals; (MK-801) 13 $Lgl1^{+/+}$, 14 $Lgl1^{+/-}$ animals; (memantine) 19 $Lgl1^{+/+}$, 17 $Lgl1^{+/-}$ animals. $^{*}p<0.05$; $^{}p<0.01$; $^{*}p<0.001$; $^{****}p<0.0001$.

FIG. 8A shows confocal images of brain slices from P14 mice injected with Tamoxifen at day P7 and P8 carrying SLICK-H shown by YFP (green) and ROSA26-tdTomato (red). Images show regions including the ventral hippocampal commissure and fimbria, dorsal hippocampus, and ventral hippocampus. Scale bar: 1 mm. FIG. 8B shows confocal images of brain slices of mice that were not injected with Tamoxifen, but carry the indicated SLICK and ROSA26-tdTomato. Scale bar: 1 mm. FIG. 8C shows images of brain regions expressing Thy-1 cre in SLICK-H and SLICK-A positive animals shown by YFP (green) and tdTomato (red). Scale bar: 100 μm. FIG. 8D shows electron micrographs taken 50 μm from the CA1 pyramidal neuron layer in the Schaffer Collateral Region of P14 mice. Light arrows denote asymmetric synapses. Quantification of asymmetric synapse number: N=6 control, 6 Lgl1 cKO animals. FIG. 8E shows electron micrographs taken 50 μm from the CA1 pyramidal neuron layer in the Schaffer Collateral Region of 8-week old mice. Arrows denote asymmetric synapses. Quantification of asymmetric synapse number: N=5 control, 5 Lgl1 cKO animals. FIG. 8F shows confocal images of dendrites (MAP2; blue) of neurons cultured for 14 DIV showing vGlutl puncta (green) and PSD95 puncta (red). White arrowheads indicate colocalized pre- and post-synaptic puncta. Scale bar: 10 μm. FIG. 8G shows quantification of puncta within ROIs including secondary dendrites of cultured hippocampal pyramidal neurons. N=5 control, 5 KO embryos. FIG. 8H shows quantification of kinetics of mEPSCs from slices from P13-15 control and Lgl1 cKO mice. n=22 control, 19 Lgl1 cKO neurons. FIG. 8I shows quantification of kinetics of mIPSCs from slices from P13-15 control and Lgl1 cKO mice. n=20 control, 19 Lgl1 cKO neurons. $^{*}p<0.05$; $^{**}p<0.01$.

FIG. 9A shows results of Western blots of total cell lysate and immunoprecipitation by anti-aPKC antibody from cultured neuronal progenitors treated with either AdGFP (Ctrl) or AdCre (cKO). FIG. 9B shows quantification of asymmetric synapse number in the region of the Schaffer Collateral 50 μm from the CA1 neuron layer in P14 control and aPKC dcKO animals. FIG. 9C shows quantification of asymmetric synapse number in the region of the Schaffer Collateral 50 μm from the CA1 neuron layer in 8-week older control and aPKC dcKO animals. $^{***}p<0.001$.

FIG. 10A shows quantification of asymmetric synapse number in the region of the Schaffer Collateral 50 μm from the CA1 neuron layer in P14 control and Lgl1:PKCι/λ: PKCξ tcKO animals. FIG. 10B shows quantification of asymmetric synapse number in the region of the Schaffer Collateral 50 μm from the CA1 neuron layer in 8-week old control and Lgl1:PKCι/λ: PKCλ tcKO animals.

FIG. 11A shows quantification of time spent self-grooming during the open field test. FIG. 11B shows quantification of rearing counts during the open field test. FIG. 11C shows quantification of spontaneous alternation in the Y-maze test following SLICK-H mediated Lgl1 deletion at P7/P8. N=18 control, 22 Lgl1 cKO. FIG. 11D shows total arm entries in the Y-maze test (not significant; p=0.0560) N=18 control, 22 Lgl1 cKO. FIG. 11E shows number of 15-degree head movements during the optomotor response task. N=18 control, 22 Lgl1 cKO. FIG. 11F shows quantification of the conditioned fear test following SLICK-H-mediated deletion of Lgl1. N=18 control, 22 Lgl1 cKO. FIG. 11G shows quantification of nestlet-shredding activity following conditional Lgl1 deletion at day P7. N=12 control, 12 Lgl1 cKO animals. **p<0.01.

FIG. 12A shows quantification of asymmetric synapse number in the region of the Schaffer Collateral 50 μm from the CA1 neuron layer in P14 $Lgl1^{+/+}$ and $Lgl1^{+/-}$ animals. FIG. 12B shows heatmaps and trajectories from $Lgl1^{+/+}$ and $Lgl1^{+/-}$ in the 10-minute open field (OF) test. FIG. 12C shows quantification of distance travelled during the OF test. N=34 control, 47 $Lgl1^{+/-}$ animals. FIG. 12D shows quantification of Thigmotaxis for control (black) and $Lgl1^{+/-}$ (gray) mice. FIG. 12E shows heatmaps of interaction bouts from Control and Lgl1 cKO from the sample phase of the novel object recognition (NOR) test. FIG. 12F shows quantification of preference for objects during the sample phase. N=17 control, 26 $Lgl1^{+/-}$ animals. FIG. 12G shows heat maps of interaction bouts from the object recognition phase of the NOR test performed 2 minutes after the sample phase. White asterisk indicates location of the novel object. FIG. 12H shows quantification of preference for objects. Positive value indicates preference for novel object. N=17 control, 26 $Lgl1^{+/-}$ animals. FIG. 121 shows heatmaps and quantification from the habituation phase of the Social Interaction test. N=25 control, 33 $Lgl1^{+/-}$ animals. FIG. 12J shows heatmaps and quantification from the social novelty phase of the SI test. N=25 control, 33 $Lgl1^{+/-}$ animals. FIG. 12K shows a comparison of weight gain of $Lgl1^{+/+}$ and $Lgl1^{+/-}$ mice during development and early adulthood. Note discontinuous X-axis after P28 (N=9-15 male $Lgl1^{+/+}$, 9-15 male $Lgl1^{+/-}$, 8-15 female $Lgl1^{+/+}$, 9-14 female $Lgl1^{+/-}$).

FIGS. 13A-13D show quantification of interaction time and preference from the habituation and social novelty phases of the Social Interaction test following administration of the indicated solution. White asterisk indicates location of the novel mouse in the social novelty phase. N=(Saline) 27 $Lgl1^{+/+}$, 30 $Lgl1^{+/-}$ animals; (ketamine) 14 $Lgl1^{+/+}$, 17 $Lgl1^{+/-}$ animals; (MK-801) 13 $Lgl1^{+/+}$, 14 $Lgl1^{+/-}$ animals; (Memantine) 19 $Lgl1^{+/+}$, 17 $Lgl1^{+/-}$ animals. FIG. 13E shows quantification of nestlet shredding activity following saline or ketamine injection. N=(Saline) 15 $Lgl1^{+/+}$, 14 $Lgl1^{+/-}$ animals; (ketamine) 15 $Lgl1^{+/+}$, 12 $Lgl1^{+/-}$ animals. *p<0.05; p<0.01; **p<0.0001.

DETAILED DESCRIPTION OF THE INVENTION

Figure 1A:
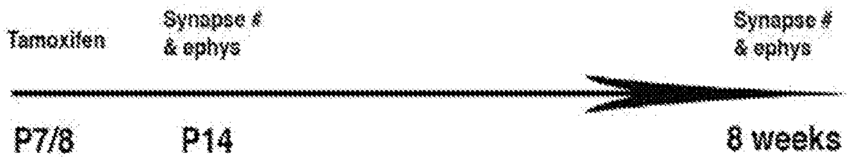
FIGS. 1A-1J are pictorial and graphical diagrams showing that Lgl1 Conditional Knockout in Pyramidal Neurons Led to Increased Numbers of Asymmetric Synapses.
Figure 1A:
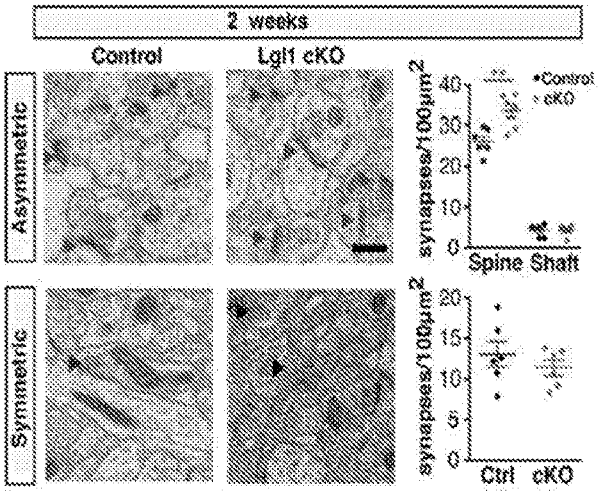

The present invention is based on the finding that N-methyl-D-aspartate (NMDA) receptor antagonists, at subanesthetic doses, alleviate social interaction deficits associated with behavioral disorders, such as Smith-Magenis Syndrome (SMS), autism, or attention deficit hyperactivity disorder (ADHD).

Unless described otherwise, all technical and scientific terms used herein have the same meaning as is commonly understood by one of ordinary skill in the art. For purposes of interpreting this specification, the following description of terms will apply and whenever appropriate, terms used in the singular will also include the plural and vice versa. All patents, applications, published applications, and other publications are incorporated by reference in their entirety. In the event that any description of terms set forth conflicts with any document incorporated herein by reference, the description of term set forth below shall control.

As used in this specification and the appended claims, the singular forms “a”, “an”, and “the” include plural references unless the context clearly dictates otherwise. Thus, for example, references to “the method” includes one or more methods, and/or steps of the type described herein which will become apparent to those persons skilled in the art upon reading this disclosure and so forth.

The terms “about” and “approximately” mean within 20%, within 15%, within 10%, within 9%, within 8%, within 7%, within 6%, within 5%, within 4%, within 3%, within 2%, within 1%, or less of a given value or range.

The term “comprising,” which is used interchangeably with “including,” “containing,” or “characterized by,” is inclusive or open-ended language and does not exclude additional, unrecited elements or method steps. The phrase “consisting of” excludes any element, step, or ingredient not specified in the claim. The phrase “consisting essentially of” limits the scope of a claim to the specified materials or steps and those that do not materially affect the basic and novel characteristics of the claimed invention. The present disclosure contemplates embodiments of the invention compositions and methods corresponding to the scope of each of these phrases. Thus, a composition or method comprising recited elements or steps contemplates particular embodiments in which the composition or method consists essentially of or consists of those elements or steps.

As used herein, “treatment” or “treating,” or “palliating” or “ameliorating” are used interchangeably herein. These terms refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made. Treatment includes preventing the disease, that is, causing the clinical symptoms of the disease not to develop by administration of a protective composition prior to the induction of the disease; suppressing the disease, that is, causing the clinical symptoms of the disease not to develop by administration of a protective composition after the inductive event but prior to the clinical appearance or reappearance of the disease; inhibiting the disease, that is, arresting the development of clinical symptoms by administration of a protective composition after their initial appearance; preventing re-occurring of the disease and/or relieving the disease, that is, causing the regression of clinical symptoms by administration of a protective composition after their initial appearance.

The term “effective amount” or “therapeutically effective amount” refers to the amount of an active agent sufficient to induce a desired biological result. That result may be alleviation of the signs, symptoms, or causes of a disease, or any other desired alteration of a biological system. The term "therapeutically effective amount" is used herein to denote any amount of the formulation which causes a substantial improvement in a disease condition when applied to the affected areas repeatedly over a period of time. The amount will vary with the condition being treated, the stage of advancement of the condition, and the type and concentration of formulation applied. Appropriate amounts in any given instance will be readily apparent to those skilled in the art or capable of determination by routine experimentation.

The term "subanesthetic," when used in reference to a dose, effective amount, or therapeutically effective amount, refers to the amount (or dosage) of an active agent that is insufficient to induce anesthesia. For example, analgesic effects of ketamine occur at plasma concentrations of 100 ng/mL to 200 ng/mL compared with plasma concentrations of 9,000 ng/mL to 25,000 ng/mL that are required to induce and maintain surgical anesthesia. Thus, an exemplary subanesthetic dose of ketamine is typically <0.5 mg/kg.

A "prophylactically effective amount" is an amount of a pharmaceutical composition that, when administered to a subject, will have the intended prophylactic effect, e.g., preventing, delaying, or reducing the likelihood of the onset (or reoccurrence) of a disease, disorder, condition, or associated symptom(s) (e.g., SMS). Typically, but not necessarily, since a prophylactic dose is used in subjects prior to or at an earlier stage of a disease, disorder, or condition, a prophylactically effective amount may be less than a therapeutically effective amount. The full therapeutic or prophylactic effect does not necessarily occur by administration of one dose, and may occur only after administration of a series of doses. Thus, a therapeutically or prophylactically effective amount may be administered in one or more administrations.

A "subject," "individual," or "patient," is used interchangeably herein, which refers to a vertebrate, preferably a mammal, more preferably a human. Mammals include, but are not limited to, murines, simians, humans, farm animals, sport animals, and pets. Tissues, cells and their progeny of a biological entity obtained in vitro or cultured in vitro are also encompassed.

As used herein, "promote" or "increase," or "promoting" or "increasing" are used interchangeably herein. These terms refer to the increase in a measured parameter (e.g., activity, expression, signal transduction, neuron degeneration) in a treated cell (tissue or subject) in comparison to an untreated cell (tissue or subject). A comparison can also be made of the same cell or tissue or subject between before and after treatment. The increase is sufficient to be detectable. In some embodiments, the increase in the treated cell is at least about 10%, 20%, 30%, 40%, 50%, 60%, 70%, 80%, 90%, 1-fold, 2-fold, 3-fold, 4-fold or more in comparison to an untreated cell.

As used herein, "inhibit," "prevent" or "reduce," or "inhibiting," "preventing" or "reducing" are used interchangeably herein. These terms refer to the decrease in a measured parameter (e.g., activity, expression, signal transduction, neuron degeneration) in a treated cell (tissue or subject) in comparison to an untreated cell (tissue or subject). A comparison can also be made of the same cell or tissue or subject between before and after treatment. The decrease is sufficient to be detectable. In some embodiments, the decrease in the treated cell is at least about 10%, 20%, 30%, 40%, 50%, 60%, 70%, 80%, 90%, or completely inhibited in comparison to an untreated cell. In some embodiments the measured parameter is undetectable (i.e., completely inhibited) in the treated cell in comparison to the untreated cell.

The terms "manage," "managing," and "management" refer to the beneficial effects that a subject derives from a therapy (e.g., a prophylactic or therapeutic agent), which does not result in a cure of the disease. In certain embodiments, a subject is administered one or more therapies (e.g., prophylactic or therapeutic agents to "manage" a neuronal disorder, one or more symptoms thereof, so as to prevent the progression or worsening of the disease.

The terms "blocking" agent, "antagonist," and "inhibitor" of a target molecule are used interchangeably herein to refer to an agent that reduces or inhibits a biological effect induced by the target molecule, e.g., in vivo or in vitro. The agent can be a small molecule compound or a biological molecule such as a nucleic acid or polypeptide. In assessing the strength of inhibition, the biological effect can be measured in the presence and absence of the candidate agent. In certain embodiments, the biological effect measured in the presence of the antagonist is equal to or less than 10%, 15%, 20%, 25%, 30%, 35%, 40%, 45%, 50%, 55%, 60%, 65%, 70%, 75%, 80%, 85%, 90%, 95%, or 98% of the same biological effect measured in the absence of the antagonist.

The term "selective inhibition" or "selectively inhibit" as referred to a biologically active agent refers to the agent's ability to preferentially reduce the target signaling activity as compared to off-target signaling activity, via direct or indirect interaction with the target.

An "agonist" of a target molecule refers to an agent that increases or enhances a biological effect induced by the target molecule, e.g., in vivo or in vitro. The agent can be a small molecule compound or a biological molecule such as a nucleic acid or polypeptide. In assessing the level of enhancement, the biological effect can be measured in the presence and absence of the candidate agent. In certain embodiments, the biological effect measured in the absence of the agonist is equal to or less than 10%, 15%, 20%, 25%, 30%, 35%, 40%, 45%, 50%, 55%, 60%, 65%, 70%, 75%, 80%, 85%, 90%, 95%, or 98% of the same biological effect measured in the presence of the agonist. For example, an agonist of Lgl as described herein can be a molecule that is capable of activating or otherwise increasing one or more of the biological activities of Lgl, such as in a cell expressing Lgl. In some embodiments, an agonist of Lgl (e.g., an agonistic antibody as described herein) may, for example, act by activating or otherwise increasing the activation and/or cell signaling pathways of a cell expressing a Lgl protein, thereby increasing a Lgl-mediated biological activity of the cell relative to the Lgl-mediated biological activity in the absence of agonist. In some embodiments, the cell expressing a Lgl protein is a neuron, and the Lgl-mediated biological activity is Lgl mediated formation of neuronal synapses.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrrolysine and selenocysteine.

The term “antibody” as used herein includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains (see Huse et al., *Science* 246:1275-1281, 1989, which is incorporated herein by reference). These and other methods of making, for example, chimeric, humanized, CDR-grafted, single chain, and bifunctional antibodies are well known (Winter and Harris, *Immunol. Today* 14:243-246, 1993; Ward et al., *Nature* 341:544-546, 1989; Harlow and Lane, Antibodies: A laboratory manual (Cold Spring Harbor Laboratory Press, 1999); Hilyard et al., *Protein Engineering: A practical approach* (IRL Press 1992); Borrabeck, *Antibody Engineering,* 2d ed. (Oxford University Press 1995); each of which is incorporated herein by reference). In addition, modified or derivatized antibodies, or antigen binding fragments of antibodies, such as pegylated (polyethylene glycol modified) antibodies, can be useful for the present methods.

Antibodies can be tested for anti-target polypeptide activity using a variety of methods well-known in the art. Various techniques may be used for screening to identify antibodies having the desired specificity, including various immunoassays, such as enzyme-linked immunosorbent assays (ELISAs), including direct and ligand-capture ELISAs, radioimmunoassays (RIAs), immunoblotting, and fluorescent activated cell sorting (FACS). Numerous protocols for competitive binding or immunoradiometric assays, using either polyclonal or monoclonal antibodies with established specificities, are well known in the art. Such immunoassays typically involve the measurement of complex formation between the target polypeptide and a specific antibody. A two-site, monoclonal-based immunoassay utilizing monoclonal antibodies reactive to two non-interfering epitopes on the target polypeptide is preferred, but other assays, such as a competitive binding assay, may also be employed. See, e.g., Maddox et al, 1983*, J Exp. Med.* 158:1211.

An “epitope” is the site on the surface of an antigen molecule to which a single antibody molecule binds, such as a localized region on the surface of an antigen that is capable of being bound to one or more antigen binding regions of an antibody, and that has antigenic or immunogenic activity in an animal, such as a mammal (e.g., a human), that is capable of eliciting an immune response. An epitope having immunogenic activity is a portion of a polypeptide that elicits an antibody response in an animal. An epitope having antigenic activity is a portion of a polypeptide to which an antibody binds as determined by any method well known in the art, including, for example, by an immunoassay. Antigenic epitopes need not necessarily be immunogenic. Epitopes often consist of chemically active surface groupings of molecules such as amino acids or sugar side chains and have specific three-dimensional structural characteristics as well as specific charge characteristics. Antibody epitopes may be linear epitopes or conformational epitopes. Linear epitopes are formed by a continuous sequence of amino acids in a protein. Conformational epitopes are formed of amino acids that are discontinuous in the protein sequence, but which are brought together upon folding of the protein into its three-dimensional structure. Induced epitopes are formed when the three-dimensional structure of the protein is in an altered conformation, such as following activation or binding of another protein or ligand.

The term “specific binding,” “specifically binds to,” or “is specific for” a particular polypeptide or an epitope on a particular polypeptide target as used herein refers to binding where a molecule binds to a particular polypeptide or epitope on a particular polypeptide without substantially binding to any other polypeptide or polypeptide epitope. For example, antibody that preferentially binds to a target molecule (such as the molecule, or an antigen or epitope thereof) over a reference molecule (such as the molecule, or an antigen or epitope thereof) can bind to the target molecule with a $K_D$ less than the $K_D$ exhibited relative to the reference molecule. In some embodiments, the antibody preferentially binds a target molecule with a $K_D$ less than half of the $K_D$ exhibited relative to the reference molecule. In some embodiments, the antibody preferentially binds a target molecule with a $K_D$ at least 10 times less than the $K_D$ exhibited relative to the reference molecule. In some embodiments, the antibody preferentially binds a target molecule with a $K_D$ with $K_D$ that is about 75%, about 50%, about 25%, about 10%, about 5%, about 2.5%, or about 1% of the $K_D$ exhibited relative to the reference molecule. In some embodiments, the ratio between the $K_D$ exhibited by the antibody when binding to the reference molecule and the $K_D$ exhibited when binding to the target molecule is at least 2 fold, at least 3 fold, at least 4 fold, at least 5 fold, at least 10 fold, at least 20 fold, at least 100 fold, at least 500 fold, at least $10^3$ fold, at least $10^4$ fold, or at least $10^5$ fold. The preferential binding can also be determined by binding assays and be indicated by, for example, fluorescence intensity (“MFI”).

A molecule (e.g., an agonistic or antagonistic agent) which “binds a target molecule of interest” is one that binds the target molecule with sufficient affinity such that the molecule is useful, for example, as a diagnostic or therapeutic agent in targeting a cell or tissue expressing the target molecule, and does not significantly cross-react with other molecules. In such embodiments, the extent of binding of the molecule to a “non-target” molecule will be less than about 10% of the binding of the molecule to its particular target molecule, for example, as determined by fluorescence activated cell sorting (FACS) analysis or RIA.

With regard to the binding of an antibody to a target molecule (e.g., aPKC), the term “specific binding,” “specifically binds to,” or “is specific for” a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. The term “specific binding,” “specifically binds to,” or “is specific for” a particular polypeptide or an epitope on a particular polypeptide target as used herein refers to binding where a molecule binds to a particular polypeptide or epitope on a particular polypeptide without substantially binding to any other polypeptide or polypeptide epitope. In certain embodiments, an antibody that binds to aPKC has a dissociation constant (KD) of less than or equal to 10 nM, 5 nM, 4 nM, 3 nM, 2 nM, 1 nM, 0.9 nM, 0.8 nM, 0.7 nM, 0.6 nM, 0.5 nM, 0.4 nM, 0.3 nM, 0.2 nM, or 0.1 nM.

The term “variant” applies to both amino acid and nucleic acid sequences. With respect to particular nucleic acid sequences, a variant refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are “silent variations,” which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

The term “variant” when used in relation to a protein or peptide may refer to a peptide or polypeptide comprising one or more (such as, for example, about 1 to about 25, about 1 to about 20, about 1 to about 15, about 1 to about 10, or about 1 to about 5) amino acid sequence substitutions, deletions, and/or additions as compared to a native or unmodified sequence. Variants may be naturally occurring, such as allelic or splice variants, or may be artificially constructed. Polypeptide variants may be prepared from the corresponding nucleic acid molecules encoding the variants. In specific embodiments, the variant of a protein or peptide retains functional activity of the native protein or peptide. In certain embodiments, the variant is encoded by a single nucleotide polymorphism (SNP) variant of a nucleic acid molecule that encodes the native protein or peptide. A functional variant of a peptide refers to a variant of the peptide that retains at least one function or activity of interest of the native peptide.

“Percentage of sequence identity” is determined by comparing two optimally aligned sequences over a comparison window, wherein the portion of the polynucleotide sequence in the comparison window may comprise additions or deletions (i.e., gaps) as compared to the reference sequence (e.g., a polypeptide of the invention), which does not comprise additions or deletions, for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms “identical” or percent “identity,” in the context of two or more nucleic acids or polypeptide sequences, refer to two or more sequences or subsequences that are the same sequences. Two sequences are “substantially identical” if two sequences have a specified percentage of amino acid residues or nucleotides that are the same (i.e., 60% identity, optionally 65%, 70%, 75%, 80%, 85%, 90%, or 95% identity over a specified region, or, when not specified, over the entire sequence), when compared and aligned for maximum correspondence over a comparison window, or designated region as measured using one of the following sequence comparison algorithms or by manual alignment and visual inspection. The invention provides polypeptides that are substantially identical to the polypeptides, respectively, exemplified herein, as well as uses thereof including, but not limited to, use for treating or preventing neurological diseases or disorders, e.g., neurodegenerative diseases or disorders, and/or treating SCI. Optionally, the identity exists over a region that is at least about 50 nucleotides in length, or more preferably over a region that is 100 to 500 or 1000 or more nucleotides in length, or the entire length of the reference sequence.

A “genetic knock out” refers to partial or complete suppression of the expression of a protein encoded by an endogenous DNA sequence in a cell. The “knockout” (KO) can be affected by targeted deletion of the whole or part of a gene encoding a protein. Alternatively, the transgenic organism can be obtained by the targeted mutation of a functional protein in an embryonic stem cell. As a result, the deletion or mutation may prevent or reduce the expression of the protein in any cell in the whole animal in which it is normally expressed, or results in the expression of a mutant protein having a biological function different than the normal/wild-type protein.

The term “knockout animal” and “transgenic animal”, refer to a transgenic animal wherein a given gene has been suppressed or mutated by recombination with a targeting vector. It is to be emphasized that the term is intended to include all progeny generations. Thus, the founder animal and all F1, F2, F3, and so on, progeny thereof, are included.

As used herein, the phrase “conditional knockout,” or “cKO,” when used to describe a non-human transgenic mammal such as a mouse, refers to mice containing a knock-out of a specific gene in a certain tissue. The creation of a genetically engineered cKO mouse involves inserting specific DNA sequences, such as a knock-out construct/vector, into the mouse DNA. The inserted sequences are recognized by two DNA specific enzymes, frt recombinase (also known as flippase) and Cre recombinase, not normally present in mice. Cre recombinase recognition sites are termed loxP sites and flippase recognition sites are termed frt sites. Each of these enzymes can cut and remove a DNA sequence that is flanked by its recognition sites. This can lead to disruption of gene function if a functional DNA sequence of the gene of interest is removed. In addition, a selectable marker gene is inserted into the mouse, the introduction of which allows selection of embryonic mouse cells (stem cells) that contain the Cre recombination or flippase recognition sites. The resultant mouse is a conditional knockout mouse.

“Synapse” or is a term of art and refers to the communicating cell-cell junctions that allow signals to pass from a nerve cell (i.e. neuron) to a target cell (e.g. a neighboring neuron or a muscle cell). A synapse is composed of a presynaptic membrane of a presynaptic cell (e.g., a membrane of an axon of a neuron) and a postsynaptic membrane of a postsynaptic cell (e.g., a membrane of dendrite of a neuron, or of a specialized region of a muscle or a secretory cell), with the presynaptic and postsynaptic membranes typically opposing each other. The gap between the opposing synaptic membranes of a synapse is known as the synaptic cleft. A neuron typically forms a plurality of synapse with its neighboring cells. The neuron typically serves as the presynaptic cell for synapses formed on its axon, and as the postsynaptic cell for synapses formed on its dendrite. Accordingly, a "presynaptic site of a neuron" as used herein refers to the synaptic site of a neuron, for which synapses the neuron serves as the presynaptic cell; a "postsynaptic site of a neuron" as used herein refers to the synaptic site of a neuron, for which synapse the neuron serves as the postsynaptic cell.

As used herein, the term "neuron" includes a neuron and a portion or portions thereof (e.g., the neuron cell body, an axon, or a dendrite). The term "neuron" as used herein denotes nervous system cells that include a central cell body or soma, and two types of extensions or projections: dendrites, by which, in general, the majority of neuronal signals are conveyed to the cell body, and axons, by which, in general, the majority of neuronal signals are conveyed from the cell body to effector cells, such as target neurons or muscle. Neurons can convey information from tissues and organs into the central nervous system (afferent or sensory neurons) and transmit signals from the central nervous systems to effector cells (efferent or motor neurons). Other neurons, designated interneurons, connect neurons within the central nervous system (the brain and spinal column). Certain specific examples of neuron types that may be subject to treatment or methods according to the invention include cerebellar granule neurons, dorsal root ganglion neurons, and cortical neurons.

The term "neuronal degeneration" is used broadly and refers to any pathological changes in neuronal cells, including, without limitation, death or loss of neuronal cells, any changes that precede cell death, and any reduction or loss of an activity or a function of the neuronal cells. The pathological changes may be spontaneous or may be induced by any event and include, for example, pathological changes associated with apoptosis. The neurons may be any neurons, including without limitation sensory, sympathetic, parasympathetic, or enteric, e.g., dorsal root ganglia neurons, motor neurons, and central neurons, e.g., neurons from the spinal cord. Neuronal degeneration or cell loss is a characteristic of a variety of neurological diseases or disorders, e.g., neurodegenerative diseases or disorders. In some embodiments, the neuron is a sensory neuron. In some embodiments, the neuron is a motor neuron. In some embodiments, the neuron is a damaged spinal cord neuron.

In some embodiments, degeneration occurs in a portion of the neuron such as the neuron cell body, an axon, or a dendrite. Accordingly, the degeneration can be inhibited in the degenerated portion or portions of the neuron. In some embodiments, the degeneration of an axon of the neuron is inhibited. In some embodiments, the degeneration of a cell body of the neuron is inhibited. The axon can be an axon of any neuron. For example, in some embodiments, the axon is a spinal cord commissural axon, or an upper motor neuron axon, or a central nervous system axon.

"Administer" or "administration" refers to the act of injecting or otherwise physically delivering a substance as it exists outside the body into a patient, such as by mucosal, intradermal, intravenous, intramuscular delivery, and/or any other method of physical delivery described herein or known in the art. When a disease, disorder, condition, or a symptom thereof, is being treated, administration of the substance typically occurs after the onset of the disease, disorder, condition, or symptoms thereof. When a disease, disorder, condition, or symptoms thereof, are being prevented, administration of the substance typically occurs before the onset of the disease, disorder, condition, or symptoms thereof.

NMDA receptors are key in the progression of excitotoxicity (a process in which an excessive amount of extracellular glutamate overexcites glutamate receptors and harms neurons). Thus, NMDA receptor antagonists have been extensively studied for use in treatment of diseases with excitotoxic components, such as stroke, traumatic brain injury, and neurodegenerative diseases such as Huntington's, Alzheimer's, and amyotrophic lateral sclerosis. Such studies have demonstrated NMDA receptor antagonist effectiveness in protecting neurons in cell culture and animal models of excitotoxic neurodegeneration. However, NMDA antagonists have largely failed to show safety in clinical trials, possibly due to inhibition of NMDA receptor function that is necessary for normal neuronal function.

Although many of the proteins in glutamatergic synapses have been identified and their roles in synapse formation and function have been studied, the signaling logic that orchestrates the assembly of hundreds of proteins into a highly organized and dynamic structure remains unclear. As demonstrated herein, a conserved apical-basal polarity signaling component, Lgl1, is localized in the PSD and regulates synapse numbers and compositions of key synaptic proteins and glutamate receptors, probably by interaction with its conserved binding partners, particularly the membrane-associated guanylate kinases (MAGUKs). Atypical PKC (aPKC) has been studied for its role in memory formation and consolidation.

Members of the MAGUK family include discs large homolog 1 (DLG1), which is also known as synapse-associated protein 97 (SAP97), synapse-associated protein 102 (SAP102), postsynaptic density protein 95 (PSD95) and postsynaptic density protein 93 (PSD93), which are defined by their inclusion of PDZ, SH3 and GUK domains, although many of them also contain regions homologous of CaMKII, WW and L27 domains (Woods D F, Bryant P J (December 1993). "ZO-1, DlgA and PSD-95/SAP90: homologous proteins in tight, septate and synaptic cell junctions". Mech. Dev. 44 (2-3):85-9). The GUK domain that they have is structurally very similar to that of the guanylate kinases, however it is known to be catalytically inactive as the P-Loop which binds ATP is absent. The number of PDZ domain copies varies between different members of the MAGUK family. The PDZ domains found within each family member often have different binding partners, due to variations in their amino acid compositions.

In some embodiments, the SAP97 has an amino acid sequence of:

(SEQ ID NO: 7)

```
MPVRKQDTQRALHLLEEYRSKLSQTEDRQLRSSIERVINIFQSNLFQAL

IDIQEFYEVTLLDNPKCIDRSKPSEPIQPVNTWEISSLPSSTVTSETLP

SSLSPSVEKYRYQDEDTPPQEHISPQITNEVIGPELVHVSEKNLSEIEN

VHGFVSHSHISPIKPTEAVLPSPPTVPVIPVLPVPAENTVILPTIPQAN

PPPVLVNTDSLETPTYVNGTDADYEYEEITLERGNSGLGFSIAGGTDNP

HIGDDSSIFITKIITGGAAAQDGRLRVNDCILRVNEVDVRDVTHSKAVE

ALKEAGSIVRLYVKRRKPVSEKIMEIKLIKGPKGLGFSIAGGVGNQHIP
```

-continued

GDNSIYVTKIIEGGAAHKDGKLQIGDKLLAVNNVCLEEVTHEEAVTALK
NTSDFVYLKVAKPTSMYMNDGYAPPDITNSSSQPVDNHVSPSSFLGQTP
ASPARYSPVSKAVLGDDEITREPRKVVLHRGSTGLGFNIVGGEDGEGIF
ISFILAGGPADLSGELRKGDRIISVNSVDLRAASHEQAAAALKNAGQAV
TIVAQYRPEEYSRFEAKIHDLREQMMNSSISSGSGSLRTSQKRSLYVRA
LFDYDKTKDSGLPSQGLNFKFGDILHVINASDDEWWQARQVTPDGESDE
VGVIPSKRRVEKKERARLKTVKFNSKTRDKGEIPDDMGSKGLKHVTSNA
SDSESSYRGQEEYVLSYEPVNQQEVNYTRPVIILGPMKDRINDDLISEF
PDKFGSCVPHTTRPKRDYEVDGRDYHFVTSREQMEKDIQEHKFIEAGQY
NNHLYGTSVQSVREVAEKGKHCILDVSGNAIKRLQIAQLYPISIFIKPK
SMENIMEMNKRLTEEQARKTFERAMKLEQEFTEHFTAIVQGDTLEDIYN
QVKQIIEEQSGSYIWVPAKEKL. GenBank ™ accession number NM_001098424 provides an exemplary human SAP97 nucleic acid sequence.

In some embodiments, the SAP102 has an amino acid sequence of:

(SEQ ID NO: 8)
MHKHQHCCKCPECYEVTRLAALRRLEPPGYGDWQVPDPYGPGGGNGASA
GYGGYSSQTLPSQAGATPTPRTKAKLIPTGRDVGPVPPKPVPGKSTPKL
NGSGPSWWPECTCTNRDWYEQVNGSDGMFKYEEIVLERGNSGLGFSIAG
GIDNPHVPDDPGIFITKIIPGGAAAMDGRLGVNDCVLRVNEVDVSEVVH
SRAVEALKEAGPVVRLVVRRRQPPPETIMEVNLLKGPKGLGFSIAGGIG
NQHIPGDNSIYITKIIEGGAAQKDGRLQIGDRLLAVNNTNLQDVRHEEA
VASLKNTSDMVYLKVAKPGSLHLNDMVAPPDYASTFTALADNHISHNSS
LGYLGAVESKVSYPAPPQVPPTRYSPIPRHMLAEEDFTREPRKIILHKG
STGLGFNIVGGEDGEGIFVSFILAGGPADLSGELRRGDRILSVNGVNLR
NATHEQAAAALKRAGQSVTIVAQYRPEEYSRFESKIHDLREQMMNSSMS
SGSGSLRTSEKRSLYVRALFDYDRTRDSCLPSQGLSFSYGDILHVINAS
DDEWWQARLVTPHGESEQIGVIPSKKRVEKKERARLKTVKFHARTGMIE
SNRDFPGLSDDYYGAKNLKGQEDAILSYEPVTRQEIHYARPVIILGPMK
DRVNDDLISEFPHKFGSCVPHTTRPRRDNEVDGQDYHFVVSREQMEKDI
QDNKFIEAGQFNDNLYGTSIQSVRAVAERGKHCILDVSGNAIKRLQQAQ
LYPIAIFIKPKSIEALMEMNRRQTYEQANKIYDKAMKLEQEFGEYFTAI
VQGDSLEEIYNKIKQIIEDQSGHYIWVPSPEKL. GenBank ™ accession number NM_021120 provides an exemplary human SAP102 nucleic acid sequence.

In some embodiments, the PSD95 has an amino acid sequence of:

(SEQ ID NO: 9)
MDCLCIVTTKKYRYQDEDTPPLEHSPAHLPNQANSPPVIVNTDTLEAPG
YVNGTEGEMEYEEITLERGNSGLGFSIAGGTDNPHIGDDPSIFITKIIP
GGAAAQDGRLRVNDSILFVNEVDVREVTHSAAVEALKEAGSIVRLYVMR
RKPPAEKVMEIKLIKGPKGLGFSIAGGVGNQHIPGDNSIYVTKIIEGGA
AHKDGRLQIGDKILAVNSVGLEDVMHEDAVAALKNTYDVVYLKVAKPSN
AYLSDSYAPPDITTSYSQHLDNEISHSSYLGTDYPTAMTPTSPRRYSPV
AKDLLGEEDIPREPRRIVIHRGSTGLGFNIVGGEDGEGIFISFILAGGP
ADLSGELRKGDQILSVNGVDLRNASHEQAAIALKNAGQTVTIIAQYKPE
EYSRFEAKIHDLREQLMNSSLGSGTASLRSNPKRGFYIRALFDYDKTKD
CGFLSQALSFRFGDVLHVIDASDEEWWQARRVHSDSETDDIGFIPSKRR
VERREWSRLKAKDWGSSSGSQGREDSVLSYETVTQMEVHYARPIIILGP
TKDRANDDLLSEFPDKFGSCVPHTTRPKREYEIDGRDYHFVSSREKMEK
DIQAHKFIEAGQYNSHLYGTSVQSVREVAEQGKHCILDVSANAVRRLQA
AHLHPIAIFIRPRSLENVLEINKRITEEQARKAFDRATKLEQEFTECFS
AIVEGDSFEEIYHKVKRVIEDLSGPYIWVPARERL. GenBank ™ accession number NM_001128827 provides an exemplary human PSD95 nucleic acid sequence.

In some embodiments, the PSD93 has an amino acid sequence of:

(SEQ ID NO: 10)
MGIFKSSLFQALLDIQEFYEVTLLNSQKSCEQKIEEANQVLQKWEKTSL
LAPCHDRLQKSSELTDCSGSKENASCIEQNKENQSFENETDETTTQNQG
RCPAQNCSVEAPAWMPVHHCTKYRYQDEDAPHDHSLPRLTHEVRGPELV
HVSEKNLSQIENVHGYVLQSHISPLKASPAPIIVNTDTLDTIPYVNGTE
IEYEFEEITLERGNSGLGFSIAGGTDNPHIGDDPGIFITKIIPGGAAAE
DGRLRVNDCILRVNEVDVSEVSHSKAVEALKEAGSIVRLYVRRRRPILE
TVVEIKLFKGPKGLGFSIAGGVGNQHIPGDNSIYVTKIIDGGAAQKDGR
LQVGDRLLMVNNYSLEEVTHEEAVAILKNTSEVVYLKVGKPTTIYMTDP
YGPPDITHSYSPPMENHLLSGNNGTLEYKTSLPPISPGRYSPIPKHMLV
DDDYTRPPEPVYSTVNKLCDKPASPRHYSPVECDKSFLLSAPYSHYHLG
LLPDSEMTSHSQHSTATRQPSMTLQRAVSLEGEPRKVVLHKGSTGLGFN
IVGGEDGEGIFVSFILAGGPADLSGELQRGDQILSVNGIDLRGASHEQA
AAALKGAGQTVTIIAQYQPEDYARFEAKIHDLREQMMNHSMSSGSGSLR
TNQKRSLYVRAMFDYDKSKDSGLPSQGLSFKYGDILHVINASDDEWWQA
RRVMLEGDSEEMGVIPSKRRVERKERARLKTVKFNAKPGVIDSKGSFND
KRKKSFIFSRKFPFYKNKEQSEQETSDPERGQEDLILSYEPVTRQEINY
TRPVIILGPMKDRINDDLISEFPDKFGSCVPHTTRPKRDYEVDGRDYHF
VISREQMEKDIQEHKFIEAGQYNDNLYGTSVQSVRFVAERGKHCILDVS
GNAIKRLQVAQLYPIAIFIKPRSLEPLMEMNKRLTEEQAKKTYDRAIKL
EQEFGEYFTAIVQGDTLEDIYNQCKLVIEEQSGPFIWIPSKEKL. GenBank ™ accession number NM_001142699 provides an exemplary human PSD93 nucleic acid sequence.

Protein kinase C (PKC) is a family of protein kinase enzymes that are involved in controlling the function of other proteins through the phosphorylation of hydroxyl groups of serine and threonine amino acid residues on these proteins, or a member of this family. PKC enzymes in turn are activated by signals such as increases in the concentration of diacylglycerol (DAG) or calcium ions ($Ca^{2+}$) (Wilson C H, Ali E S, Scrimgeour N, Martin A M, Hua J, Tallis G A, Rychkov G Y, Barritt G J (2015). "Steatosis inhibits liver cell store-operated $Ca^{2+}$ entry and reduces ER $Ca^{2+}$ through a protein kinase C-dependent mechanism". The Biochemical Journal. 466 (2): 379-90). The PKC family consists of fifteen isozymes in humans. They are divided into three subfamilies, based on their second messenger requirements: conventional (or classical), novel, and atypical (Nishizuka Y (April 1995). "Protein kinase C and lipid signaling for sustained cellular responses". FASEB Journal. 9 (7): 484-96). Conventional (c)PKCs contain the isoforms ∝, βI, βII, and γ. These require $Ca^{2+}$, DAG, and a phospholipid such as phosphatidylserine for activation. Novel (n)PKCs include the δ, ε, η, and θ isoforms, and require DAG, but do not require $Ca^{2+}$ for activation. However, atypical PKCs (aPKC) (including protein kinase c ξ and ι/λ isoforms) require neither $Ca^{2+}$ nor diacylglycerol for activation.

In some embodiments, the aPKCι/λ isoform has an amino acid sequence of:

(SEQ ID NO: 1)

```
MPTQRDSSTMSHTVAGGGSGDHSHQVRVKAYYRGDIMITHFEPSISFEG
LCNEVRDMCSFDNEQLFTMKWIDEEGDPCTVSSQLELEEAFRLYELNKD
SELLIHVFPCVPERPGMPCPGEDKSIYRRGARRWRKLYCANGHTFQAKR
FNRRAHCAICTDRIWGLGRQGYKCINCKLLVHKKCHKLVTIECGRHSLP
QEPVMPMDQSSMHSDHAQTVIPYNPSSHESLDQVGEEKEAMNTRESGKA
SSSLGLQDFDLLRVIGRGSYAKVLLVRLKKTDRIYAMKVVKKELVNDDE
DIDWVQTEKHVFEQASNHPFLVGLHSCFQTESRLFFVIEYVNGGDLMFH
MQRQRKLPEEHARFYSAEISLALNYLHERGITYRDLKLDNVLLDSEGHI
KLTDYGMCKEGLRPGDTTSTFCGTPNYIAPEILRGEDYGFSVDWWALGV
LMFEMMAGRSPFDIVGSSDNPDQNTEDYLFQVILEKQIRIPRSLSVKAA
SVLKSFLNKDPKERLGCHPQTGFADIQGHPFFRNVDWDMMEQKQVVPPF
KPNISGEFGLDNFDSQFTNEPVQLTPDDDDIVRKIDQSEFEGFEYINPL
LMSAEECV.
```

GenBank ™ accession number NM_002740 provides an exemplary human protein kinase C iota nucleic acid sequence.

In some embodiments, the aPKC ξ isoform 1 has an amino acid sequence of:

(SEQ ID NO: 2)

```
MPSRTGPKMEGSGGRVRLKAHYGGDIFITSVDAATTFEELCEEVRDMCR
LHQQHPLTLKWVDSEGDPCTVSSQMELEEAFRLARQCRDEGLIIHVFPS
TPEQPGLPCPGEDKSIYRRGARRWRKLYRANGHLFQAKRFNRRAYCGQC
SERIWGLARQGYRCINCKLLVHKRCHGLVPLTCRKHMDSVMPSQEPPVD
DKNEDADLPSEETDGIAYISSSRKHDSIKDDSEDLKPVIDGMDGIKISQ
```

-continued

```
GLGLQDFDLIRVIGRGSYAKVLLVRLKKNDQIYAMKVVKKELVHDDEDI
DWVQTEKHVFEQASSNPFLVGLHSCFQTTSRLFLVIEYVNGGDLMFHMQ
RQRKLPEEHARFYAAEICIALNFLHERGITYRDLKLDNVLLDADGHIKL
TDYGMCKEGLGPGDTTSTFCGTPNYIAPEILRGEEYGFSVDWWALGVLM
FEMMAGRSPFDIITDNPDMNTEDYLFQVILEKPIRIPRFLSVKASHVLK
GFLNKDPKERLGCRPQTGFSDIKSHAFFRSIDWDLLEKKQALPPFQPQI
TDDYGLDNFDTQFTSEPVQLTPDDEDAIKRIDQSEFEGFEYINPLLLST
EESV.
```

GenBank ™ accession number NM_002744 provides an exemplary human protein kinase C zeta nucleic acid sequence.

In some embodiments, the aPKC ξ isoform 2 has an amino acid sequence of:

(SEQ ID NO: 3)

```
MDSVMPSQEPPVDDKNEDADLPSEETDGIAYISSSRKHDSIKDDSEDLK
PVIDGMDGIKISQGLGLQDFDLIRVIGRGSYAKVLLVRLKKNDQIYAMK
VVKKELVHDDEDIDWVQTEKHVFEQASSNPFLVGLHSCFQTTSRLFLVI
EYVNGGDLMFHMQRQRKLPEEHARFYAAEICIALNFLHERGITYRDLKL
DNVLLDADGHIKLTDYGMCKEGLGPGDTTSTFCGTPNYIAPEILRGEEY
GFSVDWWALGVLMFEMMAGRSPFDIITDNPDMNTEDYLFQVILEKPIRI
PRFLSVKASHVLKGFLNKDPKERLGCRPQTGFSDIKSHAFFRSIDWDLL
EKKQALPPFQPQITDDYGLDNFDTQFTSEPVQLTPDDEDAIKRIDQSEF
EGFEYINPLLLSTEESV.
```

GenBank ™ accession number NM_001033581 provides another exemplary human protein kinase C zeta nucleic acid sequence.

The Vangl family proteins are components of the non-canonical Wnt Planar cell polarity pathway. In humans, at least three Vangl proteins, Vangl1 and Vangl2, belong to this family. The term "Van Gogh-like Protein," "Vang-like Protein," "VANGL planar cell polarity protein," or "Vangl" encompasses a polypeptide ("polypeptide" and "protein" are used interchangeably herein), including any native polypeptide, from any vertebrate source, including mammals such as primates (e.g., humans and cynomolgus monkeys (cynomolgus)), dogs, and rodents (e.g., mice and rats), unless otherwise indicated. In certain embodiments, the terms include "related Vangl polypeptides," including SNP variants thereof. The term "Vangl" also encompasses "full-length," unprocessed Vangl as well as any form of Vangl that results from processing in the cell.

In some embodiments, the Vangl1 has an amino acid sequence of:

(SEQ ID NO: 4)

```
MDTESTYSGYSYYSSHSKKSHRQGERTRERHKSPRNKDGRGSEKSVTIQ
PPTGEPLLGNDSTRTEEVQDDNWGETTTAITGTSEHSISQEDIARISKD
MEDSVGLDCKRYLGLTVASFLGLLVFLTPIAFILLPPILWRDELEPCGT
ICEGLFISMAFKLLILLIGTWALFFRKRRADMPRVFVFRALLLVLIFLF
```

-continued

VVSYWLFYGVRILDSRDRNYQGIVQYAVSLVDALLFIHYLAIVLLELRQ

LQPMFTLQVVRSTDGESRFYSLGHLSIQRAALVVLENYYKDFTIYNPNL

LTASKFRAAKHMAGLKVYNVDGPSNNATGQSRAMIAAAARRRDSSHNEL

YYEEAEHERRVKKRKARLVVAVEEAFIHIQRLQAEEQQKAPGEVMDPRE

AAQAIFPSMARALQKYLRITRQQNYHSMESILQHLAFCITNGMTPKAFL

ERYLSAGPTLQYDKDRWLSTQWRLVSDEAVTNGLRDGIVFVLKCLDFSL

VVNVKKIPFIILSEEFIDPKSHKFVLRLQSETSV. GenBank ™ accession number NM_138959 provides another exemplary human Vangl1 nucleic acid sequence.

In some embodiments, the Vangl2 has an amino acid sequence of:

(SEQ ID NO: 5)

MDTESQYSGYSYKSGHSRSSRKHRDRRDRHRSKSRDGGRGDKSVTIQAP

GEPLLDNESTRGDERDDNWGETTTVVTGTSEHSISHDDLTRIAKDMEDS

VPLDCSRHLGVAAGATLALLSFLTPLAFLLLPPLLWREELEPCGTACEG

LFISVAFKLLILLLGSWALFFRRPKASLPRVFVLRALLMVLVFLLVVSY

WLFYGVRILDARERSYQGVVQFAVSLVDALLFVHYLAVVLLELRQLQPQ

FTLKVVRSTDGASRFYNVGHLSIQRVAVWILEKYYHDFPVYNPALLNLP

KSVLAKKVSGFKVYSLGEENSTNNSTGQSRAVIAAAARRRDNSHNEYYY

EEAEHERRVRKRRARLVVAVEEAFTHIKRLQEEEQKNPREVMDPREAAQ

AIFASMARAMQKYLRTTKQQPYHTMESILQHLEFCITHDMTPKAFLERY

LAAGPTIQYHKERWLAKQWTLVSEEPVTNGLKDGIVFLLKRQDFSLVVS

TKKVPFFKLSEEFVDPKSHKFVMRLQSETSV. GenBank ™ accession number NM_020335 provides another exemplary human Vangl2 nucleic acid sequence.

Lethal giant larvae (Lgl1) is a key component of the highly conserved apical-basal polarity signaling pathway, which polarizes epithelial cells and tissues along the apical and basolateral axis. Lgl1 forms the basolateral complexes with Scribble and Discs Large (Dlg) and mutually excludes and antagonizes the function of the apical complexes, such as the aPKC/Par3/Par6 complex. Lgl1 has been implicated in polarized exocytosis and is essential for establishing or maintaining apical-basal polarity (Betschinger et al., 2003; Georgiou et al., 2008; Macara, 2004; Yamanaka et al., 2006; Yamanaka et al., 2003). Dlg homologs are important post-synaptic scaffold proteins, called MAGUKs (Zhu et al., 2016). MAGUK proteins play essential roles in postsynaptic density organization and glutamate receptor trafficking and clustering. In addition, Lgl1 has been shown to associate and co-traffic with FMRP (Zarnescu et al., 2005), a translational regulator of many synaptic components. Apical-basal and planar polarity pathways are known to interact with each other. For example, apical-basal polarity signaling has been recently shown to regulate the location of PCP signaling (Chuykin et al., 2018). The locus for Lgl1 lies within a refined consensus deletion site of ~950 kb for SMS that has been reported in genetic studies of patients carrying the chromosomal deletion (Vlangos et al., 2003).

In some embodiments, the Lgl1 has an amino acid sequence of:

(SEQ ID NO: 6)

MMKFRFRRQGADPQREKLKQELFAFNKTVEHGFPNQPSALAFDPELRIM

AIGTRSGAVKIYGAPGVEFTGLHRDAATVTQMHFLTGQGRLLSLLDDSS

LHLWEIVHHNGCAHLEEALSFQLPSRPGFDGASAPLSLTRVTVVLLVAA

SDIAALGTEGSSVFFLDVTTLTLLEGQTLAPGEVLRSVPDDYRCGKALG

PVESLQGHLRDPTKILIGYSRGLLVIWNQASQCVDHIFLGNQQLESLCW

GRDSSTVVSSHSDGSYAVWSVDAGSFPTLQPTVATTPYGPFPCKAINKI

LWRNCESGGHFIIFSGGMPRASYGDRHCVSVLRAETLVTLDFTSRIIDF

FTVHSTRPEDEFDDPQALAVLLEEELVVLDLQTPGWPAVPAPYLAPLHS

SAITCSAHVASVPAKLWARIVSAGEQQSPQPVSSALSWPITGGRNLAQE

PSQRGLLLTGHEDGTVRFWDASGVALRPLYKLSTAGLFQTDCEHADSLA

QAAEDDWPPFRKVGCFDPYSDDPRLGVQKVALCKYTAQMVVAGTAGQVL

VLELSDVPVEQAVSVAIIDLLQDREGFTWKGHERLSPRTGPLPWPAGFQ

PRVLVQCLPPAAVTAVTLHTEWSLVAFGTSHGFGLFDYQRKSPVLARCT

LHPNDSLAMEGPLSRVKSLKKSLRQSFRRIRKSRVSGKKRAANASSKLQ

EANAQLAEQACPHDVEMTPVQRRIEPRSADDSLSGVVRCLYFADTFLRD

GAHHGPTMWAGTNSGSVFAYALEVPAAAVGGEKRPEQAVEAVLGKEVQL

MHRAPVVAIAVLDGRGRPLPEPYEASRDLAQAPDMQGGHAVLIASEEQF

KVFTLPKVSAKTKFKLTAHEGCRVRKVALATFASVACEDYAETCLACLT

NLGDVHVFSVPGLRPQVHYSCIRKEDISGIASCVFTRHGQGFYLISPSE

FERFSLSARNITEPLCSLDINWPRDATQASYRIRESPKLSQANGTPSIL

LAPQSLDGSPDPAHSMGPDTPEPPEAALSPMSIDSATSADTTLDTTGDV

TVEDVKDFLGSSEESEKNLRNLAEDEAHACAILIK. GenBank ™ accession number NM_004140 provides an exemplary human Lgl1 nucleic acid sequence.

As demonstrated herein, conditional knockout (cKO) of Lgl1 in adulthood resulted in increased glutamatergic synapse numbers and reduced AMPA/NMDA ratio. In addition, adult deletion of Lgl1 leads to impairment of LTP induction and Paired-pulse facilitation, suggesting that Lgl1 is require for adult synaptic plasticity. Lgl1 is frequently deleted in SMS, therefore, a number of behavioral tests were performed. Conditional knockout of Lgl1 from either day P7 or in adulthood leads to behavioral deficits, including hyperactivity, cognitive impairment and social interaction, consistent with the autism-like symptoms in SMS. As SMS involves the microdeletion of one of the chromosomes, the Lgl1$^{+/-}$ mice were analyzed and it was found that Lgl1$^{+/-}$ mice did have increased synapse numbers, impaired social interaction and increased stereotyped repetitive behavior, suggesting that Lgl1 is a candidate gene that contributes to the autism-like symptoms of SMS.

As demonstrated herein, conditional deletion of both isoforms of aPKCs at P7 and P8 led to a reduction in synapse number in adulthood and cognitive and social deficits. The observation that deletion of Lgl1 or aPKC both lead to behavioral changes indicates that synapse number must be optimally controlled for behavioral functions and changes in either direction lead to impairment. Triple conditional knockout of Lgl1 and aPKC isoforms rescued the number of the asymmetric synapses and cognitive function, supporting their antagonistic functions in synapse formation.

Lgl1 forms a basal complex with Discs Large, which is the homolog of MAGUKs, essential scaffold proteins in the postsynaptic density, which regulate trafficking and clustering of glutamate receptors. It was found that in Lgl1 cKO, the composition of the MAGUKs in the glutamatergic synapses is altered, with SAP97 (Dlg1) significantly increased in both the total and membrane surface fractions and the other three MAGUKs, SAP102, PSD95 and PSD93 greatly reduced.

Figure 3A:
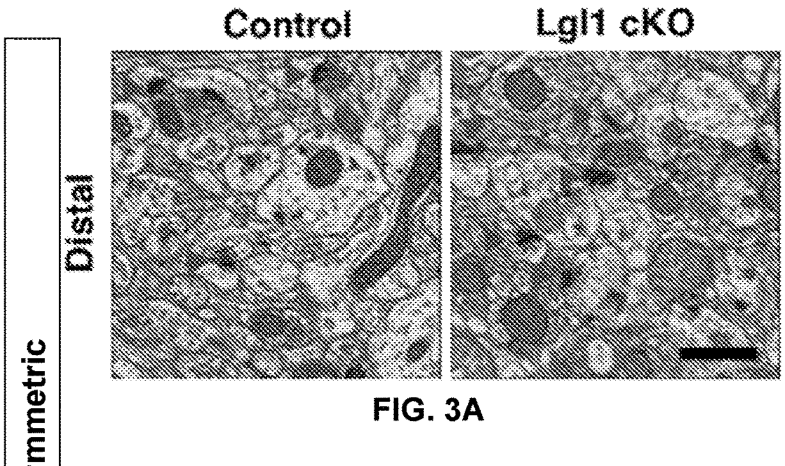
FIGS. 3A-3N are pictorial and graphical diagrams showing Increased Synapse Numbers, Altered AMPA/NMDA Ratio, and Impaired Plasticity in Adult Conditional Knockout of Lgl1.
Figure 3B:
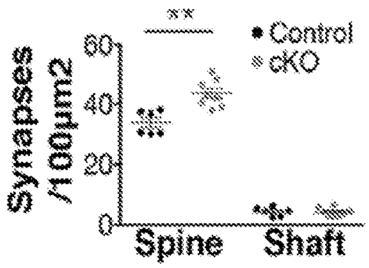
FIG. 3B shows quantification of asymmetric synapse density of the region described in FIG. 5A.
Figure 3C:
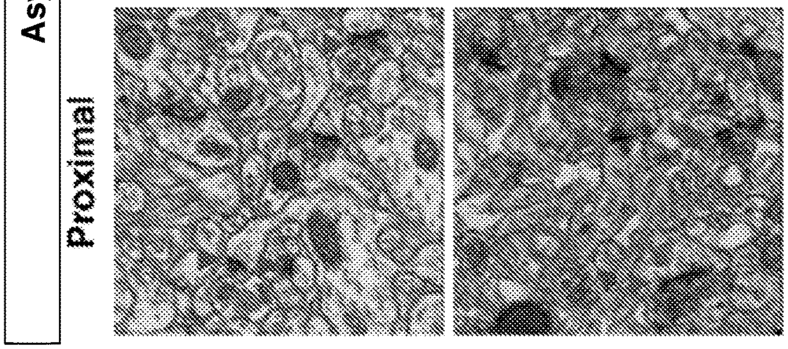
FIG. 3C shows electron micrographs of the SC 50 mm ventral to the CA1 pyramidal cell layer in 10-week-old animals.
Figure 3D:
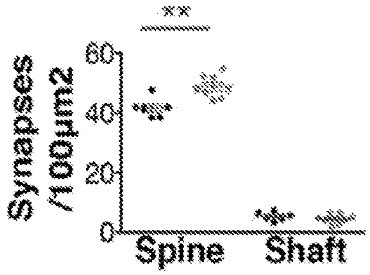
FIG. 3D shows quantification of asymmetric synapses in the proximal region.
Figure 3E:
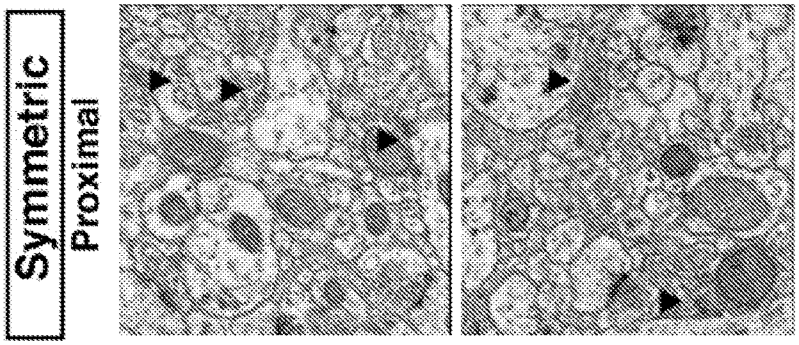
FIG. 3E shows micrographs showing symmetric synapses (black arrows) in the proximal region of the SC.
Figure 3F:
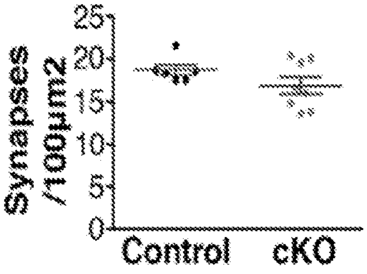
FIG. 3F shows quantification of symmetric synapses.
Figure 3G:
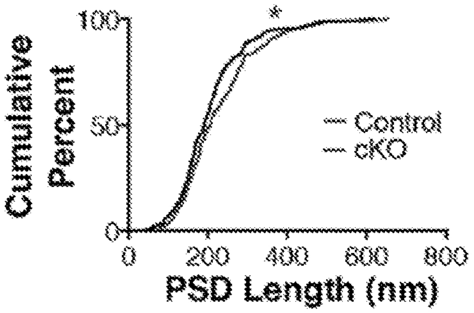
FIG. 3G shows quantification of cumulative frequency for postsynaptic density (PSD) length.
Figure 3H:
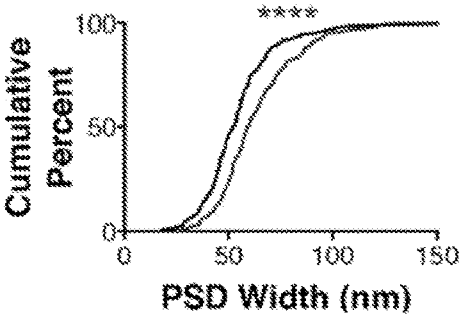
FIG. 3H shows quantification for PSD width.
Figure 3I:
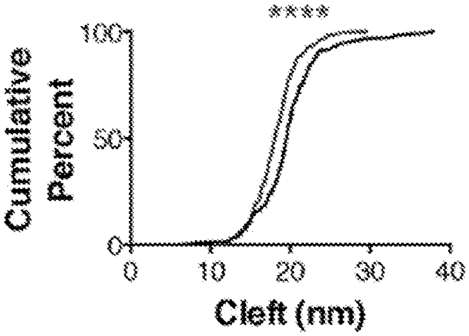
FIG. 3I shows quantification of synaptic cleft distance. n=180 Lgl1 control synapses, 242 Lgl1 cKO synapses.
Figure 3J:
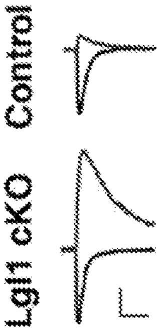
FIG. 3J shows representative traces of NMDAR current and combined AMPAR/NMDAR current from acute slices taken from 6-week-old control and Lgl1 cKO mice following Lgl1 deletion beginning at P28. Scale bar: 50 pA (vertical); 80 ms (horizontal).
Figure 3K:
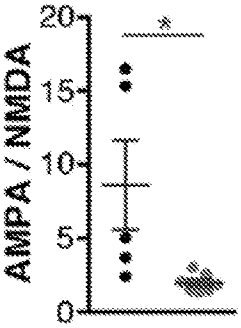
FIG. 3K shows quantification of the calculated ratio of AMPAR to NMDAR current: n=5 control, 7 Lgl1 cKO neurons.
Figure 3L:
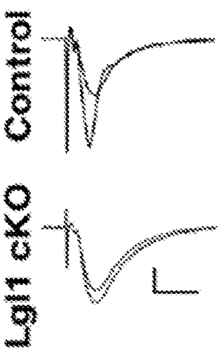
FIG. 3L shows representative traces of EPSPs before and after TBS stimulation was delivered to acute slices from control and Lgl1 cKO mice. Scale bar, 0.2 mV, 10 ms.
Figure 3M:
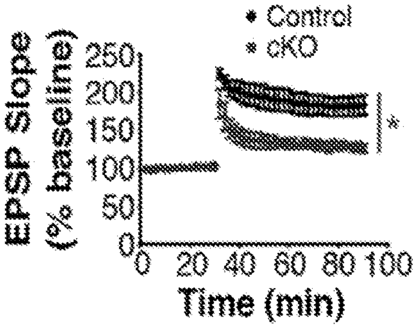
FIG. 3M shows quantification of EPSP slope before and after theta burst stimulation (TBS). N=5 Lgl1 control, 4 Lgl1 cKO.
Figure 3N:
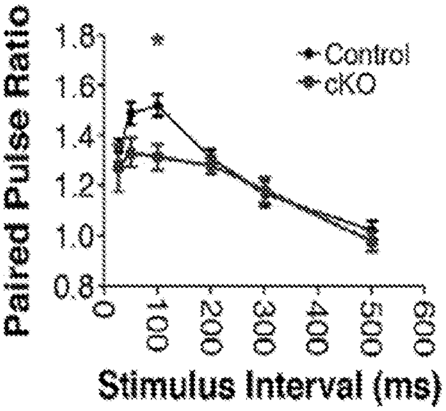

Therefore, loss of Lgl1 may lead to changes of MAGUKs and glutamate receptor compositions, such as the reduction of AMPA/NMDA ratio. Because the AMPA receptor level remains the same, the reduction in AMPA/NMDA ratio is likely caused by increased NMDA currents. This is somewhat surprising because more NMDAR is usually correlated with increased plasticity, and yet it was found that LTP was impaired. It should be noted that a decrease of paired-pulse ratio was also observed in Lgl1 cKO, suggesting that there may also be presynaptic defects (FIG. 3N). The Cre line used here in, SLICK-H, expresses CreERT2 in both CA3 and CA1 pyramidal neurons. Although Lgl1 was found to be present in the postsynaptic density (FIG. 1I), Lgl1 may also have a function on the presynaptic side. This reduction of paired-pulse ratio may contribute to the altered synaptic function.

Because Lgl1 is in the microdeletion region of SMS, four different approaches were used to delete Lgl1 to test the behavioral consequences, particularly those related to symptoms of SMS. In addition, a number of behavioral tests were performed. cKO of Lgl1 from P7 and P8 led to behavioral deficits, including hyperactivity, cognitive impairment, and social interaction, consistent with the autism-like symptoms in SMS. As SMS involves the microdeletion of one of the chromosomes, the $Lgl1^{+/-}$ were analyzed mice and it was found that $Lgl1^{+/-}$ mice had increased synapse numbers, impaired social interaction, and increased stereotyped repetitive behavior, suggesting that Lgl1 is a candidate gene that contributes to the autism-like symptoms of SMS with Lgl1 deletion. Repetitive behaviors involve the striatum, where $CreER^{T2}$ is not expressed in the SLICK-H line. Without being bound by theory, this may explain why repetitive behavior defects were only observed in $Lgl1^{+/-}$. There was a slowed habituation to the open field in $Lgl1^{+/-}$ and defects in novel object recognition. In summary, loss of both copies of Lgl1 locally or only one copy of Lgl1 globally could cause behavioral deficits related to a subset of autism-like symptoms of SMS. Interestingly, Lgl1 cKO and $Lgl1^{+/-}$ animals did not show an increase in grooming behavior during open-field observation or signs of excessive self-grooming while in their home cage that characterizes other ASD-like mouse models (Peça et al., 2011). Lgl1 appears to be important to maintaining proper synapse numbers and normal function of synapses even in adulthood as deleting Lgl1 at 6 weeks still lead to increase of synapse numbers and changes of synapse structure and function. Lgl1 may therefore be a key molecule required for synaptic plasticity in adulthood as cKO led to impairment of long-term potentiation. Therefore, the loss of Lgl1 in SMS may underlie the neurobiological basis of behavioral symptoms. These studies have also given rise to a mouse model ($Lgl1^{+/-}$ mice) for SMS for understanding disease mechanisms and development of treatment. Indeed, it was observed that blockade of NMDARs rescues social deficits, suggesting that NMDARs may be promising therapeutic targets for SMS with Lgl1 deletion.

Animals containing more than one transgenic construct and/or more than one transgene expression construct may be prepared in any of several ways. An exemplary manner of preparation is to generate a series of animals, each containing one of the desired transgenic phenotypes. Such animals are bred together through a series of crosses, backcrosses and selections, to ultimately generate a single animal containing all desired transgenic traits and/or expression constructs, where the animal is otherwise congenic (genetically identical) to the wild type except for the presence of the construct(s) and/or transgene(s).

Embryonic stem (ES) cells are typically selected for their ability to integrate into and become part of the germ line of a developing embryo so as to create germ line transmission of the transgene. Thus, any ES cell line that can do so is suitable for use herein. ES cells are generated and maintained using methods well known to the skilled artisan, such as those described by Doetschman et al. (1985) J. Embryol. Exp. Mol. Biol. 87:27-45). Any line of ES cells can be used, however, the line chosen is typically selected for the ability of the cells to integrate into and become part of the germ line of a developing embryo so as to create germ line transmission of the transgenic/knockout construct. Thus, any ES cell line that is believed to have this capability is suitable for use herein. One mouse strain that is typically used for production of ES cells, is the 129J strain. Another ES cell line is murine cell line D3 (American Type Culture Collection, catalog no. CKL 1934). Still another ES cell line is the WW6 cell line (Ioffe et al. (1995) PNAS 92:7357-7361). The cells are cultured and prepared for knockout construct insertion using methods well known to the skilled artisan, such as those set forth by Robertson in: Teratocarcinomas and Embryonic Stem Cells: A Practical Approach, E. J. Robertson, ed. IRL Press, Washington, D.C. (1987)); by Bradley et al. (1986) Current Topics in Devel. Biol. 20:357-371); and by Hogan et al. (Manipulating the Mouse Embryo: A Laboratory Manual, Cold Spring Harbor Laboratory Press, Cold Spring Harbor, N.Y. (1986)).

Introduction of the knock-out construct into ES cells may be accomplished using a variety of methods well-known in the art, including, for example, electroporation, microinjection, and calcium phosphate treatment. For introduction of the DNA sequence, the knock-out construct DNA is added to the ES cells under appropriate conditions for the insertion method chosen. If the cells are to be electroporated, the ES cells and construct DNA are exposed to an electric pulse using an electroporation machine (electroporator) and following the manufacturer's guidelines for use. After electroporation, the cells are allowed to recover under suitable incubation conditions. The cells are then screened for the presence of the knockout construct. Screening for cells which contain the transgene (homologous recombinants) may be done using a variety of methods. For example, as described herein, cells can be processed as needed to render DNA in them available for screening with specific probes by polymerase chain reaction (PCR).

Once appropriate ES cells are identified, they are introduced into an embryo using standard methods. They can be introduced using microinjection, for example. Embryos at the proper stage of development for integration of the ES cell to occur are obtained, such as by perfusion of the uterus of pregnant females. For example, mouse embryos at 3-4 days development can be obtained and injected with ES cells using a micropipet. After introduction of the ES cell into the embryo, the embryo is introduced into the uterus of a pseudopregnant female mouse. The stage of the pseudopregnancy is selected to enhance the chance of successful implantation. In mice, 2-3 days pseudopregnant females are appropriate.

Successful incorporation of ES cells into implanted embryos results in offspring termed chimeras. Chimeras capable of germline transmission of the mutant allele are identified by standard methods. Chimeras are bred and the resulting progeny are screened for the presence of the desired alteration (e.g., the modified recombinant Ryk allele). This may be done, for example, on the basis of coat color or by obtaining DNA from offspring (e.g., tail DNA) to assess for the transgene, using known methods (e.g., Southern analysis, dot blot analysis, PCR analysis). Transgene expression may also be assessed (e.g., to determine if a replacement construct is expressed) by known methods, such as northern analysis or PCR analysis. Southern hybridization or PCR analysis of progeny DNA (e.g., tail DNA) may be conducted to identify desired genotypes. A suitable technique for obtaining completely ES cell derived transgenic non-human organisms is described in WO 98/06834, incorporated herein by reference.

As mentioned above, the homologous recombination of the above described "knock-out" and/or "knock in" constructs is sometimes rare and such a construct can insert non-homologously into a random region of the genome where it has no effect on the gene which has been targeted for deletion, and where it can potentially recombine so as to disrupt another gene which was otherwise not intended to be altered. Such non-homologous recombination events can be selected against by modifying the above-mentioned targeting vectors so that they are flanked by negative selectable markers at either end (particularly through the use of the diphtheria toxin gene, thymidine kinase gene, the polypeptide product of which can be selected against in expressing cell lines in an appropriate tissue culture medium well known in the art—e.g., one containing a drug such as ganciclovir. Non-homologous recombination between the resulting targeting vector comprising the negative selectable marker and the genome will usually result in the stable integration of one or both of these negative selectable marker genes and hence cells which have undergone non-homologous recombination can be selected against by growth in the appropriate selective media (e.g., media containing a drug such as ganciclovir). Simultaneous selection for the positive selectable marker and against the negative selectable marker will result in a vast enrichment for clones in which the construct has recombined homologously at the locus of the gene intended to be mutated. The presence of the predicted chromosomal alteration at the targeted gene locus in the resulting stem cell line can be confirmed by means of Southern blot analytical techniques which are well known to those familiar in the art. Alternatively, PCR can be used.

Other methods of making transgenic animals are also generally known. See, for example, Manipulating the Mouse Embryo, (Cold Spring Harbor Laboratory Press, Cold Spring Harbor, N.Y., 1986). Recombinase dependent transgenic organisms can also be generated, e.g., by homologous recombination to insert target sequences, such that tissue specific and/or temporal control of inactivation of a Ryk gene can be controlled by recombinase sequences.

Thus, in another aspect, the invention provides a transgenic non-human mammal whose genome comprises a heterozygous or homozygous deletion, inactivation or knock-out of the Lgl1 gene and a heterozygous or homozygous deletion, inactivation or knock-out of PKC. In various embodiments, the transgenic non-human mammal is a mouse. In various embodiments, the genome of the mouse further comprises a heterozygous or homozygous deletion, inactivation or knock-out of PKCι/λ and PKCξ isoforms.

As demonstrated herein, using an NMDA antagonist, such as ketamine, memantine, or dizocilpine (MK-801), at a subanesthetic dose, can also alleviate social interaction deficits. Through block of NMDA receptors (NMDAR), such NMDA antagonists may mitigate abnormal activity patterns arising from over connectivity and increased NMDAR activity, which could underlie the behavioral deficits observed in Lgl1 cKO and Lgl1$^{+/-}$ animals. Understanding the function of Lgl1 may also give rise to means to rescue symptoms in SMS in the future by expressing Lgl1 or its downstream effectors or by inhibiting the downstream signaling that is disinhibited due to the loss of Lgl1.

Accordingly, the invention provides a method for reducing or preventing lethal giant larvae (Lgl1) induced increase in synapses in a population of neurons, comprising contacting the neurons with a subanesthetic amount of an N-methyl-D-aspartate (NMDA) receptor antagonist. In various embodiments, the NMDA receptor antagonist increases the AMPA/NMDA ratio in the neurons. In various embodiments, the NMDA receptor antagonist is selected from the group consisting of ketamine, memantine, dizocilpine (MK-801), dextromethorphan (DXM), phencyclidine (PCP), methoxetamine (MXE), nitrous oxide ($N_2O$), and any combination thereof.

In various embodiments, the method may also include contacting the population of neurons with an atypical protein kinase c (aPKC) inhibitor. In various embodiments, the aPKC inhibitor is a small molecule compound, a nucleic acid molecule or polypeptide. In various embodiments, the aPKC inhibitor is an antibody or antigen binding fragment that binds to one or more of protein kinase c ξ (aPKCξ) and protein kinase c ι/λ (aPKCι/λ) isoforms. In various embodiments, the aPKC inhibitor reduces or inhibits expression of aPKCξ and aPKCι/λ, in the neurons.

In various embodiments, the method may also include contacting the population of neurons with a Lgl1 agonist. In various embodiments, the Lgl1 agonist is a small molecule compound, a nucleic acid molecule or polypeptide that induces expression of Lgl1. In various embodiments, the Lgl1 agonist is a small molecule compound, a nucleic acid molecule or polypeptide that induces a signaling pathway that induces expression of Lgl1.

In various embodiments, the population of neurons is in a subject, and wherein the step of contacting is performed by administering NMDA receptor antagonist and/or the aPKC inhibitor to the subject. In various embodiments, the population of neurons is in the brain of the subject. In various embodiments, the subject has or is at risk of developing a neurodegenerative disease or behavioral disorder, such as Smith-Magenis Syndrome (SMS), autism, or attention deficit hyperactivity disorder (ADHD). In various embodiments, the NMDA receptor antagonist alleviates social interaction deficits associated with the behavioral disorder.

In another aspect, the invention provides a method of managing, preventing, or treating a neurodegenerative disease or behavioral disorder in a subject, comprising administering to the subject a subanesthetic amount of an N-methyl-D-aspartate (NMDA) receptor antagonist. In various embodiments, the NMDA receptor antagonist increases the AMPA/NMDA ratio in the neurons. In various embodiments, the NMDA receptor antagonist is selected from the group consisting of ketamine, memantine, dizocilpine (MK-801), dextromethorphan (DXM), phencyclidine (PCP), methoxetamine (MXE), nitrous oxide ($N_2O$), and any combination thereof.

In various embodiments, the method may also include administering to the subject an atypical protein kinase c (aPKC) inhibitor. In various embodiments, the aPKC inhibitor is a small molecule compound, a nucleic acid molecule or polypeptide. In various embodiments, the aPKC inhibitor is an antibody or antigen binding fragment that binds to one or more of protein kinase c ξ(aPKCξ) and protein kinase c ι/λ (aPKCι/λ) isoforms. In various embodiments, the aPKC inhibitor reduces or inhibits expression of aPKCξ and aPKCι/λ in the neurons. In various embodiments, the method may also include administering to the subject a Lgl1 agonist. In various embodiments, the Lgl1 agonist is a small molecule compound, a nucleic acid molecule or polypeptide that induces expression of Lgl1. In various embodiments, the Lgl1 agonist is a small molecule compound, a nucleic acid molecule or polypeptide that induces a signaling pathway that induces expression of Lgl1.

In various embodiments, the number of synapses in a population of neurons in the subject is decreased. In various embodiments, the synapses are excitatory synapses. In various embodiments, the synapses are glutamatergic synapses. In various embodiments, the NMDA receptor antagonist alleviates social interaction deficits associated with the behavioral disorder. In various embodiments, the population of neurons comprises a cerebellar granule neuron, a dorsal root ganglion neuron, a cortical neuron, a sympathetic neuron, or a hippocampal neuron.

In another aspect, the invention provides a method of treating behavioral disorders, such as SMS, through modulation of Lgl1. In various embodiments, the method includes administering to a subject in need thereof an N-methyl-D-aspartate (NMDA) receptor antagonist, such as ketamine, at a subanesthetic dose, thereby alleviating social interaction deficits associated with the behavioral disorder. By blocking NMDA receptors, ketamine may mitigate abnormal activity patterns arising from over connectivity and increased NMDAR activity. In various embodiments, the method may further include administering to the subject an atypical protein kinase c (aPKC) inhibitor alone or in combination with a Lgl1 agonist. Exemplary NMDA receptor antagonists useful in the methods provided herein include, but are not limited to, as ketamine, memantine (NAMZARIC®), dizocilpine (MK-801), dextromethorphan (DXM), phencyclidine (PCP), methoxetamine (MXE), and nitrous oxide ($N_2O$).

In yet another aspect, the invention provides a method of selecting a modulator of synapse formation or a modulator of synapse maintenance. In various embodiments, the method includes providing a population of neurons having a heterozygous or homozygous deletion, inactivation or knock-out of Lgl1; measuring a first level of the AMPA/NMDA ratio in the neurons; contacting a candidate agent with the population of neurons; measuring a second level of the AMPA/NMDA ratio in the neurons; and selecting the candidate agent as the modulator if the second level of association is different from the first level of association. In various embodiments, the candidate agent comprises a small-molecule compound, a nucleic acid, or a peptide. In various embodiments, the nucleic acid is a microRNA, siRNA or CRISPR-based gene editing construct. In various embodiments, the candidate agent is an antibody or antigen binding fragment thereof. In various embodiments, the method is performed in the presence of aPKC. In various embodiments, the population of the cells is in a non-human mammal, and wherein the step of contacting is performed by administering the candidate agent to the non-human mammal.

Figure 8A:
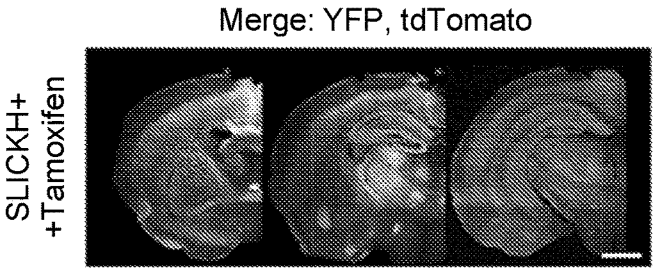
FIGS. 8A-8I are pictorial and graphical diagrams showing assessment of conditional deletion and characterization of current kinetics.
Figure 8B:
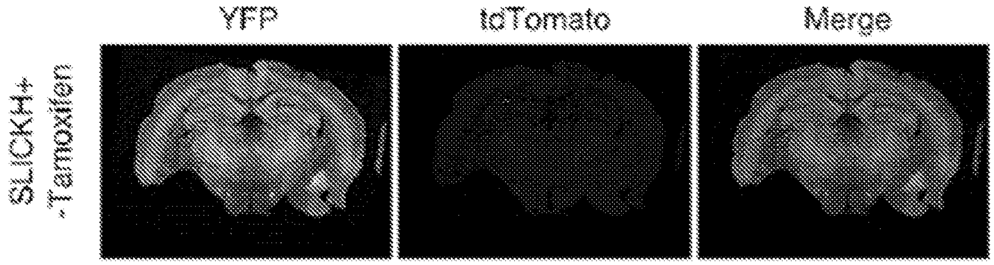
Figure 8C:
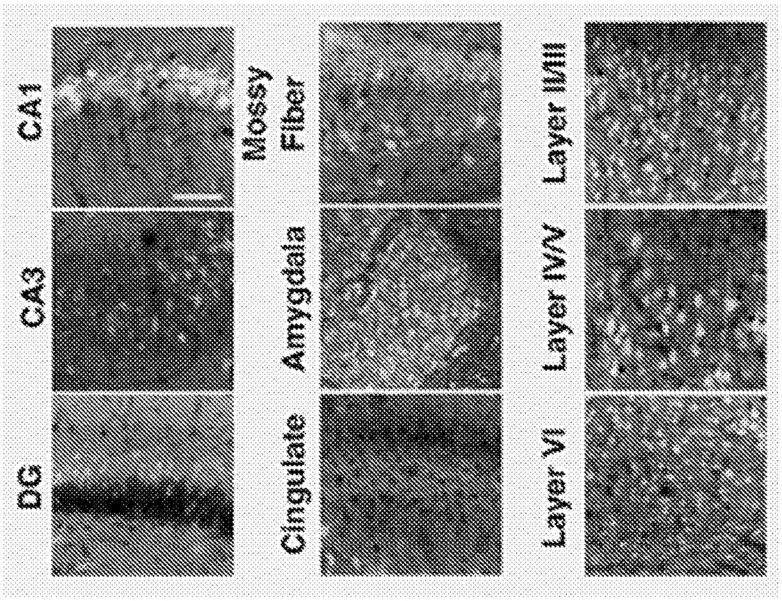

Increased Glutamatergic Synapse Numbers and Reduced AMPA/NMDA Ratio in Lgl1 Conditional Knockout In Vivo Glutamatergic synapse formation starts shortly after birth. Lgl1 has roles in earlier stages of development, including neurogenesis. To avoid early developmental defects, Lgl1 was conditionally knocked out in hippocampal pyramidal neurons from postnatal day 7 (P7) using an inducible Cre line, SLICK-H (FIGS. 8A-8C) (Heimer-McGinn and Young, 2011). Tamoxifen was injected intraperitoneally on P7 and postnatal day 8 (P8) and animals were sacrificed and perfused on postnatal day 14 (P14) for electron microscopy. Asymmetric and symmetric synapses were counted in the stratum radiatum. Images were taken 150-200 μm from the CA1 cell body layer in brain slices. A 28.7% increase was observed in the density of asymmetric (excitatory) synapse that are formed on dendritic spines (FIG. 1A). Axo-dendritic synapses showed no change in density. No significant change was observed in symmetric (inhibitory) synapse density in these slices.

Figure 1B:
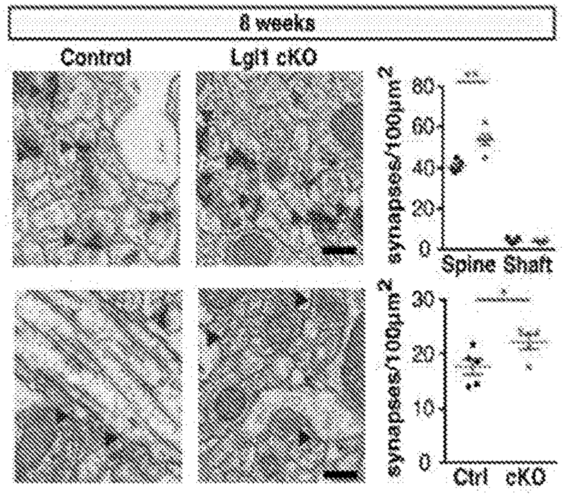
Figure 8D:
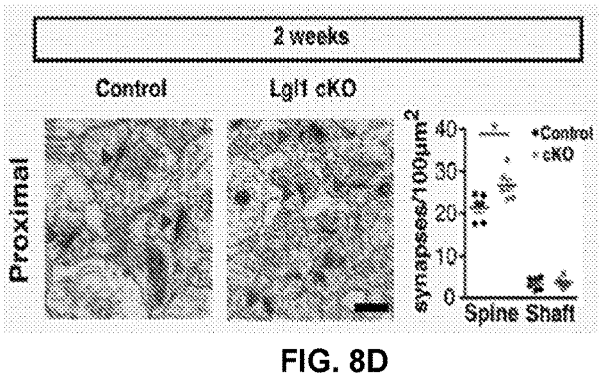
Figure 8E:
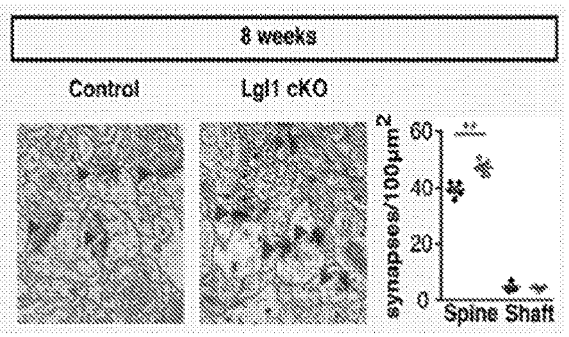

In order to determine whether the increased synapses persist, slices from 8-week old adult mice that had tamoxifen injection at P7 and P8 were fixed. In these animals, an increase of 31.8% in asymmetric synapse density 150-200 μm from the CA1 cell body layer was observed (FIG. 1B). In contrast to juvenile animals, adult animals show a statistically significant 25.5% increase in density of symmetric synapses in the region 50 μm from the CA1 cell layer. The delay in the increase of symmetric synapses suggests that it is not directly caused by the loss of function of Lgl1, but possibly by a homeostatic response of the hippocampal circuitry. The number of asymmetric synapses in the region 50 μm from the CA1 cell layer also showed an increase (FIGS. 8D-8E).

Figure 1C:
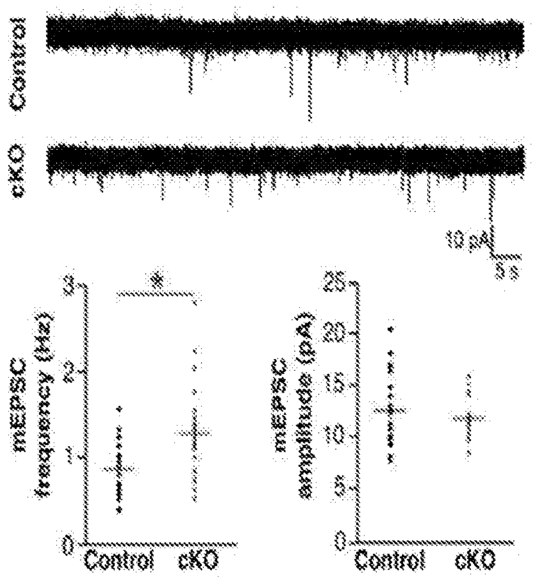
Figure 1D:
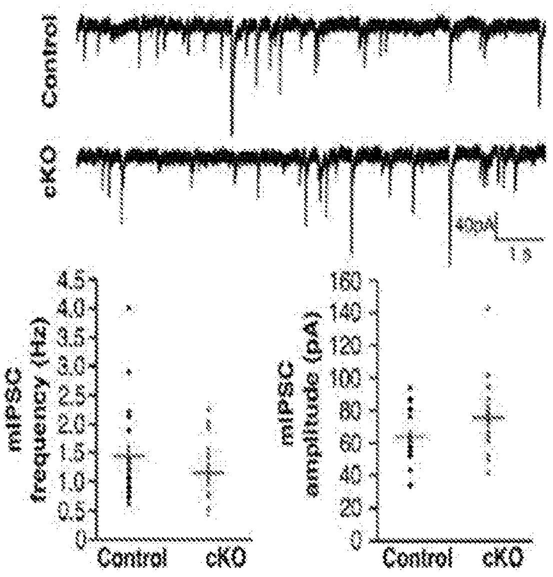
Figure 8F:
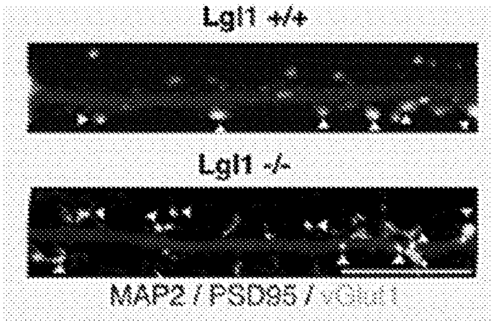
Figure 8G:
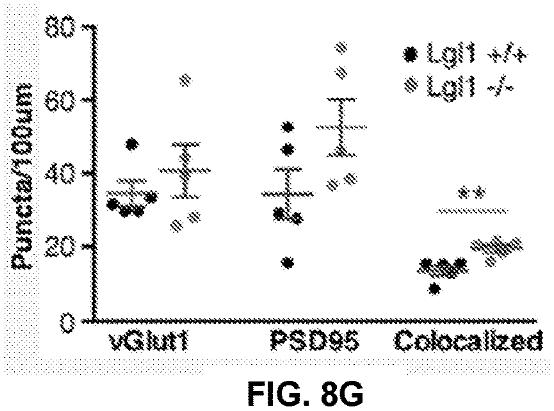
Figure 8H:
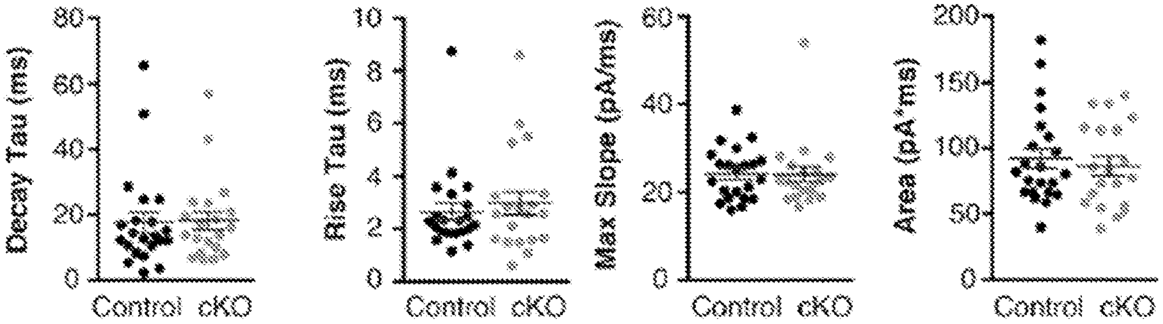
Figure 8I:
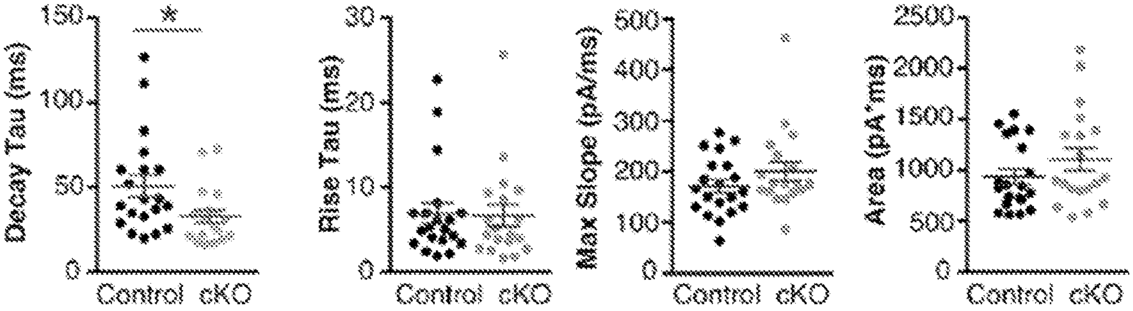

To assess the function of the increased synapses, miniature excitatory postsynaptic currents (mEPSCs) and miniature inhibitory postsynaptic currents (mIPSCs) were recorded from acute brain slices from P14 and 15 control and Lgl1 cKO animals. Quantification of frequency and amplitude of synaptic currents indicates that mEPSC frequency is increased by 38%, whereas amplitude was not changed significantly, indicating an increase in synapse number, but similar AMPA-R composition (FIG. 1C). No significant changes were observed in mIPSC currents (FIG. 1D), consistent with the electron microscopy data provided herein. Consistent with this, cultured hippocampal neurons from mice carrying germline deletion of Lgl1 also show increased colocalization between PSD95 and vGlutl puncta at 14 days in vitro (DIV) (FIGS. 8F and 8G). mEPSC kinetics did not show significant changes (FIG. 8H), whereas mIPSC kinetics only showed a significant decrease in decay time constant, but not in other measures (FIG. 8I).

Figure 1E:
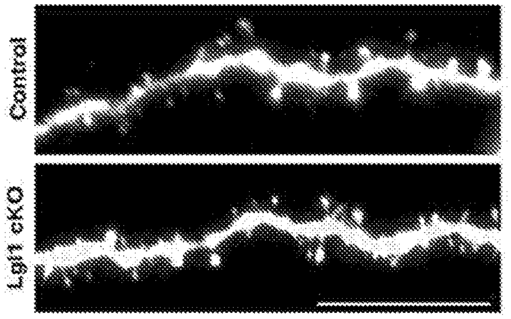
Figure 1F:
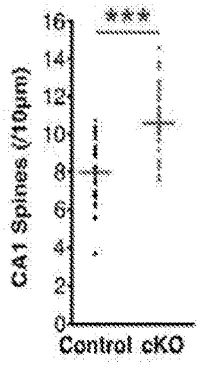
Figure 1G:
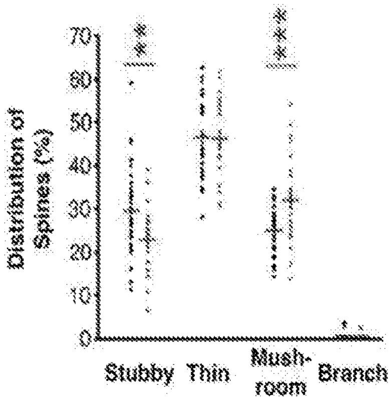

To determine whether dendritic spine density was affected, neurons from fixed brain sections were filled with Alexa555 dye to visualize spines in yellow fluorescent protein (YFP)-positive CA1 pyramidal neurons (FIG. 1E). It was found that overall spine density was indeed increased by 38% in Lgl1 cKO mice (FIG. 1F). The morphology of spines at P14 was also characterized. Compared with control, Lgl1 cKO mice showed more mushroom spines and a reduced proportion of stubby spines (FIG. 1G). Since mushroom spines represent stabilized synapses and thin spines are unstable, this suggests that Lgl1 conditional knockout (cKO) led to functionally hyperconnected circuits.

Figure 1H:
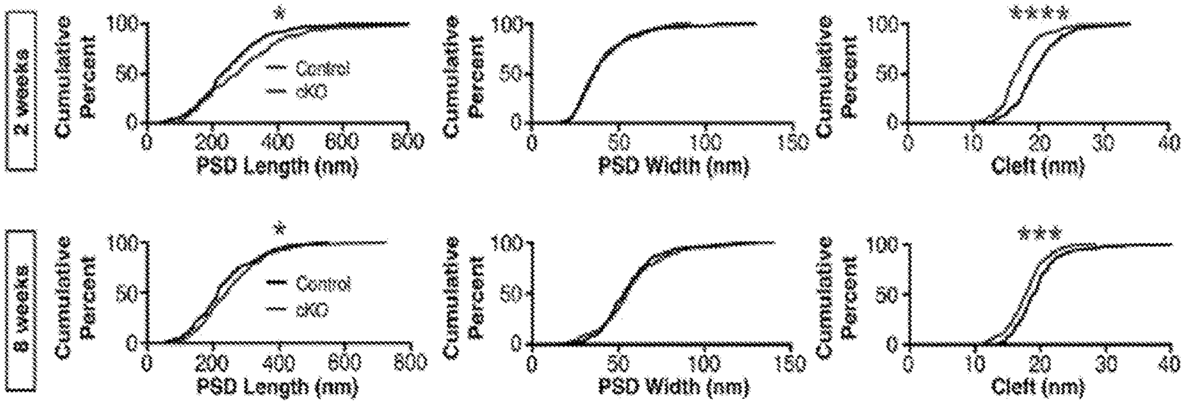
Figure 1I:
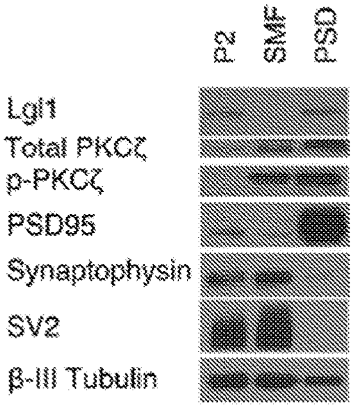
Figure 1J:
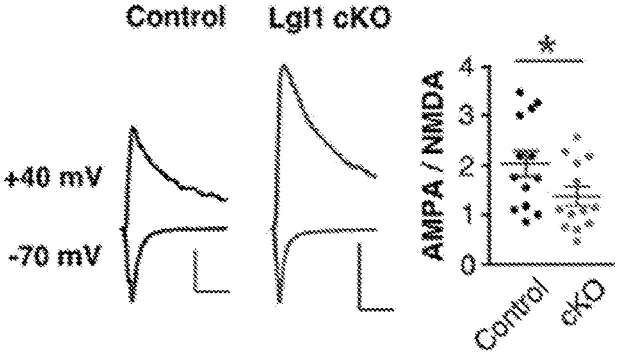

Consistent with this, the ultrastructure was then quantified from the electron micrographs and it was found that the length of postsynaptic density (PSD) was increased and the gap of synaptic cleft was reduced at P14 and at age 8 weeks (FIG. 1H). As Lgl1 interacts with the MAGUK proteins, the subcellular localization was determined, and it was found that Lgl1 was present in the postsynaptic density (FIG. 1I). The AMPA/NMDA ratio was also measured, and it was found that the ratio is decreased in the Lgl1 cKO, suggesting altered glutamate receptor trafficking or function (FIG. 1J).

Lgl1 Negatively Regulates Synapse Number by Inhibiting the Atypical PKCs

Figure 9A:
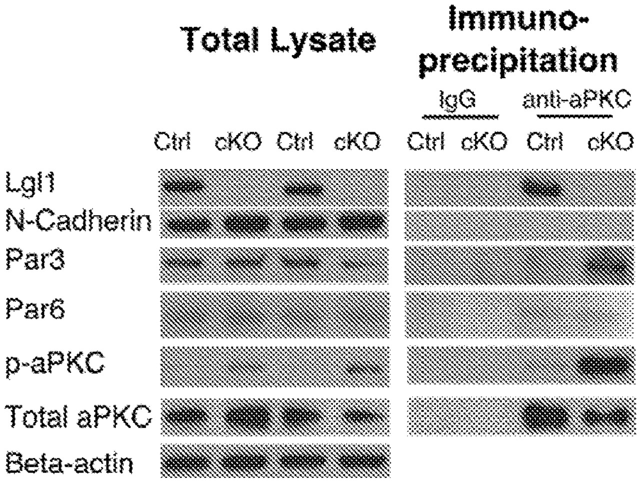
FIGS. 9A-9C are pictorial and graphical diagrams showing atypical PKC overactivation following Lgl1 conditional deletion and synapse quantification in aPKC dcKO.

As Lgl1 and aPKC antagonize each other in cell polarity signaling, it was considered that Lgl1 may regulate synapse formation by inhibiting the aPKCs. To validate whether Lgl1 also inhibits the aPKCs in neurons, their interaction in neural progenitor cells from E11.5 mouse telencephalon was tested. Lgl1 cKO and control cells were generated by treatment of cultures with AD5-CMV-Cre and Ad5-CMV-GFP adenoviruses (Vector Development Laboratory, Baylor College of Medicine), respectively, and verified that Lgl1 protein was completely lost in the cKO (FIG. 9A). It was then tested whether aPKC activity, as evident by association with Par3, was increased in Lgl1 cKO. Activated aPKC (phosphorylated at T555) and aPKC interaction with Par3 were found to be strongly increased in Lgl1 cKO, confirming the increase of apical signaling and decrease of basal-lateral signaling.

Figure 2A:
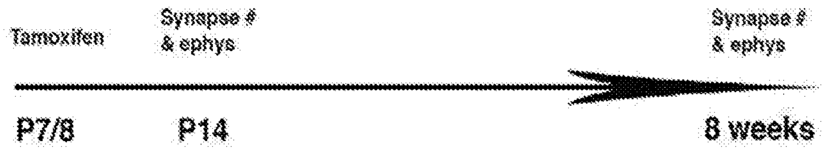
FIGS. 2A-2G are pictorial and graphical diagrams showing that Lgl1 inhibits synapse formation by inhibiting aPKC and promotes the expression of Vangl2.
Figure 2A:
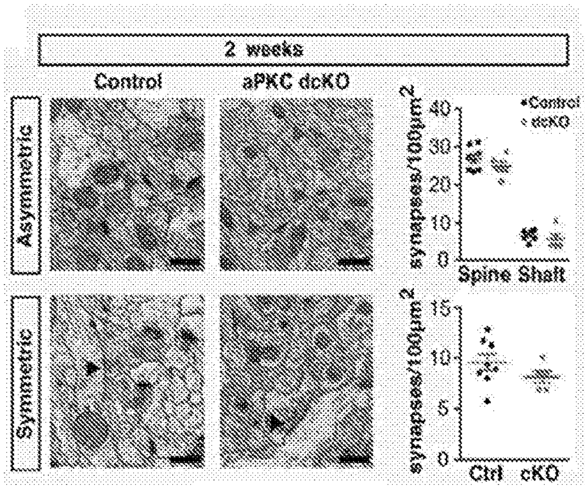
Figure 2B:
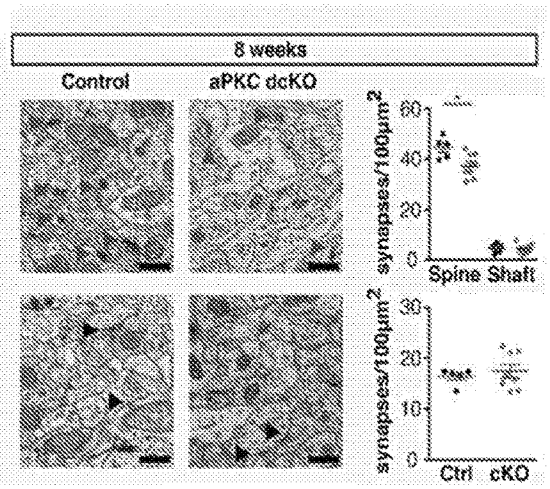
Figure 2C:
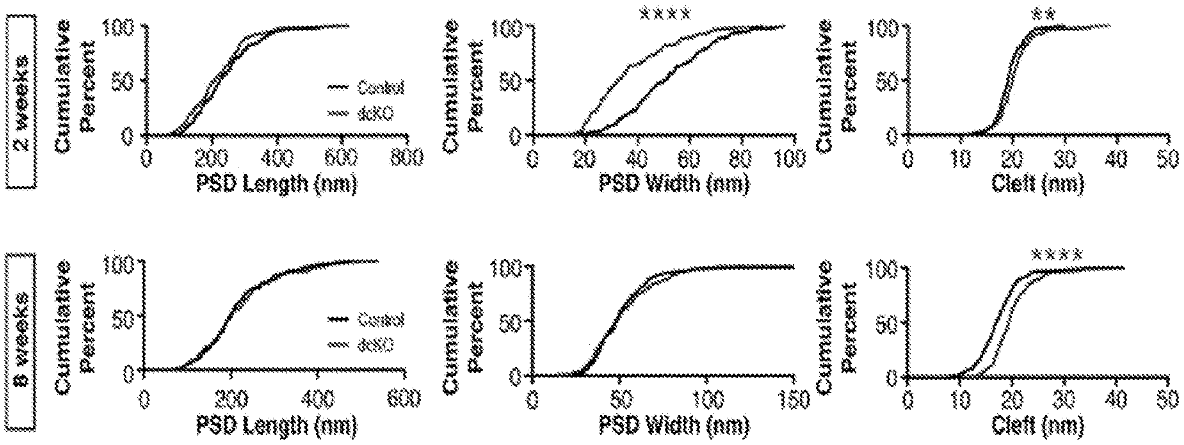
Figure 9B:
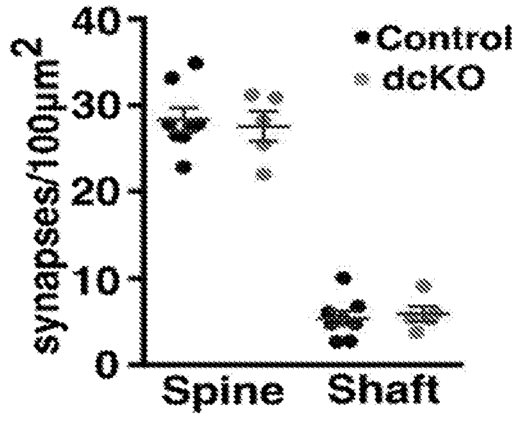
Figure 9C:
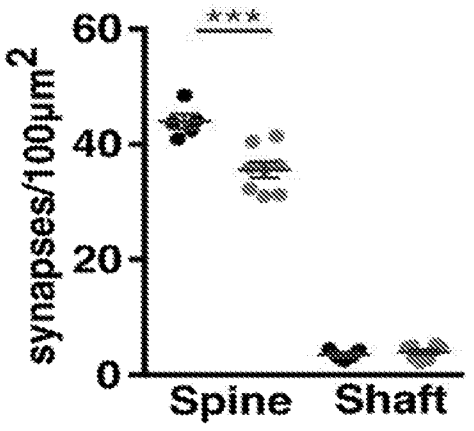

There are two isoforms of aPKCs in mice. Thus, the same strategy of tamoxifen-induced deletion of aPKCs using SLICK-H was used to delete both isoforms of aPKCs, PKCι/λ and PKCξ, to eliminate the possibility of compensation. Following this deletion, asymmetric and symmetric synapses were counted from the schaffer collateral 150 μm from the CA1 cell layer of 2- and 8-week-old animals. At 2 weeks, no significant difference was observed in the number of asymmetric or symmetric synapses (FIG. 2A). However, at 8 weeks, there was a significant decrease (−16.1%) in the number of asymmetric synapses (FIG. 2B). In the proximal region 50 mm from the CA1 cell body layer, a significant decrease was also observed at 8 weeks, but not at 2 weeks (FIGS. 9B and 9C). Therefore, aPKC is not essential for initial glutamatergic synapse formation but is required for their stability and maintenance. The ultrastructure was then analyzed, and it was found that the PSD width was reduced at 2 weeks, that the synaptic cleft was increased at 2 weeks, and that the magnitude of this change increased at 8 weeks (FIG. 2C). This suggests that aPKC is likely important for the stability of synapses, the opposite of Lgl1 (FIG. 1H).

Figure 2D:
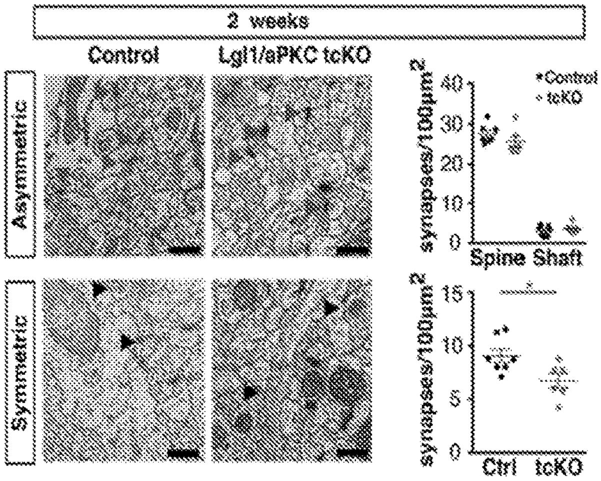
Figure 2E:
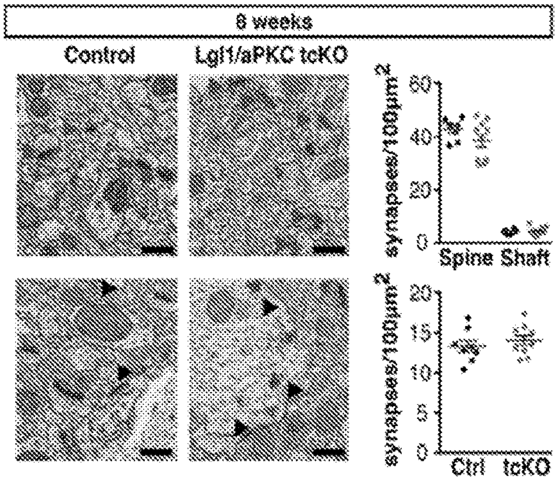
Figure 10A:
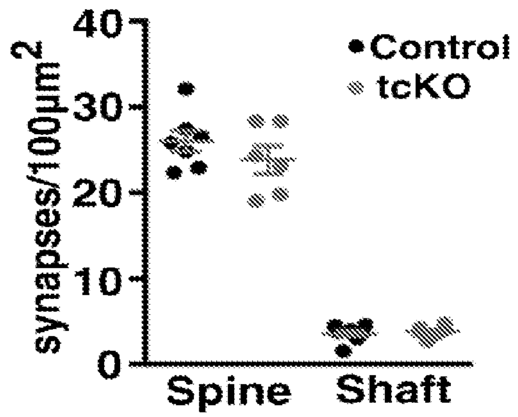
FIGS. 10A and 10B are graphical diagrams showing synapse quantification in Lgl1:PKCι/λ: PKCλ tcKO.
Figure 10B:
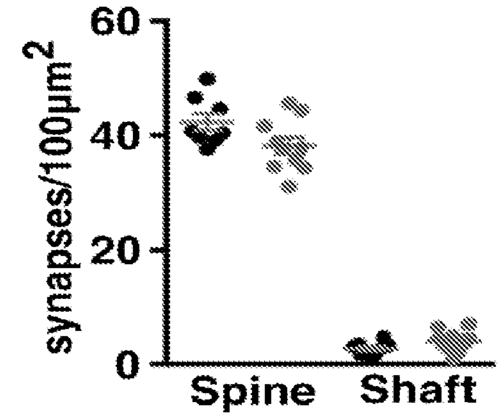

It was then asked whether simultaneous deletion of Lgl1, PKCι/λ and PKCξ might lead to mitigation of the effects observed in the Lgl1 conditional deletion experiments. In 2-week-old Lgl1:PKCι/λ: PKCξ tcKO animals, no significant change in asymmetric synapse number was observed, suggesting that the increase of synapse numbers in Lgl1 cKO may be partly due to the increase of aPKC activity (FIG. 2D). However, a significant decrease (−25.9%) in the number of symmetric synapses was observed. In 8-week-old Lgl1:PKCι/λ: PKCξ tcKO animals, no significant change in asymmetric or symmetric synapse number was observed (FIG. 2E). No significant difference in asymmetric synapse density was observed in the proximal region at 2 and 8 weeks (FIGS. 10A and 10B). Therefore, Lgl1 may negatively regulate glutamatergic synapse numbers by inhibiting aPKC, which is required for the stability and maintenance of glutamatergic synapses.

Figure 2F:
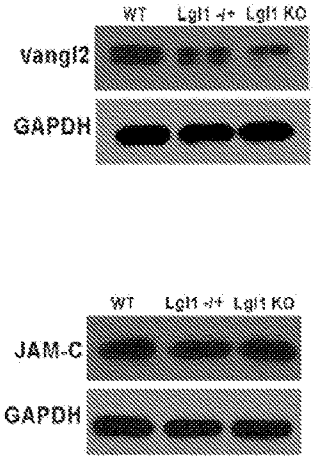
Figure 2G:
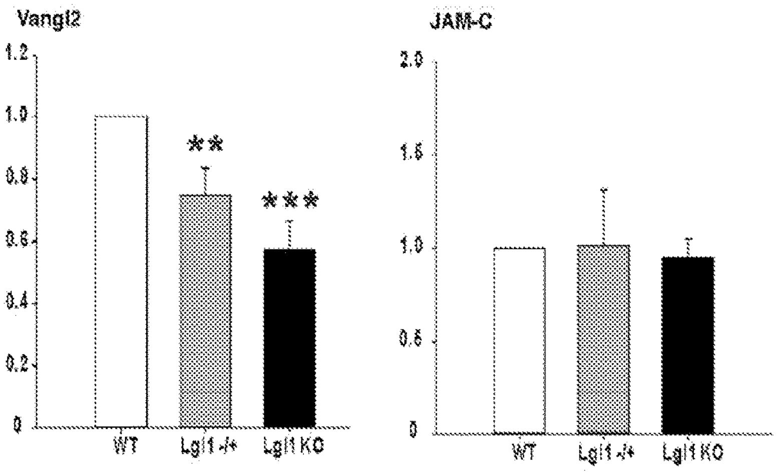

Because PCP proteins regulate synapse formation and apical-basal polarity signaling regulates the localization PCP signaling components, it was tested whether Lgl1 may regulate PCP components using synaptosome fractionation. The SLICK-H line (inducible Cre) expresses Cre in only 60% of pyramidal neurons at P7. Therefore, neurons were cultured from Lgl1 KOs, heterozygotes, and wild-type, and the synaptosome fractions extracted. It was found that Vangl2 protein levels are decreased in the P2 fractions of $Lgl1^{+/-}$ and $Lgl1^{-/-}$ compared with that of the wild-type (FIG. 2F), whereas the levels of an adhesion molecule Jam-C were not affected (FIG. 2G). This is consistent with the inhibitory function of Vangl2 in glutamatergic synapse formation.

Lgl1 Controls Glutamatergic Synapse Number and is Required for Synaptic Plasticity in Adulthood Because Lgl1 is highly expressed in the adult central nervous system, including the hippocampus, the role of Lgl1 was characterized in the adult brain. By early adulthood at 6 weeks of age, synapse formation has slowed considerably in the rodent hippocampus compared to postnatal development (Wang et al., 2007). Lgl1 was conditionally knocked out by injecting tamoxifen at 6 weeks after birth in SLICK-H animals. Electron microscopy was then used to assess the density of asymmetric and symmetric synapses in the schaffer collateral in 10-week-old animals. Asymmetric synapse density in the region 150-200 μm distal to the CA1 cell body layer was again increased by 28.6% on the dendritic spines (FIGS. 3A and 3B). A similar increase was observed in the proximal region 50 μm from the CA1 cell layer (FIGS. 3C and 3D). Symmetric synapses were again unaffected (FIGS. 3E and 3F). In addition, synapse ultrastructure was altered in the adult deletion of Lgl1, with longer and wider PSDs (FIGS. 3G and 3H) and smaller synaptic clefts (FIG. 3I), possibly as a result of altered biochemical makeup of synapses. Patch clamping was performed with P42 slices to assess the synaptic receptor expression from animals with Lgl1 deleted beginning at P28. A severe reduction in the AMPA/NMDA ratio was observed in neurons from Lgl1 cKO mice (FIGS. 3J and 3K), much greater than was observed at P14 following deletion of Lgl1 at P7/P8. These results suggest that Lgl1 is also required for control of synapse number and quality in adulthood.

Synaptic plasticity was tested using hippocampal slices from 10-week old mice following conditional Lgl1 deletion at 6 weeks of age. Slices from Lgl1 cKO animals showed impaired long-term potentiation (LTP) induction in response to theta burst stimulation (TBS) (FIGS. 3L-3M). In addition, slices from Lgl1 cKO mice showed impaired paired-pulse facilitation when stimuli were separated by 100 ms (FIG. 3N), indicating altered synaptic release.

Lgl1 cKO Mice Showed Behavioral Deficits

Figure 4A:
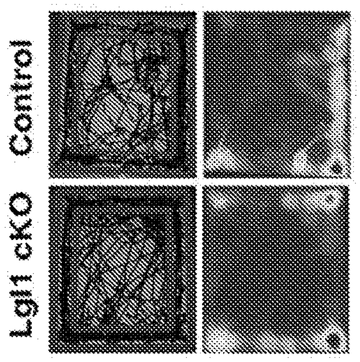
FIGS. 4A-4P pictorial and graphical diagrams showing that Lgl1 deletion at P7 produced a subset of SMS-like behavioral phenotypes.
Figure 4B:
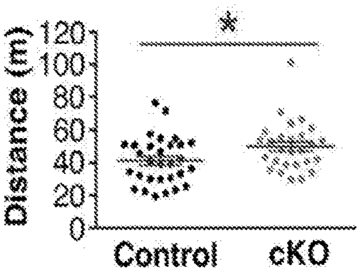
FIG. 4B shows quantification of distance traveled during the test. N=30 control, 27 Lgl1 cKO.
Figure 4C:
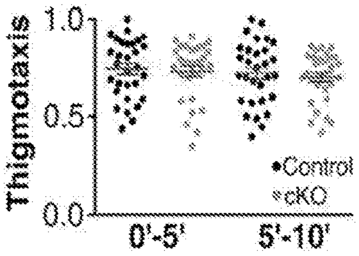
FIG. 4C shows quantification of time spent in the outer region of the field (thigmotaxis) during the first and second 5-minute periods.
Figure 11A:
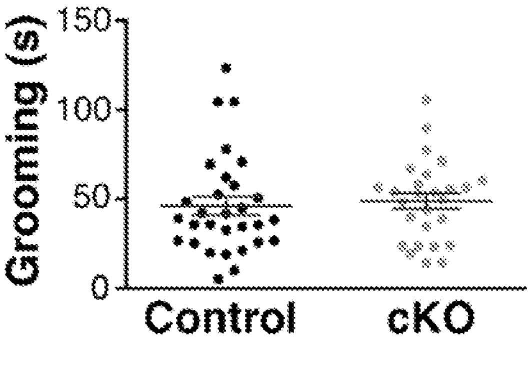
FIGS. 11A-11G are graphical diagrams showing additional behavioral characterization of Lgl1 deletion at day P7.
Figure 11B:
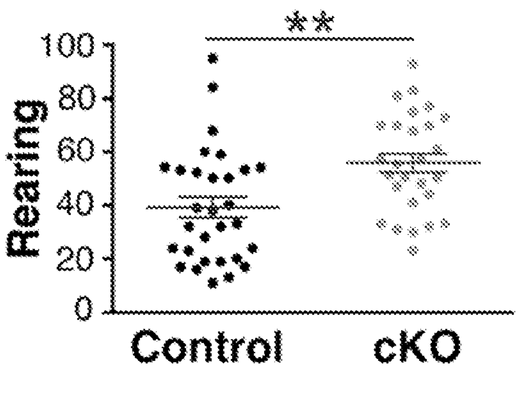

Lgl1 is frequently deleted in Smith-Magenis Syndrome (SMS) and the genes responsible for the behavioral symptoms of SMS have not been well understood. A number of behavioral tests were therefore performed to assess whether deletion of Lgl1 in pyramidal neurons may contribute to the behavioral deficits. Locomotor activity and exploratory behavior was assessed using an open field test (FIG. 4A; Gould et al., 2009). Lgl1 cKO animals showed increased locomotor activity, traveling 20% further during the 10-min test than control mice (FIG. 4B). No significant changes were observed in thigmotaxis, the preference for the outside of the field versus the center region (FIG. 4C). Animals did not show a difference in the amount of time spent self-grooming during the open field test (FIG. 11A), but showed a significant increase in rearing activity, an exploratory behavior (FIG. 11B).

Figure 4D:
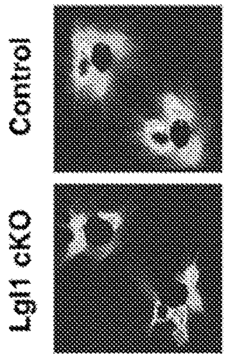
FIG. 4D shows a representative heatmap and FIG. 4E shows quantification of animal preference for objects during the sample phase of the novel object recognition (NOR) test. N=23 control, 19 Lgl1 cKO animals.
Figure 4E:
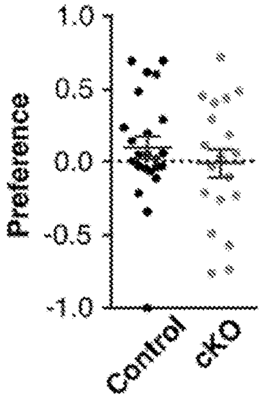
Figure 4F:
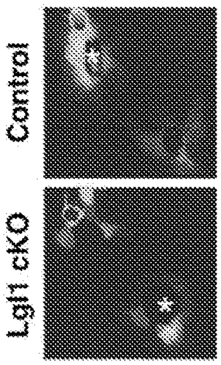
FIG. 4F shows a representative heatmap and FIG. 4G shows quantification of animal preference for objects during the test phase of the novel object recognition (NOR) test. White asterisk denotes location of the novel object.
Figure 4G:
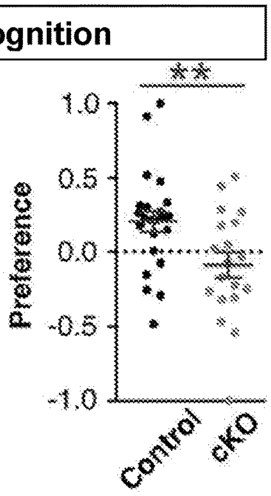

To assess cognitive function following conditional Lgl1 deletion, the Lgl1 cKO crossed with SLICK-H was tested in the novel object recognition (NOR) paradigm. The NOR test assesses whether an animal can distinguish a novel object from a previously explored familiar object. A preference index from each animal was calculated by subtracting the familiar object interaction time from the novel exploration time and normalizing to the total exploration time ((novel-familiar)/(novel+familiar)). During the sample phase, when both objects were novel, animals showed no preference and would randomly explore both objects (FIGS. 4D and 4E). When a novel object was introduced after a 2-min delay, control animals showed a strong preference for the novel object, whereas Lgl1 cKO animals continued to explore randomly and maintain a preference index close to zero (FIGS. 4F and 4G).

Figure 4H:
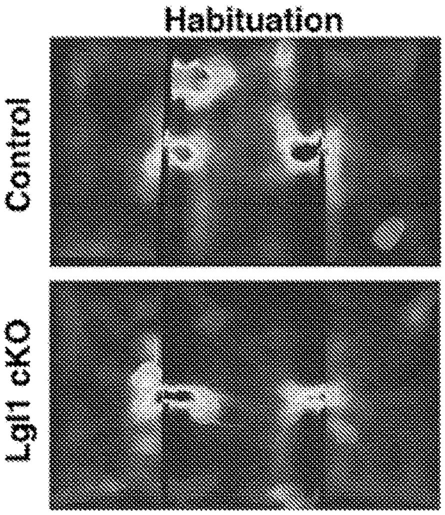
FIG. 4H shows representative heatmaps from the habituation period of the social interaction (SI) test.
Figure 4I:
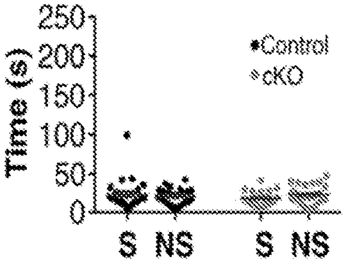
FIG. 4I shows quantification of time spent in and FIG. 4J shows preference for regions of interest (ROIs) representing future location of novel mice and objects. N=25 control, 24 Lgl1 cKO animals.
Figure 4J:
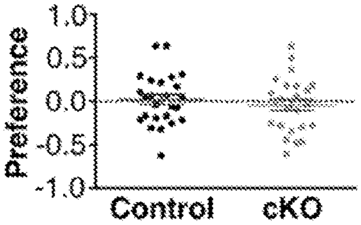
Figure 4K:
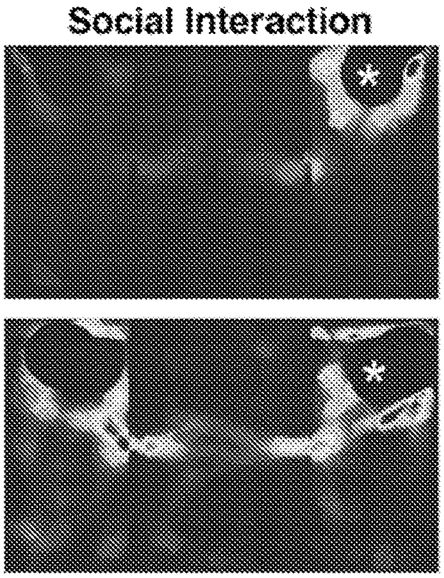
FIG. 4K shows representative heatmaps during the social interaction phase of the SI test. White asterisk denotes location of the novel mouse. Opposite chamber contains the object.
Figure 4L:
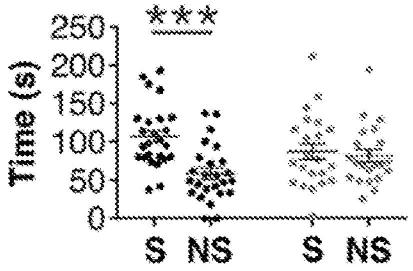
FIG. 4L shows quantification of time spent in and FIG. 4M shows preference for ROIs containing either the novel mouse or novel object. Positive value indicates preference for the novel mouse. N=25 control, 22 Lgl1 cKO animals.
Figure 4M:
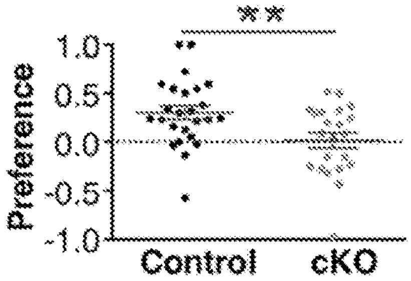
Figure 4N:
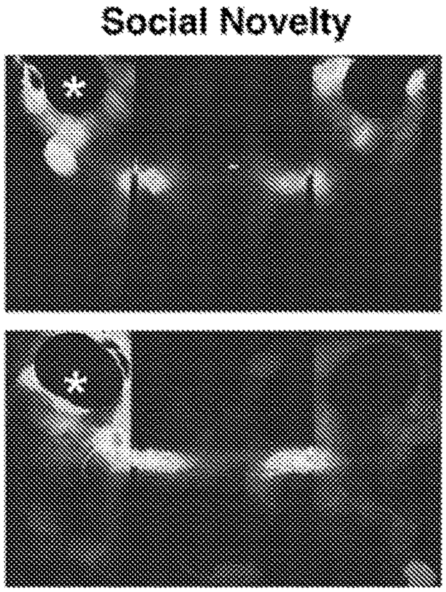
FIG. 4N shows representative heatmaps during the social novelty phase of the SI test. White asterisk denotes location of the novel mouse. Opposite chamber contains the previously explored mouse.
Figure 4O:
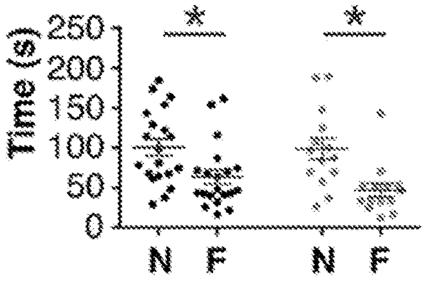
FIG. 4O shows quantification of time spent interacting with and FIG. 4P shows preference for target mice during the social novelty phase. Positive value indicates preference for the novel mouse. N=20 control, 14 Lgl1 cKO animals. NS, nonsocial; S, social. *p<0.05; **p<0.01
Figure 4P:
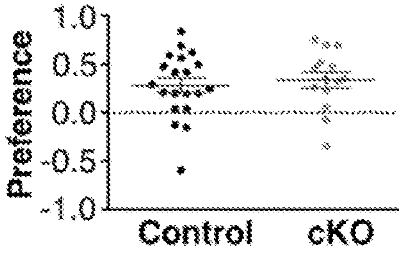
Figure 11C:
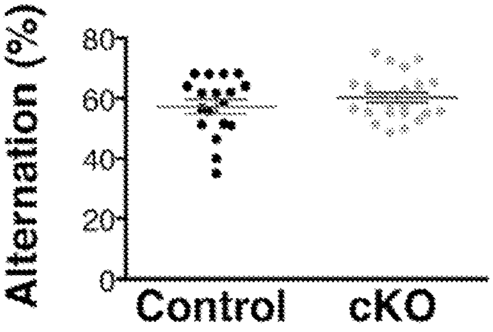
Figure 11D:
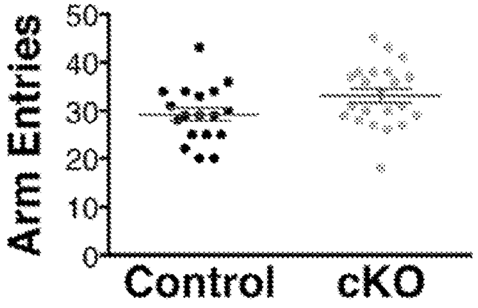
Figure 11E:
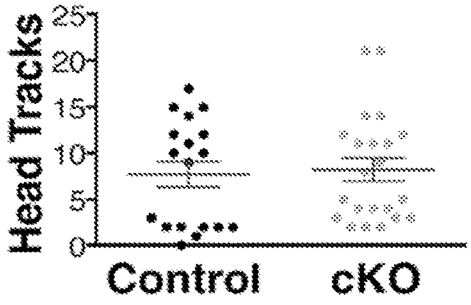
Figure 11F:
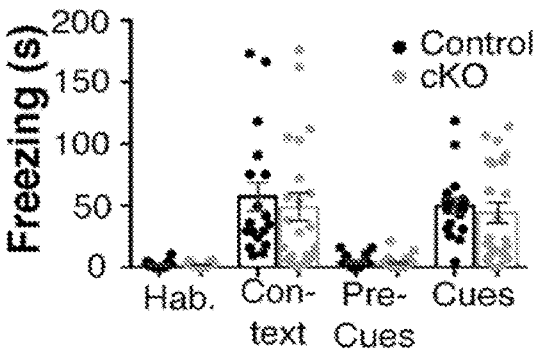
Figure 11G:
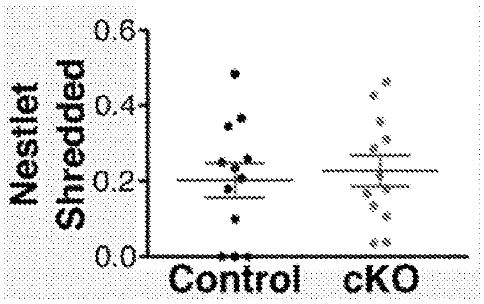

Brain hyperconnectivity has been associated with Autism-spectrum disorders (ASDs) (Dominguez et al., 2013; Keown et al., 2013; Supekar et al., 2013). Sociability in the three-chamber social interaction task has been used extensively to assess social behavior in mice (Yang et al., 2011). Lgl1 cKO mice crossed with SLICK-H were tested to assess their sociability (FIGS. 4H-4P). Before introduction of the target mouse, animals showed no preference for either side, exploring the field randomly (FIGS. 4H-4J). When a mouse was introduced to one side of the field, whereas an empty enclosure was introduced to the opposite side, control animals showed a strong preference for interacting with the novel mouse. Lgl1 cKO animals showed no preference (FIGS. 4K-4M) and a spent similar amount of time exploring the novel mouse and novel object. Interestingly, no statistically significant difference was observed in the final phase of the test where subject mice were given a choice between a familiar and novel target mouse (FIGS. 4N-4P). Similar to controls, Lgl1 cKO mice still appeared to show a preference for the novel mouse. Lgl1 cKO mice showed normal spatial memory by alternations and entries in the Y-maze (FIGS. 11C and 11D) and normal visual performance (FIG. 11E). Hippocampal- and amygdala-dependent memory formation was spared in the conditioned fear task (FIG. 11F). Nestlet-shredding activity was unchanged in the conditional deletion of Lgl1 (FIG. 11G).

Atypical PKC (aPKC) Deletion Partially Rescued Behavioral Deficits of Lgl1 cKO

Figure 5A:
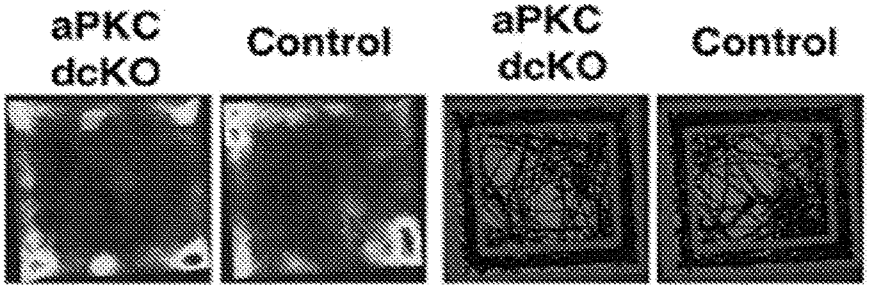
FIGS. 5A-5W are pictorial and graphical diagrams showing Conditional Triple Knockout of Lgl1, PKCι/λ, and PKCξ Rescued Asymmetric Synapse Number and Cognitive Deficit.
Figure 5B:
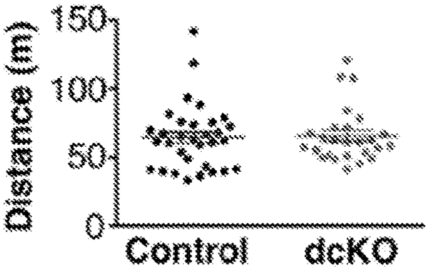
FIG. 5B shows quantification of distance traveled during the test. N=32 control, 26 aPKC dcKO animals.
Figure 5C:
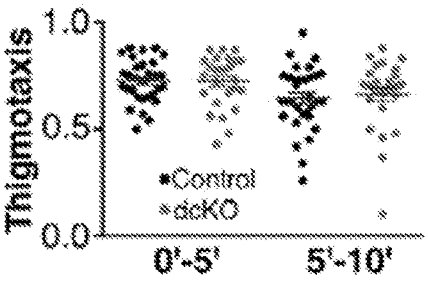
FIG. 5C shows quantification of time spent in the outer region of the field (thigmotaxis) during the first and second 5-min periods.
Figure 5D:
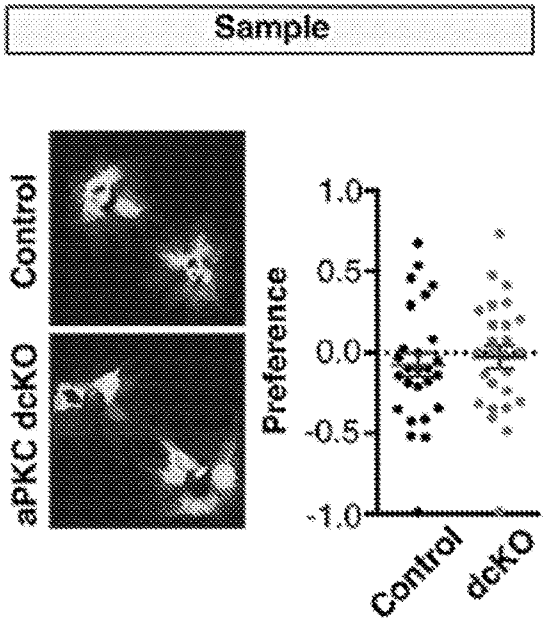
FIG. 5D shows a representative heatmap and quantification of animal preference for objects during the sample phase of the novel object recognition (NOR) test. N=26 control, 15 aPKC dcKO animals.
Figure 5E:
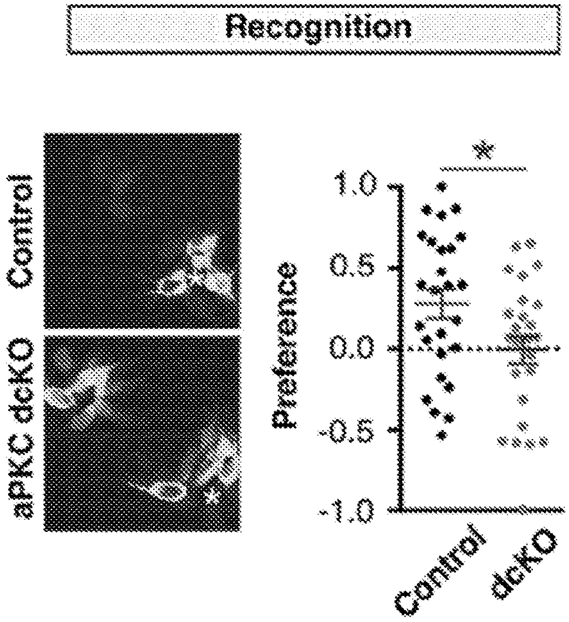
FIG. 5E shows representative heatmaps and quantification of animal preference for objects during the test phase of the NOR test. White asterisk denotes location of the novel object.
Figure 5F:
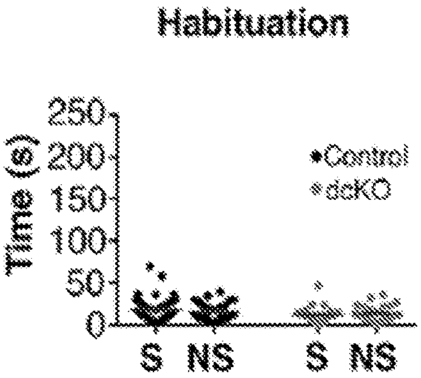
FIG. 5F shows quantification of time spent in and FIG. 5G shows preference for regions of interest (ROIs) representing future location of novel mice and objects. N=35 control, 26 aPKC dcKO animals.
Figure 5G:
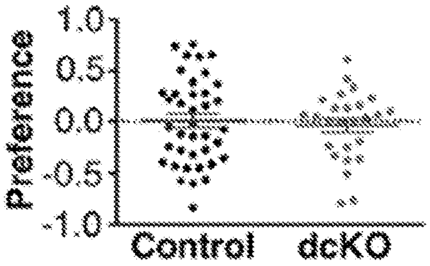
Figure 5H:
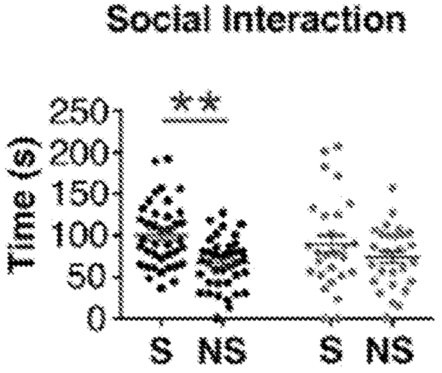
Figure 5I:
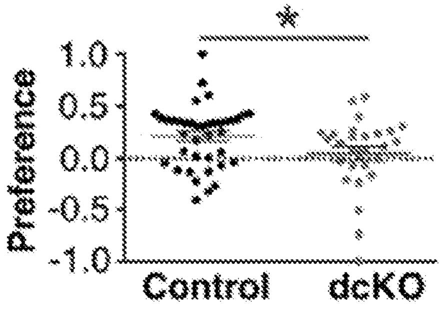
Figure 5J:
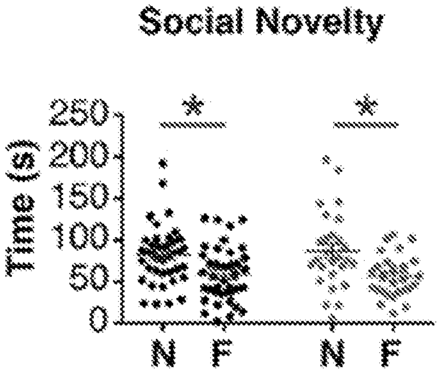
FIG. 5J shows quantification of time spent interacting with and FIG. 5**K shows preference for target mice during the social novelty phase. Positive value indicates preference for the novel mouse. N=35 control, 27 aPKC dcKO animals. *p<0.05.
Figure 5K:
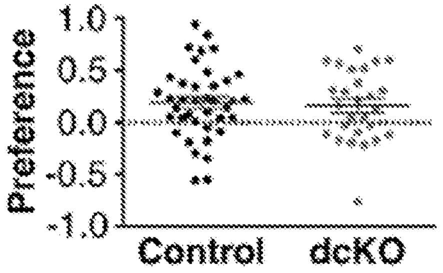

Having observed synapse phenotypes in the conditional aPKC deletion, it was then tested whether the changes would lead to behavioral deficits. In the open-field test, PKCι/λ and PKCξ dcKO animals showed no significant changes in locomotor activity or thigmotaxis (FIGS. 5A-5C). Cognitive function was also assessed, and it was found that PKCι/λ: PKCξ dcKO were impaired in the novel object recognition test (FIGS. 5D and 5E). In the social interaction test, animals showed no preference before the introduction of the novel mouse (FIGS. 5F and 5G). Littermate control animals preferred social interaction, spending more time with the novel mouse versus the novel object, whereas PKCι/λ: PKCξ dcKO spent similar amounts of time interacting with the novel mouse and novel object, maintaining a preference index close to zero (FIGS. 5H and 5I). Preference for social novelty was unaffected by aPKC deletion (FIGS. 5J and 5K).

Figure 5L:
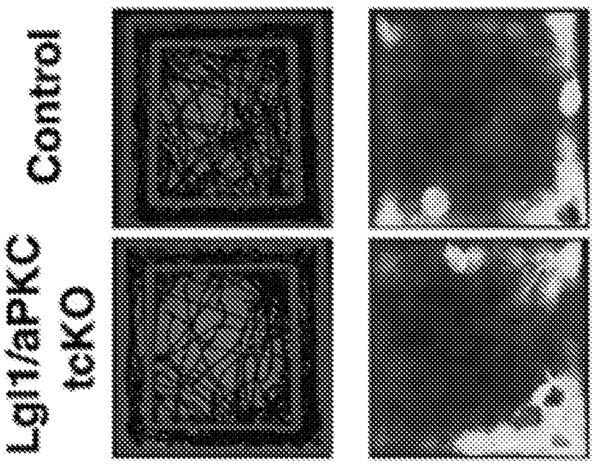
FIG. 5L shows the results of open-field analysis following P7 deletion showing representative trajectories (left) and heatmaps (right) of control and Lgl1:PKCι/λ: PKCλ tcKO animals.
Figure 5M:
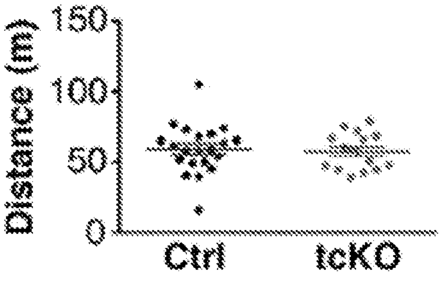
FIG. 5M shows quantification of distance traveled during the test. N=20 control, 14 Lgl1:PKCι/λ: PKCξ tcKO animals.
Figure 5N:
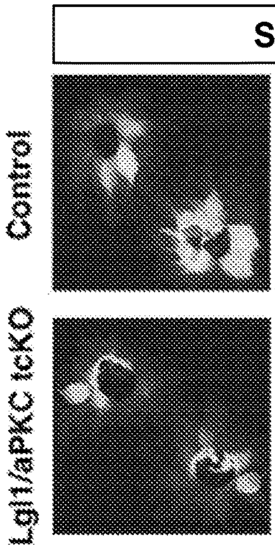
FIG. 5N shows a representative heatmap and FIG. 5O shows quantification of animal preference for objects during the sample phase of the novel object recognition (NOR) test.
Figure 5O:
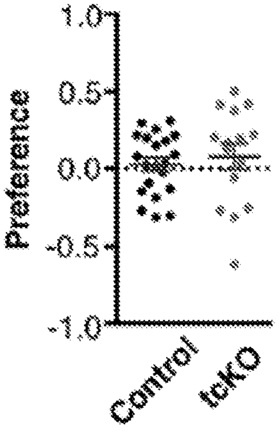
Figure 5P:
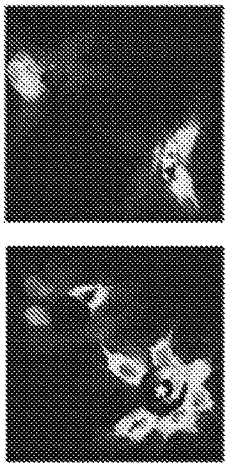
FIG. 5P shows representative heatmaps and FIG. 5Q shows quantification of animal preference for objects during the recognition test phase of the NOR test. White asterisk denotes location of the novel object.
Figure 5Q:
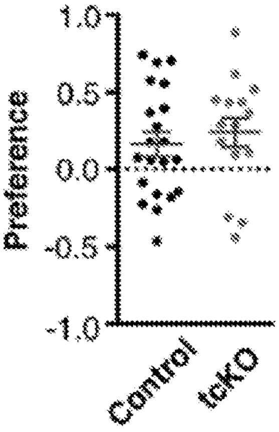
Figure 5R:
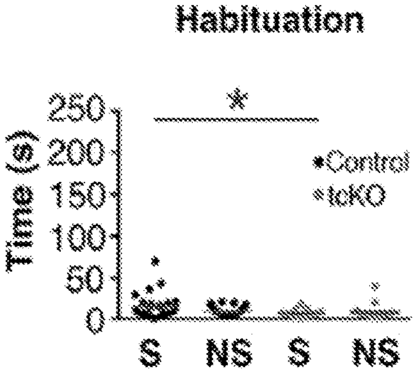
FIG. 5R shows quantification of time spent in and FIG. 5S shows preference for ROIs representing future location of novel mice and objects.
Figure 5S:
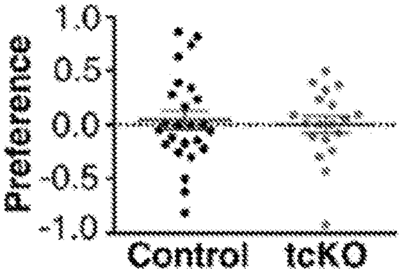
Figure 5T:
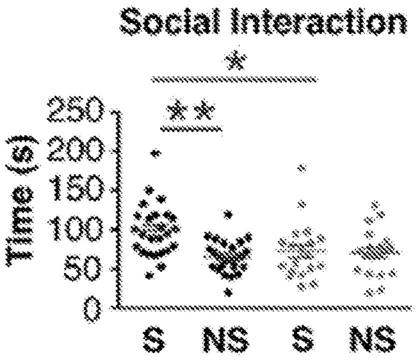
FIG. 5T shows quantification of time spent in and FIG. 5U shows preference for ROIs containing either the novel mouse or novel object. Positive value indicates preference for the novel mouse.
Figure 5U:
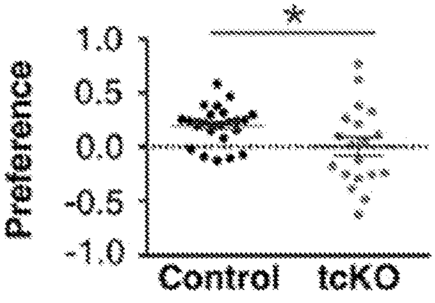
Figure 5V:
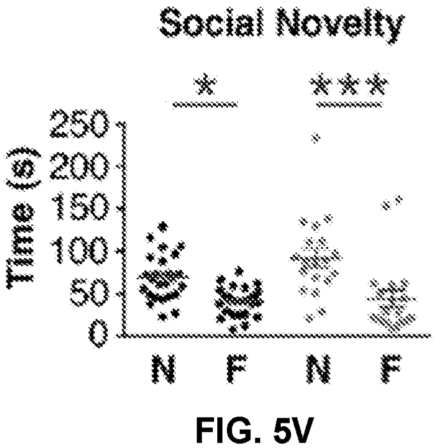
FIG. 5V shows quantification of time spent interacting with and FIG. 5W shows preference for target mice during the social novelty phase. Positive value indicates preference for the novel mouse. N=25 control, 19 Lgl1:PKCι/λ: PKCξ tcKO animals. NS, nonsocial; S, social. $^{*}p<0.05$; $^{}p<0.01$; $^{*}p<0.001$.
Figure 5W:
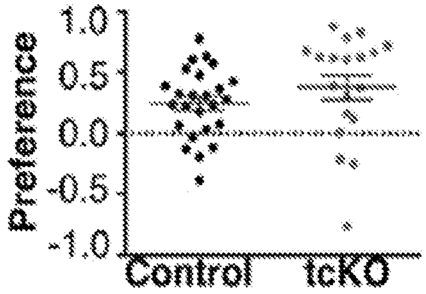

Locomotor activity was then tested and no difference was observed between littermate control and PKCι/λ: PKCξ tcKO animals (FIGS. 5L-5M). However, triple conditional deletion of Lgl1, PKCι/λ and PKCξ did rescue cognitive deficit in the novel object recognition test, with Lgl1: PKCι/λ: PKCξ tcKO animals performing similarly to littermate controls and better than chance (one-sample t test, $p=0.0262$) in the test (FIGS. 5N-5Q). These observations showed that conditional deletion of Lgl1, PKCι/λ, and PKCξ corrects observed synapse density changes and preserves cognitive function. In the social interaction test (FIGS. 5R-5W), tcKO animals still showed impairment in the social interaction phase (FIGS. 5T-5U), but not the social novelty phase (FIGS. 5V-5W).

Figure 6A:
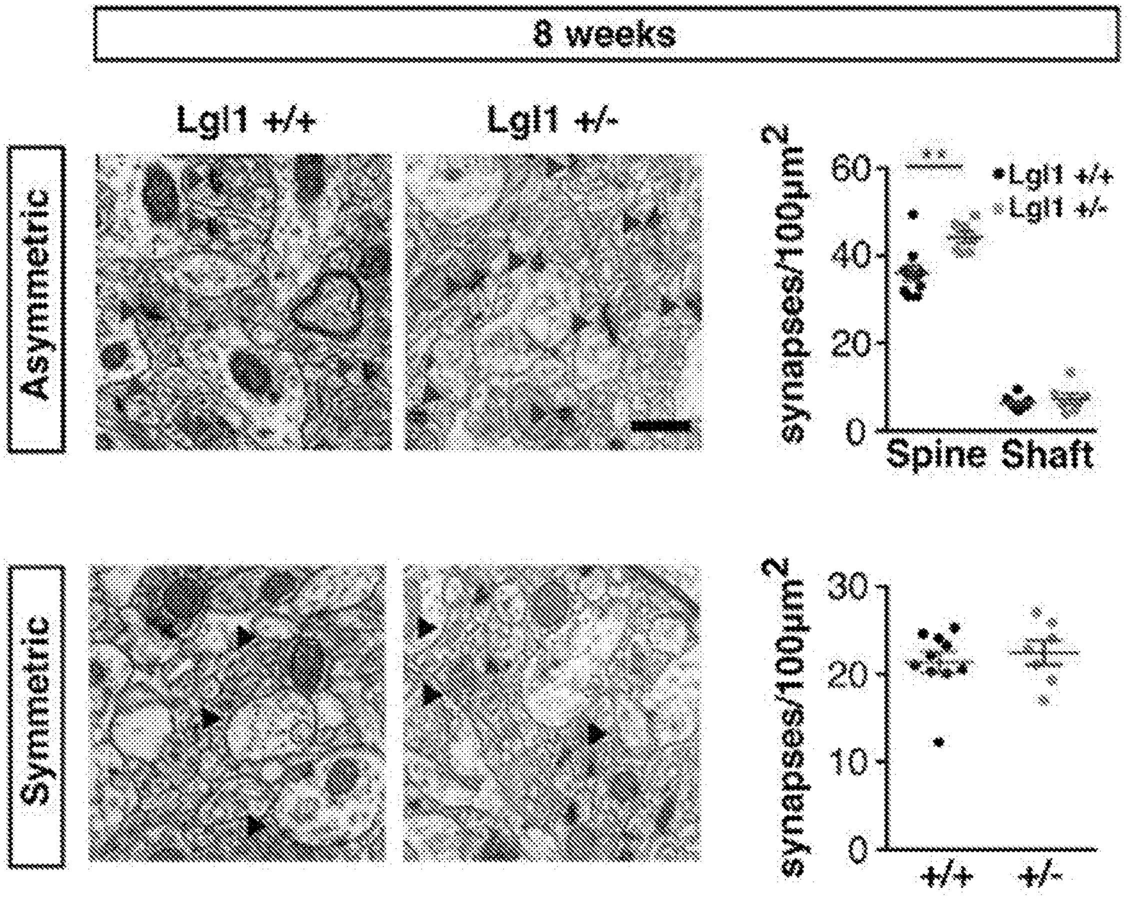
FIGS. 6A-6F are pictorial and graphical diagrams showing that $Lgl1^{+/-}$ mice showed increased synaptic numbers and SMS-like behavioral phenotypes.
Figure 6B:
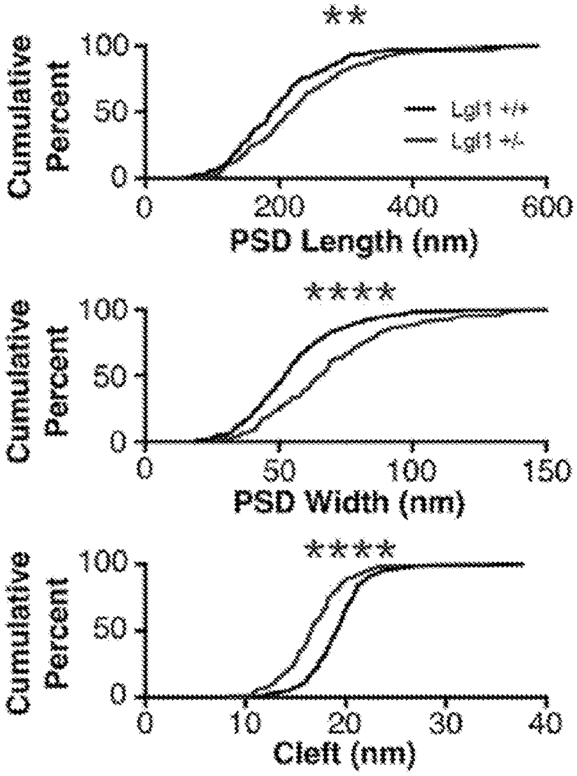
Figure 12A:
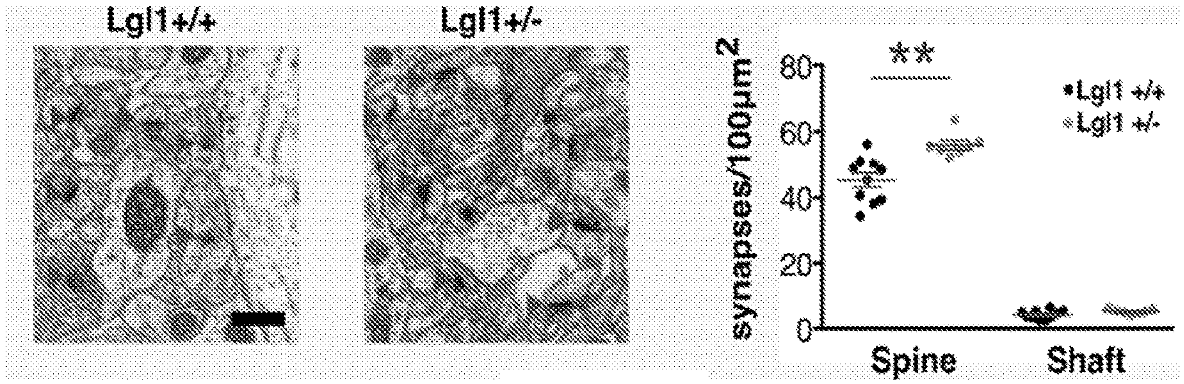
FIGS. 12A-12K are pictorial and graphical diagrams showing partial preservation of behavioral phenotypes in $Lgl1^{+/-}$ mice.

Lgl1 Heterozygotes had Increased Synapse Numbers and Displayed Behavioral Deficits Suggesting a role in Smith-Magenis Syndrome As SMS arises from heterozygous deletion of the critical region, the effects of germline heterozygous deletion of Lgl1 was assessed in the mouse models (Klezovitch et al., 2004) that removes one copy of Lgl1 from all neuronal and non-neuronal cells. Hippocampal sections from 8-week-old control and Lgl1 heterozygous animals from the germline Lgl1 KO line were imaged using electron microscopy. In these animals, the region 150-200 μm from the CA1 cell body layer showed an increase in asymmetric synapse density, with a somewhat smaller but significant increase (22.6%; FIG. 6A and proximal region shown in FIG. 12A) compared with what was observed when both copies were deleted in the conditional KO. Symmetric synapses were not affected. Analysis of synapse ultrastructure revealed longer and wider PSDs and smaller synaptic clefts (FIG. 6B).

Figure 6D:
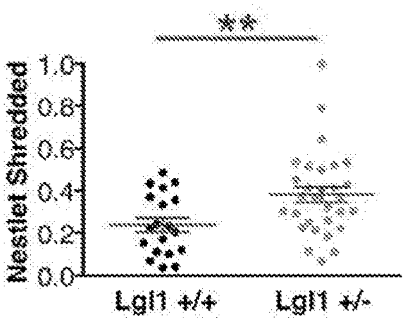
Figure 12B:
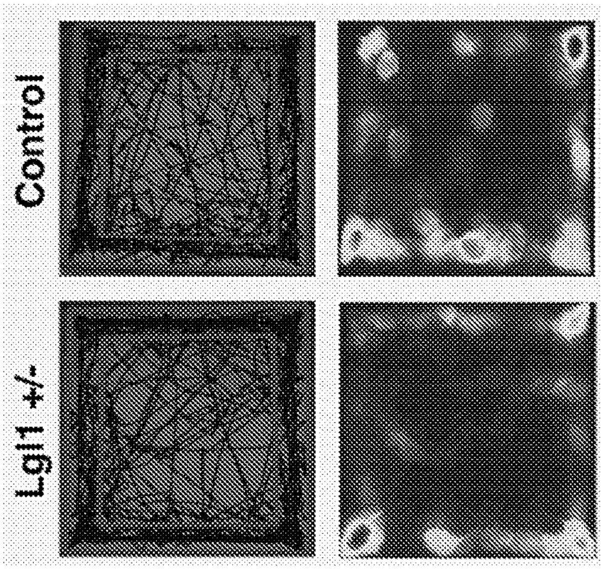
Figure 12C:
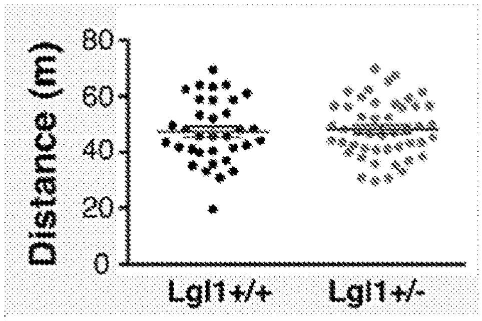
Figure 12D:
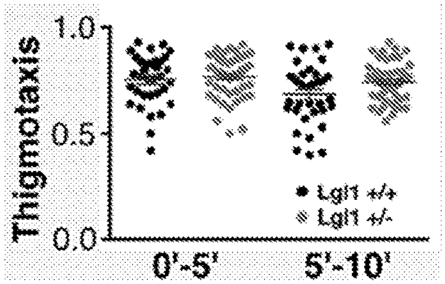
Figure 12E:
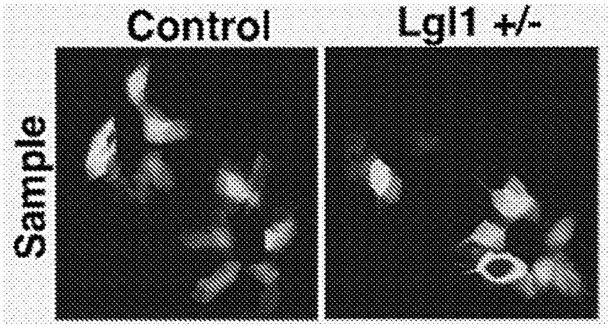
Figure 12F:
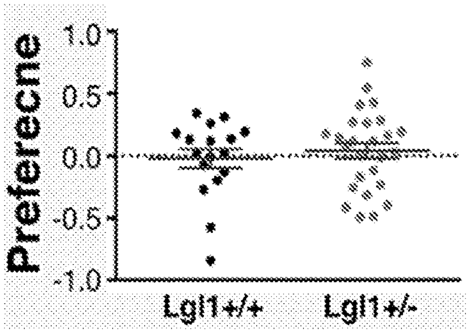
Figure 12G:
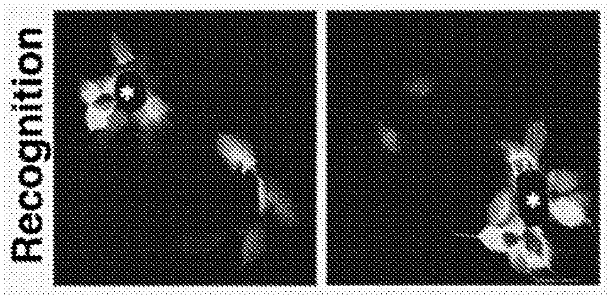
Figure 12H:
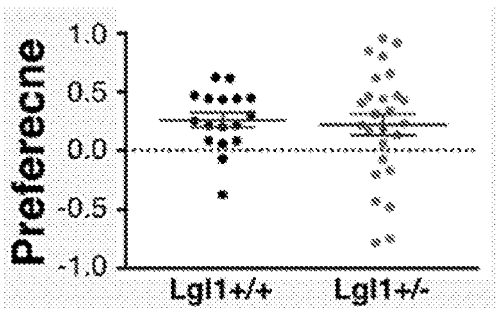

In the open field test, $Lgl1^{+/-}$ animals did not show a significant difference from control animals after 10 minutes (FIGS. 12B-12C). During an extended observation period of 60 minutes in the open field (FIG. 6C), $Lgl1^{+/-}$ animals show increased locomotor activity by 12.0% overall.

Stereotyped repetitive behavior was also tested and it was found that $Lgl1^{+/-}$ animals showed increased nestlet shredding when given cotton nesting material in a novel cage (FIG. 6D), shredding 59.4% more material during the test. As this behavior was not observed in Lgl1 cKO, this is likely a result of Lgl1 deletion in heterozygotes in the subcortical areas that are not affected by the Thy-1 dependent deletion in the Lgl1 cKO animals crossed with SLICK-H.

Figure 6E:
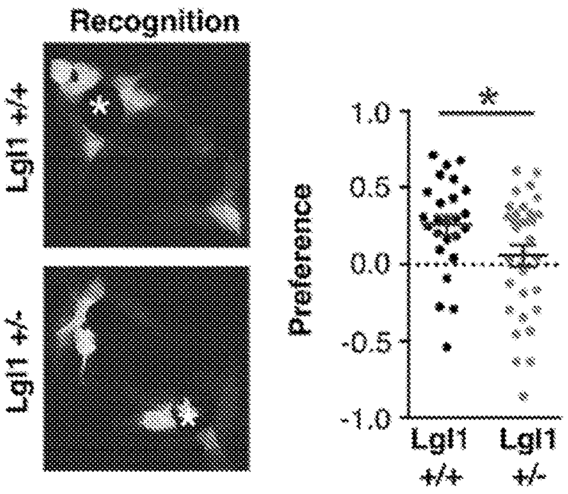
Figure 6C:
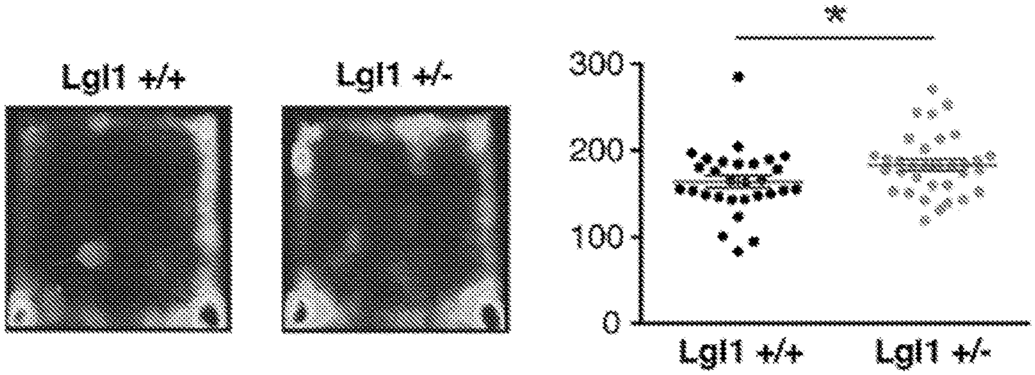

Preference for novel object recognition was spared in $Lgl1^{+/-}$ animals (FIGS. 12E-12H) following a 2-minute delay, suggesting that this cognitive task might be partially spared by either reduced impact on synapse density or synaptic function due to the remaining copy of Lgl1. Therefore, an additional novel object recognition test was performed, this time with a 24-hour delay between the initial sample period and the recognition test. After 24 hours, control animals successfully discriminated novel and familiar objects, while $Lgl1^{+/-}$ animals did not (FIG. 6E). Patients with SMS demonstrate mild to moderate cognitive impairment or developmental delay, and it is likely that the partially preserved recognition of novel objects reflects a mild impairment in the mouse model.

Figure 6F:
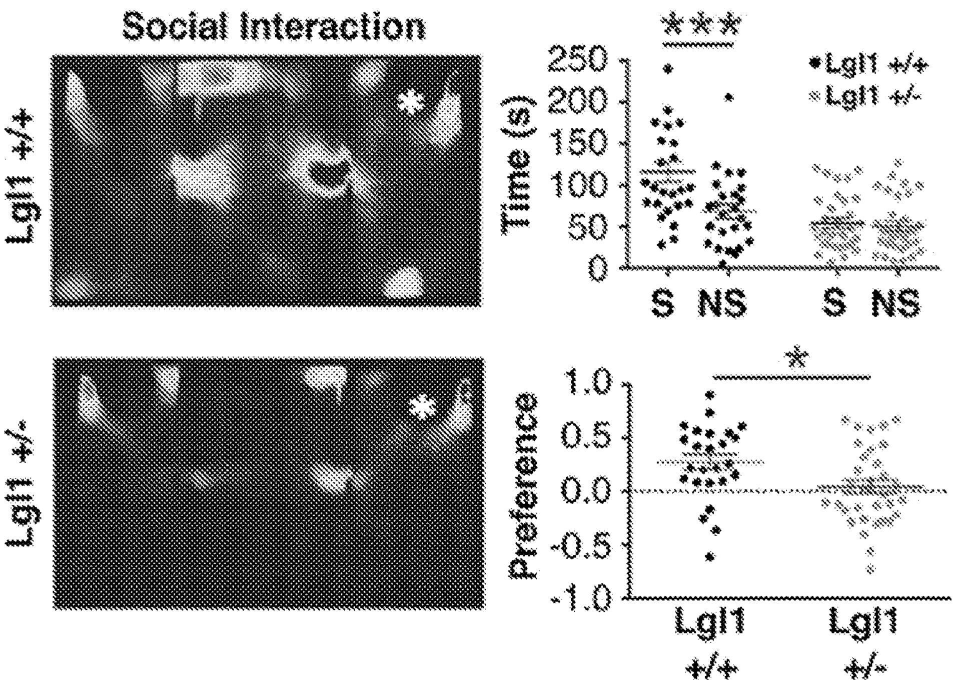
Figure 12I:
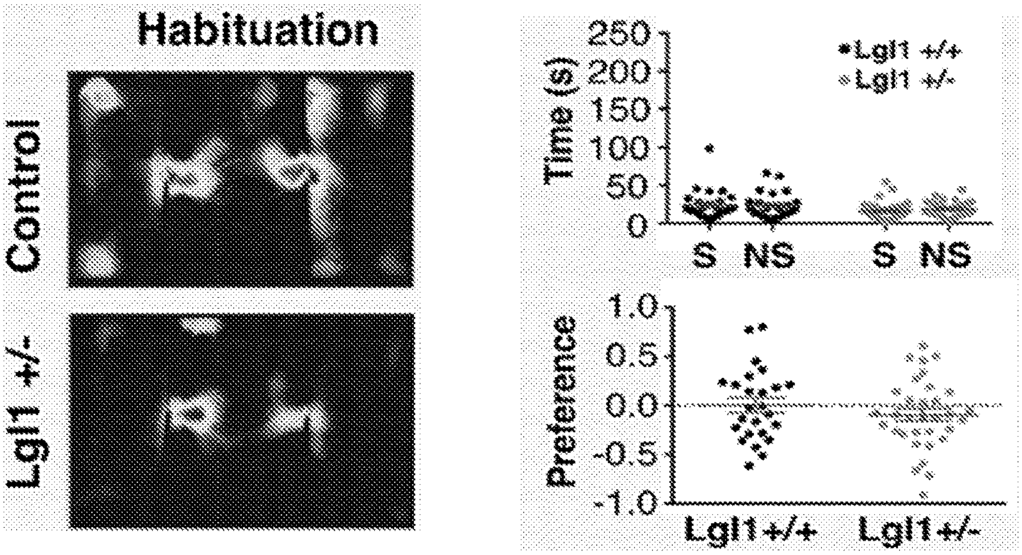
Figure 12J:
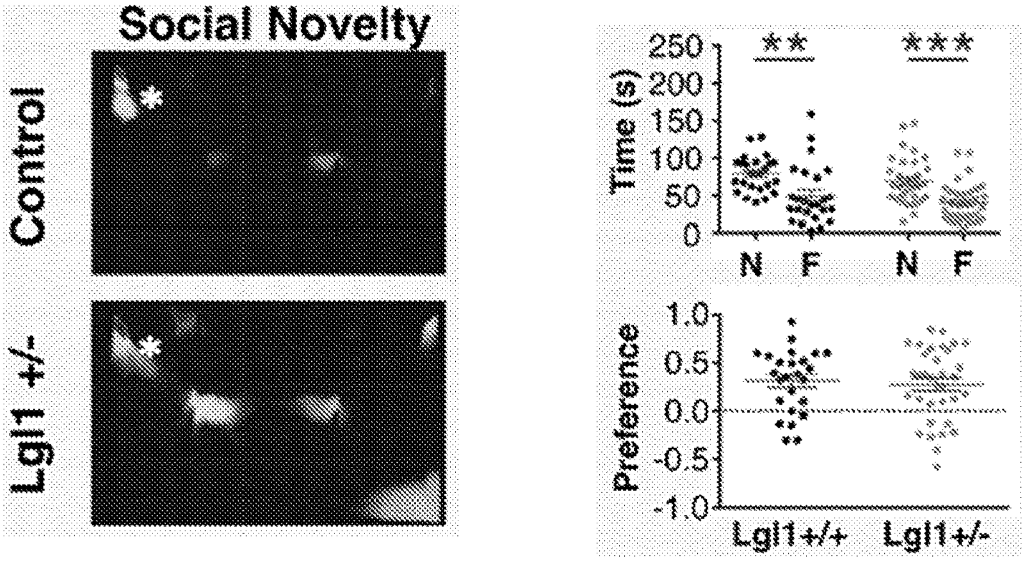
Figure 12K:
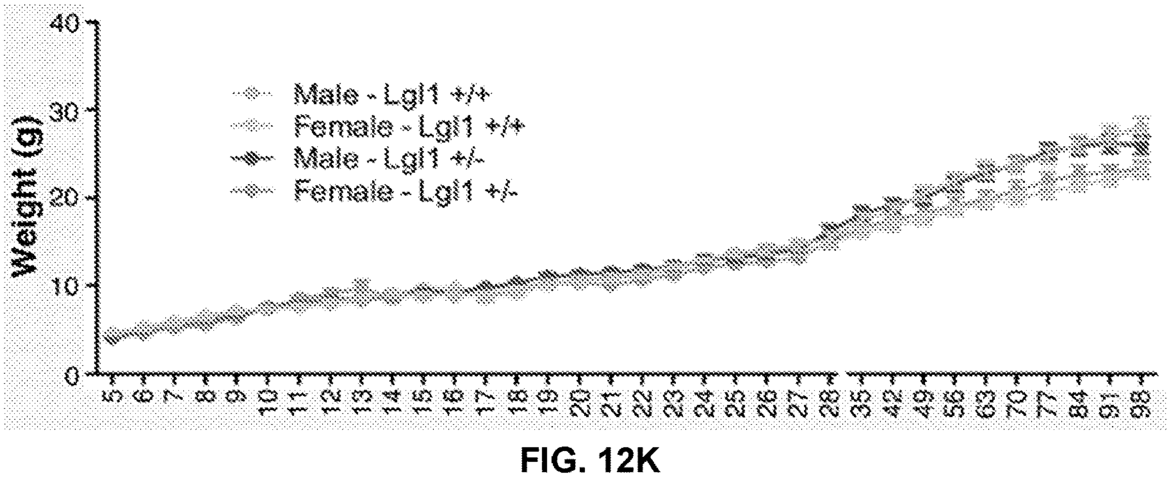

Similar to Lgl1 cKO animals, $Lgl1^{+/-}$ animals demonstrated deficient social interaction, but spared preference for social novelty (FIGS. 6F and 12I-12J), indicating that loss of one copy ofLgl1—as occurs in SMS—is sufficient to give rise to ASD-like behaviors. $Lgl1^{+/-}$ animals did not show a difference from control littermates in age-dependent weight gain (FIG. 12K).

Figure 7A:
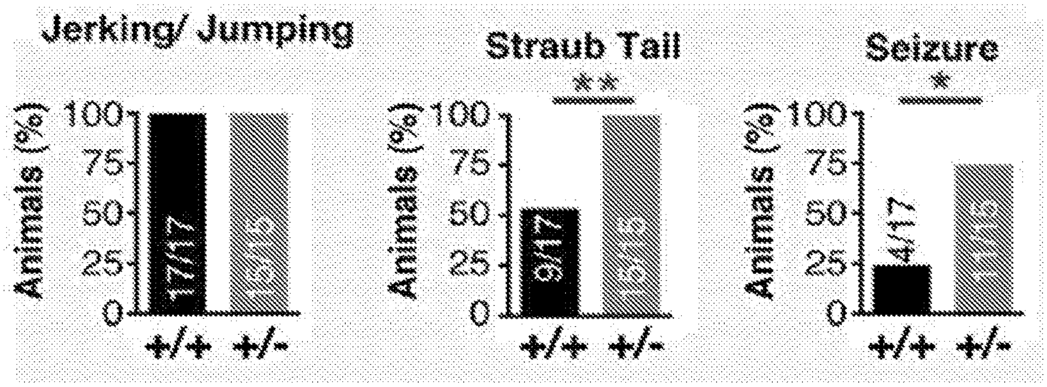
FIGS. 7A-7E are pictorial and graphical diagrams showing decreased seizure threshold in $Lgl1^{+/-}$ mice and rescue of social interaction by NMDAR blockade.
Figure 7B:
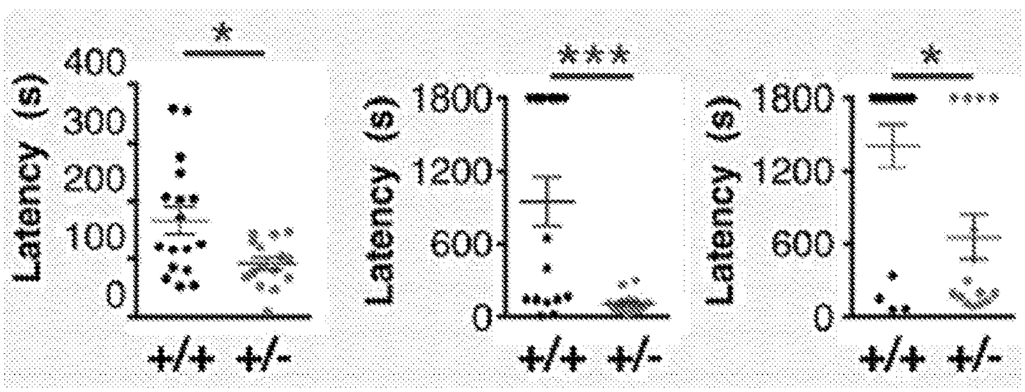

Social Interaction Deficit in $Lgl1^{+/-}$ may be Caused by Excessive NMDA Current Because SMS often presents with either seizures or abnormal EEG without overt seizure (Chen et al., 1996; Greenberg et al., 1996), it was tested whether abnormally high synapse density and NMDA current would lower the seizure threshold in response to the GABAA-blocking drug pentylenetetrazol (PTZ). Following injection of 50 mg/kg PTZ, the occurrence and latency of activities indicating the onset of a seizure were recorded. All animals tested showed at least one instance of jumping or full-body jerking (FIG. 7A), whereas $Lgl1^{+/-}$ animals showed a shorter latency to the behavior following PTZ administration (FIG. 7B). $Lgl1^{+/-}$ animals also showed significantly higher occurrence and shorter latency to Straub Tail, indicating persistent muscle contraction, and also showed a similar effect for the occurrence of clonic-tonic seizures.

Figure 7C:
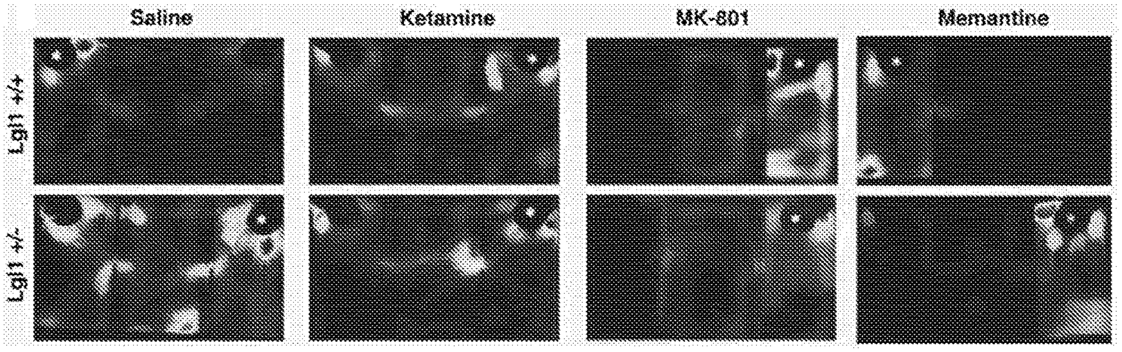
Figure 7D:
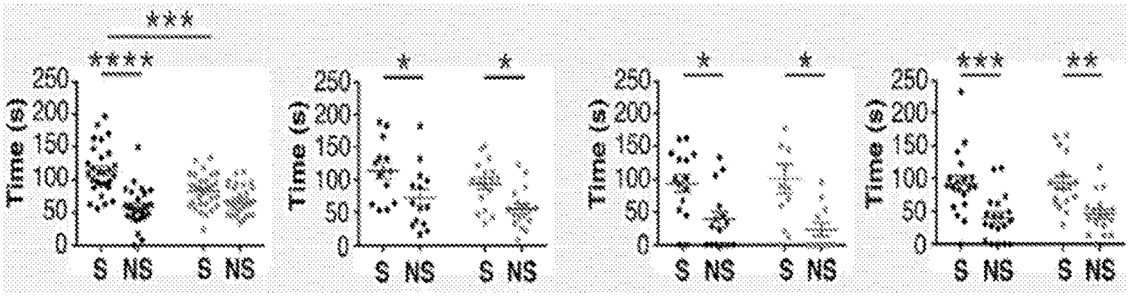
Figure 7E:
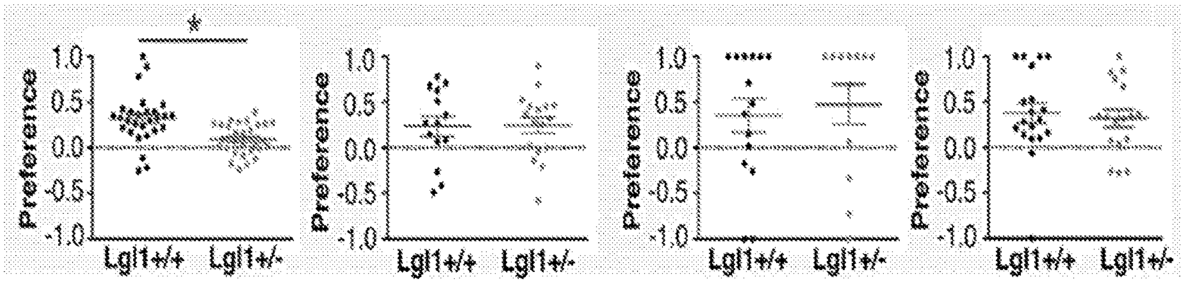
Figure 13A:
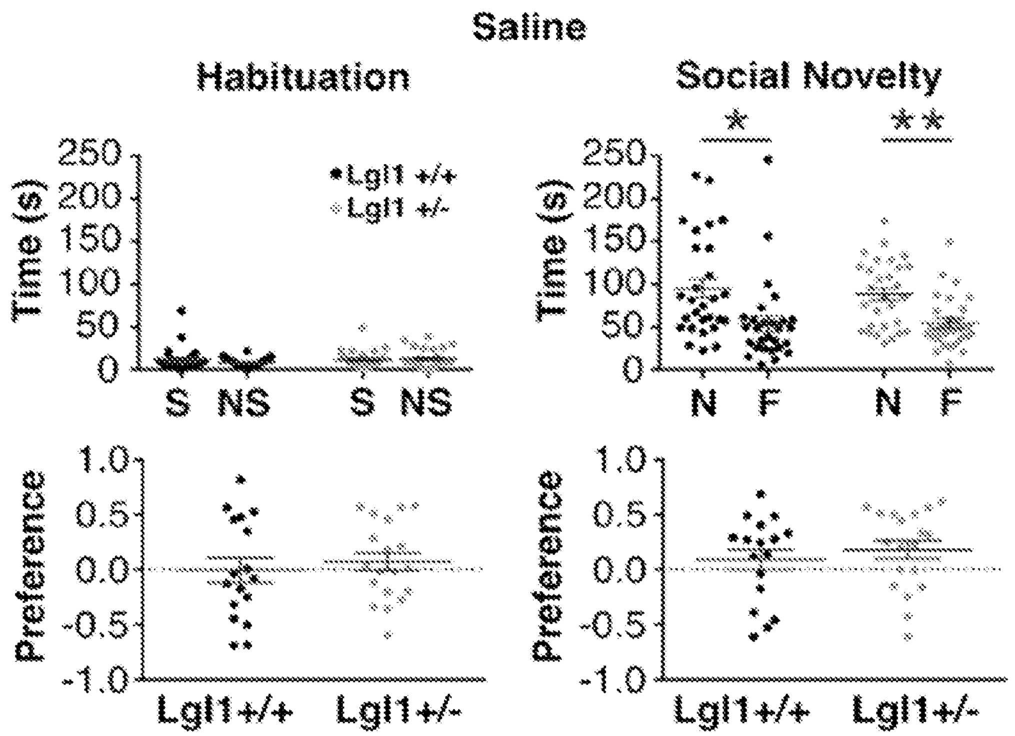
FIGS. 13A-13E are graphical diagrams showing additional phases of social interaction test in saline, ketamine, and MK-801 treated animals.
Figure 13B:
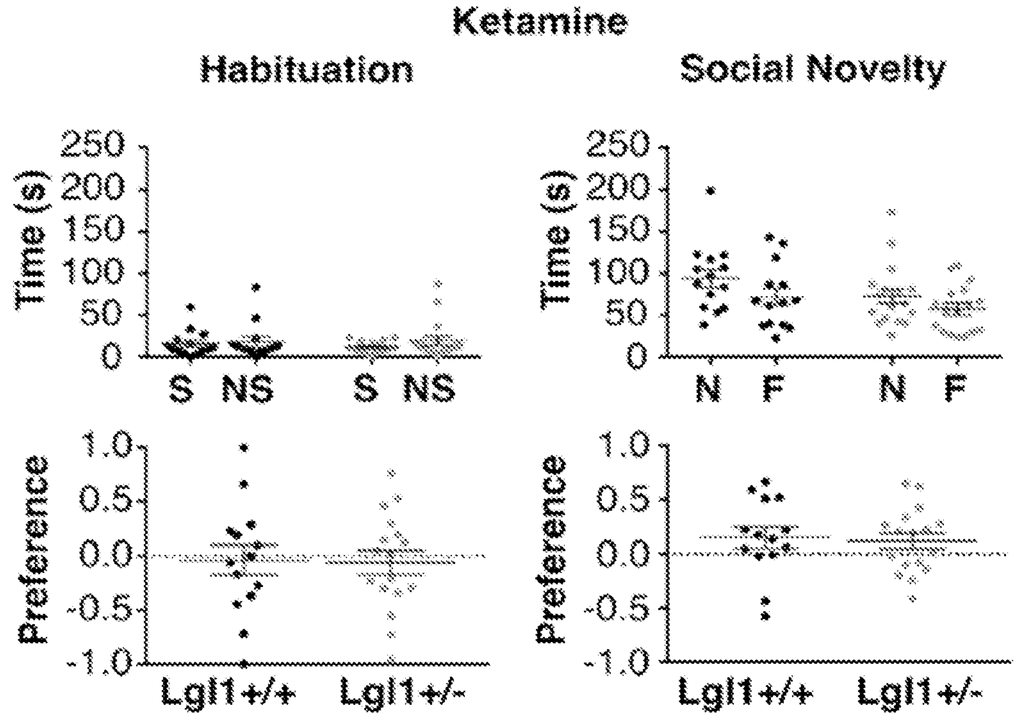
Figure 13C:
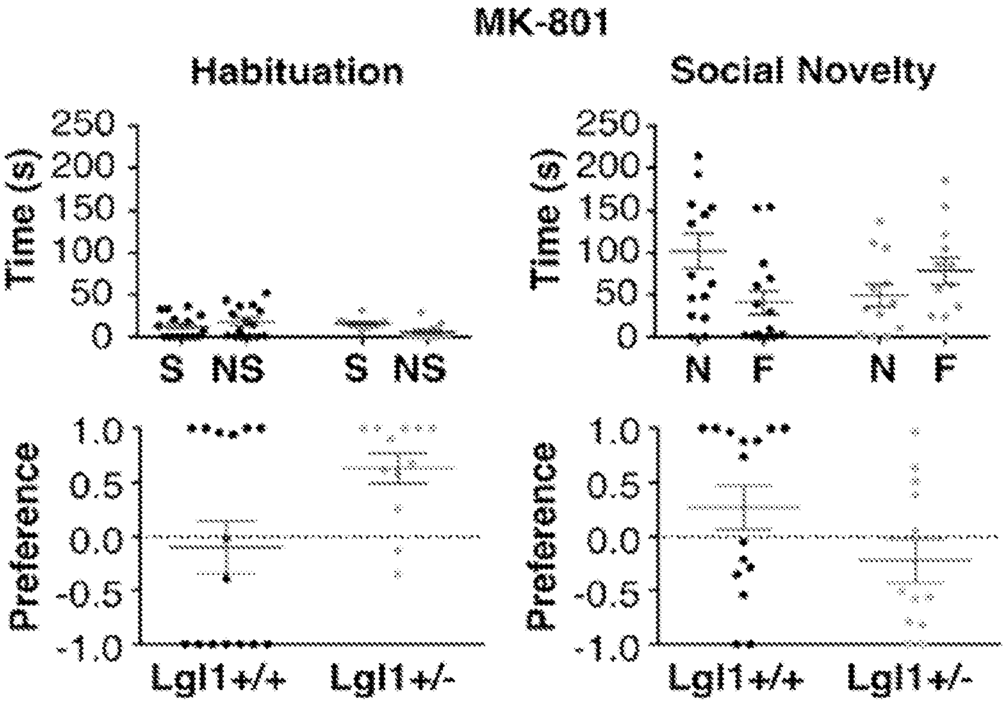
Figure 13D:
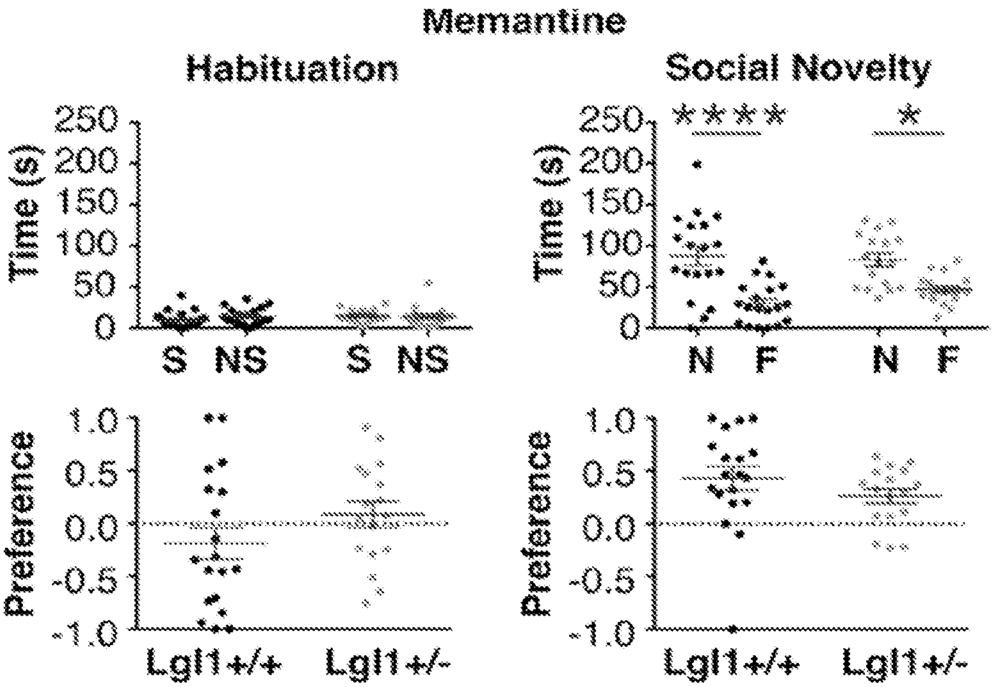
Figure 13E:
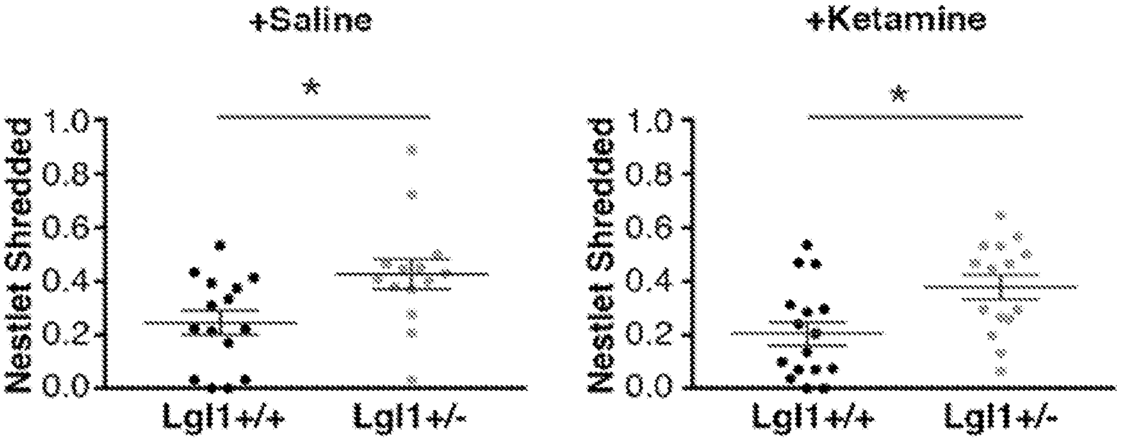

The lower AMPA/NMDA ratio and unaffected AMPA current suggests that Lgl1 mutants may have excessive NMDA current. It was therefore asked whether abnormal NMDAR-dependent signaling could underlie some of the behavioral deficit, especially social interaction, that was observed. Pharmacological blockers of NMDARs were used, and animals tested in the three-chamber social interaction test. Subanesthetic doses of ketamine have been shown to provide rapid blockage of NMDAR-dependent signaling. Social interaction was tested with injection of 50 mL sterile saline, and it was observed that control animals preferred social interaction, whereas Lgl1$^{+/-}$ mice did not show a preference (FIGS. 7C-7E). Following injection of 30 mg/kg ketamine, Lgl1$^{+/-}$ mice showed a clear preference for social interaction similar to what was observed from control animals (FIGS. 7C-7E). Preferences in habituation and social novelty phases are unaffected by saline or drug injection (FIGS. 13A-13D). Ketamine injection did not change nestlet-shredding activity (FIG. 13E). In addition, MK-801 (dizocilpine) was also tested at 0.3 mg/kg and memantine at 20 mg/kg, and it was observed that Lgl1$^{+/-}$ strongly preferred social interaction, as did control mice (FIGS. 7C-7E). These results suggest that excessive NMDA current due to Lgl1 deletion may contribute to some of the behavioral deficits and that inhibiting NMDARs may help alleviate some of the neuropsychiatric symptoms in SMS patients with Lgl1 deletion.

The following examples are intended to illustrate but not limit the invention.

Example 1

Electron Microscopy—Lgl cKO or Lgl1$^{+/-}$ and littermate control mice were anesthetized i.p. with a ketamine/xylazine cocktail, and perfused with modified Karnovsky's fixative (2.5% glutaraldehyde and 2% PFA in 0.15 M sodium cacodylate buffer, pH 7.4) at room temperature. After postfixation in the same solution overnight at 4° C., whole brains were cut coronally (200 μm) with a vibratome. Sections were postfixed with 1% osmium tetroxide for 1 on ice. Following en-block staining in 2% uranyl acetate in distilled water for 1-2 h, sections were dehydrated in a graded ethanol series and then treated twice in acetone for 10 min each. Sections were infiltrated in Durcupan resin (Sigma-Aldrich) and were embedded at 60° C. for 48 h. Ultrathin sections from CA1 region were cut and stained with uranyl acetate and Sato's lead. Image acquisition used a FEI Tecnai Spirit G2 Spirit BioTWIN transmission electron microscope equipped with an Eagle 4k HS digital camera (FEI, Hilsboro, OR). 10-15 fields from the distal stratum radiatum (150-200 μm from CA1 pyramidal cell bodies) and proximal stratum radiatum (40-50 μm from CA1 pyramidal cell bodies) were selected under 6800× magnification, and synapses were counted in each field. Synapses that displayed polyribosomes and/or actin bundles were determined to be on the dendritic shaft while synapses lacking those structures were determined to be on the dendritic spines. For ultrastructure analysis, asymmetric synapses from the distal stratum radiatum area were imaged at 18500× magnification. Only asymmetric synapses with a clearly recognized PSD and synaptic cleft were selected. The bouton area, cleft distance, reserve pool vesicles, docked vesicles, PSD width and PSD length were analyzed using Image J. Analysis of ultrastructure was done by experimenters blinded to animal genotype.

Hippocampal primary cell culture—Hippocampal neuron culture was performed as described previously (Meffert et al., 2003). Glass coverslips were washed overnight in nitric acid and rinsed thoroughly and washed with 100% ethanol before being placed in a drying oven. The day before cell culturing, coverslips were coated with 80 mg/mL Poly-D-Lysine (PDL) overnight at room temperature. Coverslips were washed and coated with 40 mg/mL PDL with 2.5 mg/mL Laminin for 3 hours at 37° C.

Brains from E18.5 pups were removed in L15 media and hippocampi were dissected and placed in individual tubes. Hippocampi were washed twice with Mg/Ca free sterile PBS (CellGro) and incubated with Trypsin/EDTA solution (0.25% Trypsin, 2.2 mM EDTA) for 15 minutes at 37° C. Trypsin was neutralized by the addition of 10% vol/vol heat-inactivated horse serum (Life Technologies). Resulting solutions were pelleted and resuspended in Neurobasal medium supplemented with 2% B27 (Invitrogen), 5% fetal bovine serum (Invitrogen), penicillin/streptomycin (Cellgro), and Glutamax (Invitrogen) and washed twice. Cells density was determined, and cells were plated at a density of $2.5\times10^{4}$ cells/cm$^{2}$. Half of the growth medium was exchanged every 3 days. Arabinofuranosyl Cytidine (Ara-C, 4 μM) was added at day 6 in vitro to prevent glial cell proliferation. Cultures were grown for 14 days at 37° C. in a 5% carbon dioxide atmosphere.

AAV Injections—Animals were anesthetized with Isoflurane and the surgical area was prepared with 70% ethanol and Betadine solution. Animals were placed in head bars and maintained under Isoflurane anesthesia throughout the procedure. Animals were given an injection of Buprenex subcutaneously at the beginning of the procedure. Injections were targeted to the CA1 region of the dorsal hippocampus. Stereotaxic coordinated used were (from Bregma): AP −2.0, ML +/−1.4, DV −1.35 and −1.25. Animals received 2 injections into each hemisphere. Animals were allowed to recover locomotor and self-grooming activity before being returned to their home cage. Animals were given injections of Buprenex twice daily for 3 days post-surgery. Viruses used were AAV1.hSyn.HI.eGFP-Cre.WPRE.SV40 and AAV1.hSyn.eGFP.WPRE.bGH (UPenn Vector Core). Viruses were diluted to $3\text{-}5\times10^{12}$ viral particles/mL for injection. 300 nL of virus solution was injected per site. Animals recovered for 14 days before the beginning of behavior experiments.

Behavioral Assays—For all behavioral assays, testing was performed during the light phase in a dimly lit room (<100 lux) with indirect lighting on the testing area unless otherwise noted. Both male and female animals were tested in behavior tests, with the exception of groups of animals injected with AAV at 6 weeks, which was performed in males only.

Open Field Test—The open field test is performed in a plastic 40 cm×40 cm acrylic box (Stoetling) with dark walls with a nonreflective base plate. Spatial cues are placed on one wall of the field. Mice are placed in the center of the field and allowed to explore freely for 10 minutes. Mice are scored for distance travelled, time in the inner and outer regions of the field, time spent self-grooming, rearing activity, and jumping activity. Outer region is defined as the region within 5 centimeters of the edge of the field.

A 60-minute variant of the test was applied to the Lgl1$^{+/-}$ mice and littermate controls with all aspects of the testing area identical to the 10-minute test. Animals that performed the 10-minute test were not used for the 60-minute test in order to avoid effects of prior exposure to the testing apparatus.

Novel object recognition test—The novel object recognition test was performed as described (Antunes and Biala, 2012) immediately following a 10-minute exploration period in an empty apparatus. Animals are placed in a field containing two copies of a novel object and allowed to explore freely. After the sample phase, animals were removed from the field and the objects were replaced with one copy of the previously explored object and a novel object in the same positions in the field as during the sample phase. Animals were allowed to explore freely for 5 minutes. For scoring of interaction time, ROIs containing the target objects were selected in MATLAB. ROIs were selected by experimenters blinded to the animal genotypes or virus treatment.

Social interaction test—The social interaction test was performed as previously described (Yang et al., 2011). The sociability apparatus (Stoetling) has three 20 cm×40 cm chambers and two target enclosures 7 cm in diameter and 15 cm tall. During testing, the apparatus was surrounded by opaque panels to prevent mice from seeing out of the apparatus.

Animals were placed in the center chamber of the 3-chambered sociability apparatus with the doors between chambers closed for 10 minutes to habituate to the testing conditions. The doors were removed, and mice were allowed to explore the full field for 10 minutes. Non-littermate strain- and age-matched target mice from a separate cage were introduced during the social interaction phase of the test. For the social novelty phase, target mice from the social interaction phase were kept in the same location and a novel target mouse was introduced to the opposite chamber. For scoring of interaction time, ROIs containing the target mouse and novel object were selected in MATLAB. ROIs were selected by experimenters blinded to the animal genotypes or virus treatment.

Scoring for distance travelled and thigmotaxis during the open field test, as well as time spent interacting with objects in the Novel Object Recognition test and time spent interacting with target mice and objects in the Social Interaction test was performed using Autotyping 15.04 in MATLAB 2014b (Patel et al., 2014)(MathWorks).

Nestlet shredding—Mice were removed from their home cage and placed individually into a clean novel cage containing a weighed piece of cotton nesting material of approximately 2.8 g. Mice were left in the cage for 60 minutes. At the end of the testing period, mice were returned to their home cage. Shredded material was separated from the undisturbed portion, which was weighed (Li et al., 2006).

Electrophysiology—For Lgl1 cKOs and littermate controls at P13-15, mice were anesthetized by isofluorene. Mice were decapitated, and their brains were quickly removed and placed in ice-cold dissection buffer containing the following (in mM): 87 NaCl, 2.5 KC1, 1.25 $NaH_2PO_4$, 25 $NaHCO_3$, 20 glucose, 75 sucrose, 0.5 $CaCl_2$, and 7 $MgCl_2$, pH 7.35. Transverse hippocampal slices were cut in 300 μm-thick sections on a vibratome (Lieca V T1200). Slices were allowed to recover at 35° C. for 20 min and then at room temperature for 1 to 6 hr in carbogenated ACSF, containing (in mM): 124 NaCl, 2.5 KC1, 24 $NaHCO_3$, 1.2 $NaH_2PO_4$, 2 $CaCl_2$, 2 $MgCl_2$ and 12.5 glucose, 5 HEPES pH 7.4. Individual slices were transferred to a recording chamber and then continuously perfused at a rate of 2-3 ml/min with ACSF containing 1 μM TTX (Tocris) and either 20 μM gabazine or 20 μM CNQX for mEPSC or mIPSC recordings, respectively. CA1 pyramidal cells were visualized by infrared differential interference microscopy.

For mEPSCs, whole-cell recordings were made using 3-5 MΩ pipettes filled with an internal solution that contained (in mM): 145 CH3O3SCs, 5 NaCl, 10 HEPES, 5 EGTA, 0.3 $Na_2GTP$ and 4 MgATP, (pH was adjusted to 7.3 and osmolarity was maintained at 280-290 mOsm). For mIPSC recordings, whole-cell recordings were made using 3-5 MΩ pipettes filled with an internal solution that contained (in mM): 135 CsCl, 4 $MgCl_2$, 0.1 EGTA, 10 HEPES, 2 MgATP, 0.3 NaGTP, 10 Na2Phosphocreatine (pH was adjusted to 7.3, and osmolarity was maintained at 280-290 mOsm).

Cells were voltage clamped at −70 mV. Recordings started after 5 minutes to allow for stabilization of the established whole-cell configuration. Signals were recorded with a 5× gain, low-pass filtered at 2 kHz and digitized at 5 kHz (Molecular Devices Axopatch 200B) with pCLAMP 10 software (Molecular Devices); analysis was performed with Clampfit (pCLAMP). The automatic detection was verified post hoc by visual inspection. Values are presented as mean±SEM. Mann-Whitney U-statistic test was used to compare changes with the control.

For LTP induction, transverse hippocampus slices were harvested from 9-10-week-old mice. Slices were recovered for at least 1 hour before moving to recording chamber in aCSF (in mM): NaCl 119, KC1 2.5, $NaH_2PO_4$1, $NaHCO_3$ 26.2, Glucose 11, $MgCl_2$ 1.3 and $CaCl_2$ 2.5 bubbled with 95% $O_2$ and 5% $CO_2$. Stimulus was given at 0.033 Hz to evoke field potential and the resistance of glass electrode was 1-2 MΩ with aCSF as internal solution. Input-Output were recorded by gradually increasing the strength of stimulus. After 30 min stable baseline recording, LTP was induced by HFS or TBS. HFS was 100 pulses at 100 Hz. TBS contained four trains of theta bursts with 20 second intervals, each train had 10 burst with 0.2 interval.

For AMPA/NMDA ratio determination, a broken glass pipette was used as a stimulus electrode. The resistance of patch the clamp pipette was 3-5 MΩ Internal solution (in mM): $CsMeSO_4$ 115, CsCl20, Na phosphocreatine 10, $MgCl_2$ 2.5, $Na_2ATP$ 4, $Na_3GTP$ 0.3, EGTA 0.6, HEPES 10 and QX-314-Cl 5. A cut was made between CA1 and CA3 to avoid epilepsy events. The position of stimulus electrode was gently adjusted to evoke a single peak EPSC. For AMPA current, holding potential was set at −70 mV, and for NMDA current, holding potential changed to +40 mV. NMDA current was quantified as the peak 100 ms after stimulus artifact, where there is no AMPA current.

Biochemical fractionation—Subcellular fractionation was performed as previously described (Cohen et al., 1977) with modifications. Forebrains from P14 wild type mice were homogenized to 10% (wt/vol) in ice cold 0.32M sucrose buffer containing 1 mM $MgCl_2$, 0.5 mM $CaCl_2$, 1 mM $NaHCO_3$ and protease inhibitors using 16 strokes with a glass dounce. The homogenates were spun at 710 g for 30 min at 4° C. to pellet out nuclei and large debris. The supernatant was further centrifuged at 13800 g for 10 min at 4° C. to get pellets (P2). P2 pellets were resuspended in the sucrose buffer and layered on top of a discontinuous sucrose gradient containing 1.0M and 1.4M sucrose in 4 mM HEPES buffer pH 7.4. The gradient was centrifuged at 82500 g for 1 h at 4° C. Synaptosomes were recovered from the cloudy band between 1.0M and 1.4M sucrose, resuspended in 1 mM $NaHCO_3$ (1:9 vol/vol), and lysed by hypo osmotic shock using 3 strokes with a glass dounce. The lysates were then incubated with an equal volume of 0.32M sucrose buffer containing 1% Triton-X shaking at 4° C. for 15 min and spun at 82500 g for 1 h. The PSD fraction was obtained from the resulting pellet. The synaptic membrane fraction (SMF) was precipitated from the supernatant using the methanol/chloroform/$H_2O$ method (Wessel and Flügge, 1984). Both the PSD fraction and SMF were solubilized in 3% SDS for western blot analysis.

For isolation of surface-localized proteins, acute slices were isolated from control and Lgl1 cKO animals. Sections were cut at 300 μm thickness for P21 mice and 400 μm thickness for P56 mice. Sections were collected in carbogenated dissection buffer containing 25 mM $NaHCO_3$, 1.25 mM $NaH_2PO_4$, 2.5 mM KCl, 7 mM $MgSO_4$, 25 mM Glucose, 0.5 mM CaCl2 with Choline Chloride (0.11 mM), Sodium ascorbate (1.3 μM), and Sodium pyruvate (2.4 μM) added just prior to use. Sections were moved to HEPES-buffered ACSF containing 10 mM HEPES, 140 mM NaCl, 24 mM $NaHCO_3$, 3 mM KC1, 1.25 mM $NaH_2PO_4$, 1.25 mM $MgCl_2$, 2 mM $CaCl_2$, and recovered for 90 minutes. Surface biotinylation was performed as previously described with modifications (Kim and Kovacs, 2011). HEPES-buffered ACSF was used for all low-calcium incubations and washes. Incubation with NHS-LC-Sulfo-Biotin (Thermo) was quenched after 45 minutes. Cortical areas were separated from Hippocampal and subcortical structures prior to being flash-frozen in liquid nitrogen and stored at −80° C. until protein extraction and pull-down. Extraction buffer containing 10 mm Tris, 150 mm NaCl, 1% TritonX-100, 0.2% SDS, and 0.5% Sodium Deoxycholate, and 1 mm EDTA was added to samples and heavy membranes and debris were pelleted by centrifugation at 12000 g for 15 minutes at 4° C. prior to sonication. Protein concentration was determined by BCA method. NeurAvidin beads were prepared in 1 mL of Extraction buffer with Protease Inhibitor Cocktail (Sigma) added. 1 mg of protein was added to the sample and rotated for 3 hours at 4° C. For total protein samples, 200 ug protein was diluted in extraction buffer and SDS loading dye and frozen at −20° C. until use. EDTA concentration was increased to 50 mM for isolation of Fmr1.

Western Blot—Protein samples were separated by polyacrylamide gel electrophoresis on 5% and 8% acrylamide gels and wet transferred to Immobilon membranes (Millipore). TBST with 5% non-fat dry milk (Apex) was used to block and primary antibody was diluted in blocking buffer for overnight incubation at 4° C. Blots were washed with TBST and incubated with HRP-conjugated secondary antibody for 2 hours at room temperature. Bands were visualized using West Pico Chemiluminescent Substrate and exposed to film at intervals ranging from 30 seconds to 2 hours.

Antibodies—Primary antibodies were mouse anti-Lgl1, mouse anti-Lgl1 (Novus), Goat anti Vang12 Antibody (N-13, Santa Cruz, sc-46561), goat anti-JAM-C (R&D Systems), mouse anti-GAPDH (Abcam), and rabbit anti-GFP (Invitrogen), and chicken anti-MAP2 (Abcam). Secondary antibodies used in western blot were HRP-conjugated donkey anti-mouse, anti-goat, and anti-rabbit. For immunofluorescence, AF568-conjugated Donkey anti-Mouse (Invitrogen), AF488-conjugated Donkey anti-Chicken (Jackson Immunoresearch), AF488-conjugated Donkey anti-Rabbit (Invitrogen), AF647-conjugated Donkey anti-Rabbit (Invitrogen).

Cell filling and spine analysis—Mice were perfused, sectioned, and labeled with AlexaFluor Hydrazide as previously described (Dumitriu et al., 2011). SLICK-H$I^{flox/flox}$ pups were i.p. injected with tamoxifen at P7-8. At P14, pups were anesthetized with a ketamine/xylazine cocktail followed by transcardial perfusion with room temperature 4% PFA, postfixed for one hour in 4% PFA, vibratome sectioned at 100 μm, and then postfixed again for 10 minutes. AlexaFluor Hydrazide 555 (Invitrogen, 10 mM in 200 mM KC1) was injected into dendritic segments ionophoretically by filling the cell with fluorescent dye. Sections were briefly fixed for 15 minutes to preserve the fluorescent label. Immunolabeling with GFP antibody (Invitrogen) was used to confirm that the fluorescently filled dendrite is YFP+. 30-40 μm segments of CA1 oblique apical dendrites, which are located 100-200 μm from the CA1 pyramidal neuron cell bodies in the stratum radiatum, were analyzed. These spines represented the postsynaptic structures of the Schaffer collateral-CA1 synapses.

The maximum spine length and head width were measured manually with Image J (NIH) to characterize spine shape as previously described (Bochner et al., 2014; Calfa et al., 2012; Harris et al., 1992; Tang et al., 2014; Vogel-Ciernia et al., 2013). Spines with heads equal to or less than the head width were categorized as “thin”, and those with heads greater than the neck width were categorized as “mushroom”. Spines without a neck that had a width longer than their lengths were termed “stubby”. Spines with one neck and a branch point resulting in 2 heads were termed “branched”. Protrusions not clearly seen or with lengths >5 μm were excluded from analysis. Both image acquisition and morphometric analyses were done by experimenters blinded to the genotypes of the animals. Results were compared between littermates and then pooled by genotypes to assess the influence of prenatal care.

Tissue preparation—Animals were anesthetized i.p. with a ketamine/xylazine cocktail and perfused with ice-cold PBS followed by 4% Paraformaldehyde (PFA). Brains were post-fixed in 4% PFA overnight and moved to 30% sucrose until equilibrated. Frozen section embedded in OCT medium and Sucrose were sectioned at 40 μm on a Leica C M 3050 S cryostat. Slides were stored at 4° C. until immunostaining.

Immunostaining—For tissue sections, slides were rehydrated with 2 washes of PBS and permeabilized with PBS+ 0.3% Triton X-100. Slides were blocked with 5% normal donkey serum for 2 hours at room temperature. Primary antibody was incubated at 4° C. overnight and secondary antibody was incubated for 2 hours at room temperature. Slides were coverslip with Fluoromount-G (Southern Biotech) and stored at 4° C.

For cultured neurons, glass coverslips with primary cell cultures were washed with PBS and permeabilized with PBS+0.1% Triton X-100. Coverslips were blocked with PBS containing 2% BSA, 2% Fetal Bovine Serum, and 0.1% Triton X-100. Primary antibody was incubated at 4° C. overnight and secondary antibody was incubated for 2 hours at room temperature. Coverslips were inverted onto slides with Fluoromount-G (Southern Biotech) and stored at 4° C.

Statistical Analysis—Statistical analysis was performed using Prism 6 (GraphPad). Student's T-test with Welch's correction was used for comparison between control and Lgl1 mutant animals unless otherwise noted. Graphs of quantitative data present individual data points for animals with mean and standard error of the mean indicated unless otherwise noted. The Kolmogorov-Smirnov test was used to compare distribution of measurements of synaptic ultrastructure.

REFERENCES

Antunes, M., and Biala, G. (2012). The novel object recognition memory: neurobiology, test procedure, and its modifications. Cogn Process 13, 93-110.

Berkel, et al., (2010). Mutations in the SHANK2 synaptic scaffolding gene in autism spectrum disorder and mental retardation. Nature Genetics 42, 489.

Betschinger, J., Mechtler, K., and Knoblich, J. A. (2003). The Par complex directs asymmetric cell division by phosphorylating the cytoskeletal protein Lgl. Nature 422, 326-330.

Bochner, et al. (2014). Blocking PirB up-regulates spines and functional synapses to unlock visual cortical plasticity and facilitate recovery from amblyopia. Sci Transl Med 6, 258ra140.

Calfa, et al. (2012). HDAC activity is required for BDNF to increase quantal neurotransmitter release and dendritic spine density in CA1 pyramidal neurons. Hippocampus 22, 1493-1500.

Chen, et al. (1997). Homologous recombination of a flanking repeat gene cluster is a mechanism for a common contiguous gene deletion syndrome. Nature Genetics 17, 154-163.

Chen, et al. (1996). The Smith-Magenis Syndrome [del (17)p11.2]: Clinical Review and Molecular Advances. Mental Retardation and Developmental Disabilities Research Reviews 2, 122-129.

Cohen, et al. (1977). The structure of postsynaptic densities isolated from dog cerebral cortex: I. overall morphology and protein composition. Journal of Cell Biology 74, 181-203.

Collingridge, G., Kehl, S., and McLennan, H. (1983). Excitatory amino acids in synaptic transmission in the Schaffer collateral-commissural pathway of the rat hippocampus. Journal of Physiology 334, 33-46.

Dominguez, et al. (2013). The Imaginary Part of Coherency in Autism: Differences in Cortical Functional Connectivity in Preschool Children. PLOS One 8, 1-13.

Dumitriu, D., Rodriguez, A., and Morrison, J. (2011). High-throughput, detailed, cell-specific neuroanatomy of dendritic spines using microinjection and confocal microscopy. Nature Protocols 6, 1391-1411.

Durand, et al. (2007). Mutations in the gene encoding the synaptic scaffolding protein SHANK3 are associated with autism spectrum disorders. Nature Genetics 39, 25-27.

Dykens, E., Finucane, B., and Gayley, C. (1997). Brief Report: Cognitive and Behavioral Profiles in Persons with Smith-Magenis Syndrome. Journal of Autism and Developmental Disorders 27.

Dykens, E., and Smith, A. C. M. (1998). Distinctiveness and correlates of maladaptive behaviour in children and adolescents with Smith-Magenis syndrome. Journal of Intellectual Disability Research 42, 481-489.

Ebnet, et al. (2003). The junctional adhesion molecule (JAM) family members JAM-2 and JAM-3 associate with the cell polarity protein PAR-3: a possible role for JAMs in endothelial cell polarity. Journal of Cell Science 116, 3879-3891.

Edelman, et al. (2007). Gender, genotype, and phenotype differences in Smith-Magenis syndrome: a meta-analysis of 105 cases. Clinical Genetics 71.

Ehrlich, I., and Malinow, R. (2004). Postsynaptic Density 95 controls AMPA Receptor Incorporation during Long-Term Potentiation and Experience-Driven Synaptic Plasticity. J Neurosci 24, 916-927.

Georgiou, et al. (2008). Cdc42, Par6, and aPKC Regulate Arp2/3-Mediated Endocytosis to Control Local Adherens Junction Stability. Current Biology 18, 1631-1638.

Girirajan, et al. (2006). Genotype-phenotype correlation in Smith-Magenis syndrome: Evidence that multiple genes in 17p11.2 contribute to the clinical spectrum. Genetics in Medicine 8, 417-427.

Gould, T., Dao, D., and Kovacsics, C. (2009). The Open Field Test. Mood and Anxiety Related Phenotypes in Mice 42, 1-20.

Greenberg, et al. (1996). Multi-Disciplinary Clinical Study of Smith-Magenis Syndrome (Deletion 17p11.2). Am J Med Genet 62, 247-254.

Gropman, et al. (2007). New developments in Smith-Magenis syndrome (del 17p11.2). Current Opinion in Neurology 20, 125-134.

Harris, et al. (1992). Three-dimensional structure of dendritic spines and synapses in rat hippocampus (CA1) at postnatal day 15 and adult ages: implications for the maturation of synaptic physiology and long-term potentiation. Journal of Neuroscience 12, 2685-2705.

Heimer-McGinn, V., and Young, P. (2011). Efficient inducible Pan-neuronal cre-mediated recombination in SLICK-H transgenic mice. Genesis 49, 942-949.

Huang, et al. (2016). Molecular and Neural Functions of Rail, the Causal Gene for Smith-Magenis Syndrome. Neuron 92, 1-15.

Hung, et al. (2008). Smaller Dendritic Spines, Weaker Synaptic Transmission, but Enhanced Spatial Learning in Mice Lacking Shank1. The Journal of Neuroscience 28, 1697-1708.

Irifune, M., Shimizu, T., and Nomoto, M. (1991). Ketamine-Induced Hyperlocomotion Associated with Alteration of Presynaptic Components of Dopamine Neurons in Nucleus Accumbens of Mice. Pharmacology Biochemistry and Behavior 40, 399-407.

Jeyifous, et al. (2009). SAP97 and CASK mediate sorting of NMDA receptors through a previously unknown secretory pathway. Nature Neuroscience 12, 1011-1019.

Karner, C., Wharton, K.A., and Carroll, T.J. (2006). Apical-basal polarity, Wnt signaling and vertebrate organogenesis. Semin Cell Dev Biol 17, 214-222.

Keown, et al. (2013). Local Functional Overconnectivity in Posterior Brain Regions Is Associated with Symptom Severity in Autism Spectrum Disorders. Cell Reports 5, 567-572.

Kim, D., and Kovacs, D. (2011). Surface Trafficking of Sodium Channels in Cells and in Hippocampal Slices. Methods Mol Biol 793, 351-361.

Kim, E., and Sheng, M. (2004). PDZ domain proteins of synapses. Nature Reviews Neuroscience 5, 771-781.

Klezovitch, et al. (2004). Loss of cell polarity causes severe brain dysplasia in Lgl1 knockout mice. Genes & Development 18, 559-571.

Koyama, et al. (1996). The human homologue of the murine Llglh gene (LLGL) maps within the Smith-Magenis syndrome region in 17p11.2. Cytogenetic and Genome Research 72, 78-82.

Laje, G., Morse, R., Richter, W., Ball, J., Pao, M., and Smith, A. (2010). Autism spectrum features in Smith-Magenis syndrome. Am J Med Genet C Semin Med Genet 154, 456-462.

Leonard, et al. (1998). SAP97 Is Associated with the a-Amino-3-hydroxy-5-methylisoxazole-4-propionic Acid Receptor GluR1 Subunit. Journal of Biological Chemistry 273, 19518-19524.

Li, X., Morrow, D., and Witkin, J. (2006). Decreases in nestlet shredding of mice by serotonin uptake inhibitors: Comparison with marble burying. Life Sci 78, 1933-1939.

Li, Z., and Sheng, M. (2003). Some assembly required: the development of neuronal synapses. *Nature Reviews Molecular Cell Biology* 4, 833-841.

Lin, et al. (2004). Postsynaptic Density Protein-95 Regulates NMDA Channel Gating and Surface Expression. J Neuro sci 24, 10138-10148.

Macara, I. G. (2004). Parsing the Polarity Code. *Nature Reviews Molecular Cell Biology* 5, 220-231.

Martin, S., Wolters, P., and Smith, A. (2006). Adaptive and Maladaptive Behavior in Children with Smith-Magenis Syndrome. Journal of Autism and Developmental Disorders 36,541-552.

Meffert, et al. (2003). NF-kappa B functions in synaptic signaling and behavior. Nature Neuroscience 6.

Mei, et al. (2016). Adult restoration of Shank3 expression rescues selective autistic-like phenotypes. Nature 530, 481-484.

Missler, M., Sudhof, T. C., and Biederer, T. (2012). Synaptic Cell Adhesion. Cold Spring Harbor Perspectives in Biology 4.

Monaghan, D. T., Bridges, R. J., and Cotman, C. W. (1989). The Excitatory Amino Acid Receptors: Their Classes, Pharmacology, and Distinct Properties in the Function of the Central Nervous System. Annual Review of Pharmacology and Toxicology 29, 365-402.

Müller, et al. (1996). SAP102, a novel postsynaptic protein that interacts with NMDA receptor complexes in vivo. Neuron 17, 255-265.

Patel, et al. (2014). An open-source toolbox for automated phenotyping of mice in behavioral tasks. Frontiers in Behavioral Neuroscience 8,1-16.

Peça, et al. (2011). Shank3 mutant mice display autistic like behaviours and striatal dysfunction. Nature 472, 437-442.

Phelan, et al. (2001). 22q13 deletion syndrome. Am J Med Genet 101, 91-99.

Potocki, et al. (2003). Variability in clinical phenotype despite common chromosomal deletion in Smith-Magenis syndrome[del(17)(p11.2p11.2)]. Genet Med 5, 430-434.

Prybylowski, et al. (2005). The Synaptic Localization of NR2B-Containing NMDA Receptors Is Controlled by Interactions with PDZ Proteins and AP-2. PNAS 109, 7499-7504.

Sans, et al. (2000). A Developmental Change in NMDA Receptor-Associated Proteins at Hippocampal Synapses. J Neurosci 20, 1260-1271.

Sato, et al. (2012). SHANK1 Deletions in Males with Autism Spectrum Disorder. The American Journal of Human Genetics 90, 879-887.

Schmeisser, et al. (2012). Autistic-like behaviours and hyperactivity in mice lacking ProSAP1/Shank2. Nature 486, 256-260.

Sheng, M., and Kim, E. (2011). The Postsynaptic Organization of Synapses. Cold Spring Harbor Perspectives in Biology 3.

Smith A C, Dykens E, and F, G. (1998). Behavioral phenotype of Smith-Magenis syndrome (del 17p11.2). Am J Med Genet 81, 179-185.

Smith, et al. (1986). Interstitial deletion of (17) (p11.2p11.2) in nine patients. American Journal of Medical Genetics 24, 393-414.

Soorya, et al. (2013). Prospective investigation of autism and genotype-phenotype correlations in 22q13 deletion syndrome and SHANK3 deficiency. Molec Autism 4, doi: 10.1186/2040-2392-1184-1118.

Sudhof, T. C. (2012). The presynaptic active zone. Neuron 75, 11-25.

Supekar, et al. (2013). Brain Hyperconnectivity in Children with Autism and its Links to Social Deficits. Cell Reports 5, 738-747.

Tang, et al. (2014). Loss of mTOR-dependent macroautophagy causes autistic-like synaptic pruning deficits. Neuron 83, 1131-1143.

Tao, et al. (2003). Impaired NMDA receptor-mediated postsynaptic function and blunted NMDA receptor-dependent persistent pain in mice lacking postsynaptic density-93 protein. J Neurosci 23, 6703-6712.

Thakar, et al. (2017). Evidence for opposing roles of Celsr3 and Vang12 in glutamatergic synapse formation. PNAS 114, E610-E618.

Vlangos, et al. (2003). Refinement of the Smith—Magenis syndrome critical region to 950 kb and assessment of 17p11.2 deletions. Are all deletions created equally? Molecular Genetics and Metabolism 79, 134-141.

Vogel-Ciernia, et al. (2013). The neuron-specific chromatin regulatory subunit BAF53b is necessary for synaptic plasticity and memory. Nat Neurosci 16, 552-561.

Wang, et al. (2007). Changes in hippocampal synapses and learning-memory abilities in age-increasing rats and effects of tetrahydroxystilbene glucoside in aged rats. Neuroscience 149, 739-746.

Watkins, J. C., and Evans, R. H. (1981). Excitatory amino acid transmitters. Annu Rev Pharmacol Toxicol 21, 165-204.

Wessel, D., and Flügge, U. (1984). A method for the quantitative recovery of protein in dilute solution in the presence of detergents and lipids. Anal Biochem 138, 141-143.

Xiao, et al, (1998). Homer regulates the association of group 1 metabotropic receptors with multivalent complexes of Homer-related, synaptic proteins. Neuron 21, 707-716.

Yamanaka, et al. (2006). Lgl mediates apical domain disassembly by suppressing the PAR-3-aPKC-PAR-6 complex to orient apical membrane polarity. Journal of Cell Science 119, 2107-2118.

Yamanaka, et al. (2003). Mammalian Lgl Forms a Protein Complex with PAR-6 and aPKC Independently of PAR-3 to Regulate Epithelial Cell Polarity. Current Biology 13, 734-743.

Yang, M., Silverman, J., and Crawley, J. (2011). Automated Three-Chambered Social Approach Task for Mice. Curr Protoc Neurosci 8, Unit 8.26.

Young, et al. (2008). Single-neuron labeling with inducible cre-mediated knockout in transgenic mice. Nature Neurscience 11, 721-728.

Zarnescu, et al. (2005). Fragile X protein functions with lgl and the PAR complex in flies and mice. Dev Cell 8, 43-52.

Zhu, et al. (2016). Mechanistic basis of MAGUK-organized complexes in synaptic development and signaling. Nat Rev Neurosci 17, 209-223.

Although the invention has been described with reference to the above example, it will be understood that modifications and variations are encompassed within the spirit and scope of the invention. Accordingly, the invention is limited only by the following claims.

What is claimed is:

1. A method for alleviating a social interaction deficit in a subject with a neurodegenerative disease or behavioral disorder, the neurodegenerative disease or behavioral disorder associated with lethal giant larvae (Lgl1) induced increase in synapses in a population of neurons in the subject's brain, comprising administering to the subject a subanesthetic amount of an N-methyl-D-aspartate (NMDA) receptor antagonist;

wherein the NMDA receptor antagonist is selected from the group consisting of ketamine, memantine, dizocilpine (MK-801), dextromethorphan (DXM), phencyclidine (PCP), methoxetamine (MXE), and nitrous oxide ($N_2O$);

wherein the neurodegenerative disease or behavioral disorder is selected from the group consisting of Smith-Magenis Syndrome (SMS) and attention deficit hyperactivity disorder (ADHD).

2. The method of claim 1, wherein the NMDA receptor antagonist increases the AMPA/NMDA ratio in the neurons.

3. The method of claim 1, wherein the method further comprises contacting the population of neurons with an atypical protein kinase c (aPKC) inhibitor comprising Lgl1 protein.

4. A method of managing or treating a social interaction deficit in a subject with a neurodegenerative disease or behavioral disorder in a subject, comprising administering to the subject a subanesthetic amount of an N-methyl-D-aspartate (NMDA) receptor antagonist;

wherein the NMDA receptor antagonist is selected from the group consisting of ketamine, memantine, dizocilpine (MK-801), dextromethorphan (DXM), phencyclidine (PCP), methoxetamine (MXE), and nitrous oxide ($N_2O$);

wherein the neurodegenerative disease or behavioral disorder is selected from the group consisting of Smith-Magenis Syndrome (SMS) and attention deficit hyperactivity disorder (ADHD).

5. The method of claim 4, wherein the method further comprises administering to the subject an atypical protein kinase c (aPKC) inhibitor comprising Lgl1 protein.

* * * * *

SEQUENCE LISTING

<160> NUMBER OF SEQ ID NOS: 10

<210> SEQ ID NO 1
<211> LENGTH: 596
<212> TYPE: PRT
<213> ORGANISM: Homo sapiens

<400> SEQUENCE: 1

Met Pro Thr Gln Arg Asp Ser Ser Thr Met Ser His Thr Val Ala Gly
1 5 10 15

Gly Gly Ser Gly Asp His Ser His Gln Val Arg Val Lys Ala Tyr Tyr
20 25 30

Arg Gly Asp Ile Met Ile Thr His Phe Glu Pro Ser Ile Ser Phe Glu
35 40 45

Gly Leu Cys Asn Glu Val Arg Asp Met Cys Ser Phe Asp Asn Glu Gln
50 55 60

Leu Phe Thr Met Lys Trp Ile Asp Glu Glu Gly Asp Pro Cys Thr Val
65 70 75 80

Ser Ser Gln Leu Glu Leu Glu Glu Ala Phe Arg Leu Tyr Glu Leu Asn
85 90 95

Lys Asp Ser Glu Leu Leu Ile His Val Phe Pro Cys Val Pro Glu Arg
100 105 110

Pro Gly Met Pro Cys Pro Gly Glu Asp Lys Ser Ile Tyr Arg Arg Gly
115 120 125

Ala Arg Arg Trp Arg Lys Leu Tyr Cys Ala Asn Gly His Thr Phe Gln
130 135 140

Ala Lys Arg Phe Asn Arg Arg Ala His Cys Ala Ile Cys Thr Asp Arg
145 150 155 160

Ile Trp Gly Leu Gly Arg Gln Gly Tyr Lys Cys Ile Asn Cys Lys Leu
165 170 175

Leu Val His Lys Lys Cys His Lys Leu Val Thr Ile Glu Cys Gly Arg
180 185 190

His Ser Leu Pro Gln Glu Pro Val Met Pro Met Asp Gln Ser Ser Met
195 200 205

His Ser Asp His Ala Gln Thr Val Ile Pro Tyr Asn Pro Ser Ser His
210 215 220

Glu Ser Leu Asp Gln Val Gly Glu Glu Lys Glu Ala Met Asn Thr Arg
225 230 235 240

Glu Ser Gly Lys Ala Ser Ser Ser Leu Gly Leu Gln Asp Phe Asp Leu
245 250 255

Leu Arg Val Ile Gly Arg Gly Ser Tyr Ala Lys Val Leu Leu Val Arg
260 265 270

Leu Lys Lys Thr Asp Arg Ile Tyr Ala Met Lys Val Val Lys Lys Glu
275 280 285

Leu Val Asn Asp Asp Glu Asp Ile Asp Trp Val Gln Thr Glu Lys His
290 295 300

Val Phe Glu Gln Ala Ser Asn His Pro Phe Leu Val Gly Leu His Ser
305 310 315 320

Cys Phe Gln Thr Glu Ser Arg Leu Phe Phe Val Ile Glu Tyr Val Asn
325 330 335

Gly Gly Asp Leu Met Phe His Met Gln Arg Gln Arg Lys Leu Pro Glu
340 345 350

Glu His Ala Arg Phe Tyr Ser Ala Glu Ile Ser Leu Ala Leu Asn Tyr
355 360 365

```
Leu His Glu Arg Gly Ile Ile Tyr Arg Asp Leu Lys Leu Asp Asn Val
    370                 375                 380

Leu Leu Asp Ser Glu Gly His Ile Lys Leu Thr Asp Tyr Gly Met Cys
385                 390                 395                 400

Lys Glu Gly Leu Arg Pro Gly Asp Thr Thr Ser Thr Phe Cys Gly Thr
                405                 410                 415

Pro Asn Tyr Ile Ala Pro Glu Ile Leu Arg Gly Glu Asp Tyr Gly Phe
            420                 425                 430

Ser Val Asp Trp Trp Ala Leu Gly Val Leu Met Phe Glu Met Met Ala
        435                 440                 445

Gly Arg Ser Pro Phe Asp Ile Val Gly Ser Ser Asp Asn Pro Asp Gln
    450                 455                 460

Asn Thr Glu Asp Tyr Leu Phe Gln Val Ile Leu Glu Lys Gln Ile Arg
465                 470                 475                 480

Ile Pro Arg Ser Leu Ser Val Lys Ala Ala Ser Val Leu Lys Ser Phe
                485                 490                 495

Leu Asn Lys Asp Pro Lys Glu Arg Leu Gly Cys His Pro Gln Thr Gly
            500                 505                 510

Phe Ala Asp Ile Gln Gly His Pro Phe Phe Arg Asn Val Asp Trp Asp
        515                 520                 525

Met Met Glu Gln Lys Gln Val Val Pro Pro Phe Lys Pro Asn Ile Ser
    530                 535                 540

Gly Glu Phe Gly Leu Asp Asn Phe Asp Ser Gln Phe Thr Asn Glu Pro
545                 550                 555                 560

Val Gln Leu Thr Pro Asp Asp Asp Asp Ile Val Arg Lys Ile Asp Gln
                565                 570                 575

Ser Glu Phe Glu Gly Phe Glu Tyr Ile Asn Pro Leu Leu Met Ser Ala
            580                 585                 590

Glu Glu Cys Val
        595


<210> SEQ ID NO 2
<211> LENGTH: 592
<212> TYPE: PRT
<213> ORGANISM: Homo sapiens

<400> SEQUENCE: 2

Met Pro Ser Arg Thr Gly Pro Lys Met Glu Gly Ser Gly Gly Arg Val
1               5                   10                  15

Arg Leu Lys Ala His Tyr Gly Gly Asp Ile Phe Ile Thr Ser Val Asp
            20                  25                  30

Ala Ala Thr Thr Phe Glu Glu Leu Cys Glu Glu Val Arg Asp Met Cys
        35                  40                  45

Arg Leu His Gln Gln His Pro Leu Thr Leu Lys Trp Val Asp Ser Glu
    50                  55                  60

Gly Asp Pro Cys Thr Val Ser Ser Gln Met Glu Leu Glu Glu Ala Phe
65                  70                  75                  80

Arg Leu Ala Arg Gln Cys Arg Asp Glu Gly Leu Ile Ile His Val Phe
                85                  90                  95

Pro Ser Thr Pro Glu Gln Pro Gly Leu Pro Cys Pro Gly Glu Asp Lys
            100                 105                 110

Ser Ile Tyr Arg Arg Gly Ala Arg Arg Trp Arg Lys Leu Tyr Arg Ala
        115                 120                 125

Asn Gly His Leu Phe Gln Ala Lys Arg Phe Asn Arg Arg Ala Tyr Cys
    130                 135                 140
```

-continued

```
Gly Gln Cys Ser Glu Arg Ile Trp Gly Leu Ala Arg Gln Gly Tyr Arg
145                 150                 155                 160

Cys Ile Asn Cys Lys Leu Leu Val His Lys Arg Cys His Gly Leu Val
                165                 170                 175

Pro Leu Thr Cys Arg Lys His Met Asp Ser Val Met Pro Ser Gln Glu
            180                 185                 190

Pro Pro Val Asp Asp Lys Asn Glu Asp Ala Asp Leu Pro Ser Glu Glu
        195                 200                 205

Thr Asp Gly Ile Ala Tyr Ile Ser Ser Ser Arg Lys His Asp Ser Ile
    210                 215                 220

Lys Asp Asp Ser Glu Asp Leu Lys Pro Val Ile Asp Gly Met Asp Gly
225                 230                 235                 240

Ile Lys Ile Ser Gln Gly Leu Gly Leu Gln Asp Phe Asp Leu Ile Arg
                245                 250                 255

Val Ile Gly Arg Gly Ser Tyr Ala Lys Val Leu Leu Val Arg Leu Lys
            260                 265                 270

Lys Asn Asp Gln Ile Tyr Ala Met Lys Val Val Lys Lys Glu Leu Val
        275                 280                 285

His Asp Asp Glu Asp Ile Asp Trp Val Gln Thr Glu Lys His Val Phe
    290                 295                 300

Glu Gln Ala Ser Ser Asn Pro Phe Leu Val Gly Leu His Ser Cys Phe
305                 310                 315                 320

Gln Thr Thr Ser Arg Leu Phe Leu Val Ile Glu Tyr Val Asn Gly Gly
                325                 330                 335

Asp Leu Met Phe His Met Gln Arg Gln Arg Lys Leu Pro Glu Glu His
            340                 345                 350

Ala Arg Phe Tyr Ala Ala Glu Ile Cys Ile Ala Leu Asn Phe Leu His
        355                 360                 365

Glu Arg Gly Ile Ile Tyr Arg Asp Leu Lys Leu Asp Asn Val Leu Leu
    370                 375                 380

Asp Ala Asp Gly His Ile Lys Leu Thr Asp Tyr Gly Met Cys Lys Glu
385                 390                 395                 400

Gly Leu Gly Pro Gly Asp Thr Thr Ser Thr Phe Cys Gly Thr Pro Asn
                405                 410                 415

Tyr Ile Ala Pro Glu Ile Leu Arg Gly Glu Glu Tyr Gly Phe Ser Val
            420                 425                 430

Asp Trp Trp Ala Leu Gly Val Leu Met Phe Glu Met Met Ala Gly Arg
        435                 440                 445

Ser Pro Phe Asp Ile Ile Thr Asp Asn Pro Asp Met Asn Thr Glu Asp
    450                 455                 460

Tyr Leu Phe Gln Val Ile Leu Glu Lys Pro Ile Arg Ile Pro Arg Phe
465                 470                 475                 480

Leu Ser Val Lys Ala Ser His Val Leu Lys Gly Phe Leu Asn Lys Asp
                485                 490                 495

Pro Lys Glu Arg Leu Gly Cys Arg Pro Gln Thr Gly Phe Ser Asp Ile
            500                 505                 510

Lys Ser His Ala Phe Phe Arg Ser Ile Asp Trp Asp Leu Leu Glu Lys
        515                 520                 525

Lys Gln Ala Leu Pro Pro Phe Gln Pro Gln Ile Thr Asp Asp Tyr Gly
    530                 535                 540

Leu Asp Asn Phe Asp Thr Gln Phe Thr Ser Glu Pro Val Gln Leu Thr
545                 550                 555                 560
```

```
Pro Asp Asp Glu Asp Ala Ile Lys Arg Ile Asp Gln Ser Glu Phe Glu
                565                 570                 575

Gly Phe Glu Tyr Ile Asn Pro Leu Leu Leu Ser Thr Glu Glu Ser Val
            580                 585                 590


<210> SEQ ID NO 3
<211> LENGTH: 409
<212> TYPE: PRT
<213> ORGANISM: Homo sapiens

<400> SEQUENCE: 3

Met Asp Ser Val Met Pro Ser Gln Glu Pro Pro Val Asp Asp Lys Asn
1               5                   10                  15

Glu Asp Ala Asp Leu Pro Ser Glu Glu Thr Asp Gly Ile Ala Tyr Ile
            20                  25                  30

Ser Ser Ser Arg Lys His Asp Ser Ile Lys Asp Asp Ser Glu Asp Leu
        35                  40                  45

Lys Pro Val Ile Asp Gly Met Asp Gly Ile Lys Ile Ser Gln Gly Leu
    50                  55                  60

Gly Leu Gln Asp Phe Asp Leu Ile Arg Val Ile Gly Arg Gly Ser Tyr
65                  70                  75                  80

Ala Lys Val Leu Leu Val Arg Leu Lys Lys Asn Asp Gln Ile Tyr Ala
                85                  90                  95

Met Lys Val Val Lys Lys Glu Leu Val His Asp Asp Glu Asp Ile Asp
            100                 105                 110

Trp Val Gln Thr Glu Lys His Val Phe Glu Gln Ala Ser Ser Asn Pro
        115                 120                 125

Phe Leu Val Gly Leu His Ser Cys Phe Gln Thr Thr Ser Arg Leu Phe
    130                 135                 140

Leu Val Ile Glu Tyr Val Asn Gly Gly Asp Leu Met Phe His Met Gln
145                 150                 155                 160

Arg Gln Arg Lys Leu Pro Glu Glu His Ala Arg Phe Tyr Ala Ala Glu
                165                 170                 175

Ile Cys Ile Ala Leu Asn Phe Leu His Glu Arg Gly Ile Ile Tyr Arg
            180                 185                 190

Asp Leu Lys Leu Asp Asn Val Leu Leu Asp Ala Asp Gly His Ile Lys
        195                 200                 205

Leu Thr Asp Tyr Gly Met Cys Lys Glu Gly Leu Gly Pro Gly Asp Thr
    210                 215                 220

Thr Ser Thr Phe Cys Gly Thr Pro Asn Tyr Ile Ala Pro Glu Ile Leu
225                 230                 235                 240

Arg Gly Glu Glu Tyr Gly Phe Ser Val Asp Trp Trp Ala Leu Gly Val
                245                 250                 255

Leu Met Phe Glu Met Met Ala Gly Arg Ser Pro Phe Asp Ile Ile Thr
            260                 265                 270

Asp Asn Pro Asp Met Asn Thr Glu Asp Tyr Leu Phe Gln Val Ile Leu
        275                 280                 285

Glu Lys Pro Ile Arg Ile Pro Arg Phe Leu Ser Val Lys Ala Ser His
    290                 295                 300

Val Leu Lys Gly Phe Leu Asn Lys Asp Pro Lys Glu Arg Leu Gly Cys
305                 310                 315                 320

Arg Pro Gln Thr Gly Phe Ser Asp Ile Lys Ser His Ala Phe Phe Arg
                325                 330                 335

Ser Ile Asp Trp Asp Leu Leu Glu Lys Lys Gln Ala Leu Pro Pro Phe
            340                 345                 350
```

-continued

```
Gln Pro Gln Ile Thr Asp Asp Tyr Gly Leu Asp Asn Phe Asp Thr Gln
        355                 360                 365

Phe Thr Ser Glu Pro Val Gln Leu Thr Pro Asp Asp Glu Asp Ala Ile
    370                 375                 380

Lys Arg Ile Asp Gln Ser Glu Phe Glu Gly Phe Glu Tyr Ile Asn Pro
385                 390                 395                 400

Leu Leu Leu Ser Thr Glu Glu Ser Val
                405


<210> SEQ ID NO 4
<211> LENGTH: 524
<212> TYPE: PRT
<213> ORGANISM: Homo sapiens

<400> SEQUENCE: 4

Met Asp Thr Glu Ser Thr Tyr Ser Gly Tyr Ser Tyr Tyr Ser Ser His
1               5                   10                  15

Ser Lys Lys Ser His Arg Gln Gly Glu Arg Thr Arg Glu Arg His Lys
            20                  25                  30

Ser Pro Arg Asn Lys Asp Gly Arg Gly Ser Glu Lys Ser Val Thr Ile
        35                  40                  45

Gln Pro Pro Thr Gly Glu Pro Leu Leu Gly Asn Asp Ser Thr Arg Thr
    50                  55                  60

Glu Glu Val Gln Asp Asp Asn Trp Gly Glu Thr Thr Thr Ala Ile Thr
65                  70                  75                  80

Gly Thr Ser Glu His Ser Ile Ser Gln Glu Asp Ile Ala Arg Ile Ser
                85                  90                  95

Lys Asp Met Glu Asp Ser Val Gly Leu Asp Cys Lys Arg Tyr Leu Gly
            100                 105                 110

Leu Thr Val Ala Ser Phe Leu Gly Leu Leu Val Phe Leu Thr Pro Ile
        115                 120                 125

Ala Phe Ile Leu Leu Pro Pro Ile Leu Trp Arg Asp Glu Leu Glu Pro
    130                 135                 140

Cys Gly Thr Ile Cys Glu Gly Leu Phe Ile Ser Met Ala Phe Lys Leu
145                 150                 155                 160

Leu Ile Leu Leu Ile Gly Thr Trp Ala Leu Phe Phe Arg Lys Arg Arg
                165                 170                 175

Ala Asp Met Pro Arg Val Phe Val Phe Arg Ala Leu Leu Leu Val Leu
            180                 185                 190

Ile Phe Leu Phe Val Val Ser Tyr Trp Leu Phe Tyr Gly Val Arg Ile
        195                 200                 205

Leu Asp Ser Arg Asp Arg Asn Tyr Gln Gly Ile Val Gln Tyr Ala Val
    210                 215                 220

Ser Leu Val Asp Ala Leu Leu Phe Ile His Tyr Leu Ala Ile Val Leu
225                 230                 235                 240

Leu Glu Leu Arg Gln Leu Gln Pro Met Phe Thr Leu Gln Val Val Arg
                245                 250                 255

Ser Thr Asp Gly Glu Ser Arg Phe Tyr Ser Leu Gly His Leu Ser Ile
            260                 265                 270

Gln Arg Ala Ala Leu Val Val Leu Glu Asn Tyr Tyr Lys Asp Phe Thr
        275                 280                 285

Ile Tyr Asn Pro Asn Leu Leu Thr Ala Ser Lys Phe Arg Ala Ala Lys
    290                 295                 300

His Met Ala Gly Leu Lys Val Tyr Asn Val Asp Gly Pro Ser Asn Asn
```

-continued

```
305                 310                 315                 320

Ala Thr Gly Gln Ser Arg Ala Met Ile Ala Ala Ala Ala Arg Arg Arg
                325                 330                 335

Asp Ser Ser His Asn Glu Leu Tyr Tyr Glu Glu Ala Glu His Glu Arg
            340                 345                 350

Arg Val Lys Lys Arg Lys Ala Arg Leu Val Val Ala Val Glu Glu Ala
        355                 360                 365

Phe Ile His Ile Gln Arg Leu Gln Ala Glu Glu Gln Gln Lys Ala Pro
    370                 375                 380

Gly Glu Val Met Asp Pro Arg Glu Ala Ala Gln Ala Ile Phe Pro Ser
385                 390                 395                 400

Met Ala Arg Ala Leu Gln Lys Tyr Leu Arg Ile Thr Arg Gln Gln Asn
                405                 410                 415

Tyr His Ser Met Glu Ser Ile Leu Gln His Leu Ala Phe Cys Ile Thr
            420                 425                 430

Asn Gly Met Thr Pro Lys Ala Phe Leu Glu Arg Tyr Leu Ser Ala Gly
        435                 440                 445

Pro Thr Leu Gln Tyr Asp Lys Asp Arg Trp Leu Ser Thr Gln Trp Arg
    450                 455                 460

Leu Val Ser Asp Glu Ala Val Thr Asn Gly Leu Arg Asp Gly Ile Val
465                 470                 475                 480

Phe Val Leu Lys Cys Leu Asp Phe Ser Leu Val Val Asn Val Lys Lys
                485                 490                 495

Ile Pro Phe Ile Ile Leu Ser Glu Glu Phe Ile Asp Pro Lys Ser His
            500                 505                 510

Lys Phe Val Leu Arg Leu Gln Ser Glu Thr Ser Val
        515                 520


<210> SEQ ID NO 5
<211> LENGTH: 521
<212> TYPE: PRT
<213> ORGANISM: Homo sapiens

<400> SEQUENCE: 5

Met Asp Thr Glu Ser Gln Tyr Ser Gly Tyr Ser Tyr Lys Ser Gly His
1               5                   10                  15

Ser Arg Ser Ser Arg Lys His Arg Asp Arg Arg Asp Arg His Arg Ser
            20                  25                  30

Lys Ser Arg Asp Gly Gly Arg Gly Asp Lys Ser Val Thr Ile Gln Ala
        35                  40                  45

Pro Gly Glu Pro Leu Leu Asp Asn Glu Ser Thr Arg Gly Asp Glu Arg
    50                  55                  60

Asp Asp Asn Trp Gly Glu Thr Thr Thr Val Val Thr Gly Thr Ser Glu
65                  70                  75                  80

His Ser Ile Ser His Asp Asp Leu Thr Arg Ile Ala Lys Asp Met Glu
                85                  90                  95

Asp Ser Val Pro Leu Asp Cys Ser Arg His Leu Gly Val Ala Ala Gly
            100                 105                 110

Ala Thr Leu Ala Leu Leu Ser Phe Leu Thr Pro Leu Ala Phe Leu Leu
        115                 120                 125

Leu Pro Pro Leu Leu Trp Arg Glu Glu Leu Glu Pro Cys Gly Thr Ala
    130                 135                 140

Cys Glu Gly Leu Phe Ile Ser Val Ala Phe Lys Leu Leu Ile Leu Leu
145                 150                 155                 160
```

-continued

Leu Gly Ser Trp Ala Leu Phe Phe Arg Arg Pro Lys Ala Ser Leu Pro
165 170 175

Arg Val Phe Val Leu Arg Ala Leu Leu Met Val Leu Val Phe Leu Leu
180 185 190

Val Val Ser Tyr Trp Leu Phe Tyr Gly Val Arg Ile Leu Asp Ala Arg
195 200 205

Glu Arg Ser Tyr Gln Gly Val Val Gln Phe Ala Val Ser Leu Val Asp
210 215 220

Ala Leu Leu Phe Val His Tyr Leu Ala Val Val Leu Leu Glu Leu Arg
225 230 235 240

Gln Leu Gln Pro Gln Phe Thr Leu Lys Val Val Arg Ser Thr Asp Gly
245 250 255

Ala Ser Arg Phe Tyr Asn Val Gly His Leu Ser Ile Gln Arg Val Ala
260 265 270

Val Trp Ile Leu Glu Lys Tyr Tyr His Asp Phe Pro Val Tyr Asn Pro
275 280 285

Ala Leu Leu Asn Leu Pro Lys Ser Val Leu Ala Lys Lys Val Ser Gly
290 295 300

Phe Lys Val Tyr Ser Leu Gly Glu Glu Asn Ser Thr Asn Asn Ser Thr
305 310 315 320

Gly Gln Ser Arg Ala Val Ile Ala Ala Ala Ala Arg Arg Arg Asp Asn
325 330 335

Ser His Asn Glu Tyr Tyr Tyr Glu Glu Ala Glu His Glu Arg Arg Val
340 345 350

Arg Lys Arg Arg Ala Arg Leu Val Val Ala Val Glu Glu Ala Phe Thr
355 360 365

His Ile Lys Arg Leu Gln Glu Glu Glu Gln Lys Asn Pro Arg Glu Val
370 375 380

Met Asp Pro Arg Glu Ala Ala Gln Ala Ile Phe Ala Ser Met Ala Arg
385 390 395 400

Ala Met Gln Lys Tyr Leu Arg Thr Thr Lys Gln Gln Pro Tyr His Thr
405 410 415

Met Glu Ser Ile Leu Gln His Leu Glu Phe Cys Ile Thr His Asp Met
420 425 430

Thr Pro Lys Ala Phe Leu Glu Arg Tyr Leu Ala Ala Gly Pro Thr Ile
435 440 445

Gln Tyr His Lys Glu Arg Trp Leu Ala Lys Gln Trp Thr Leu Val Ser
450 455 460

Glu Glu Pro Val Thr Asn Gly Leu Lys Asp Gly Ile Val Phe Leu Leu
465 470 475 480

Lys Arg Gln Asp Phe Ser Leu Val Val Ser Thr Lys Lys Val Pro Phe
485 490 495

Phe Lys Leu Ser Glu Glu Phe Val Asp Pro Lys Ser His Lys Phe Val
500 505 510

Met Arg Leu Gln Ser Glu Thr Ser Val
515 520

<210> SEQ ID NO 6
<211> LENGTH: 1064
<212> TYPE: PRT
<213> ORGANISM: Homo sapiens

<400> SEQUENCE: 6

Met Met Lys Phe Arg Phe Arg Arg Gln Gly Ala Asp Pro Gln Arg Glu
1 5 10 15

```
Lys Leu Lys Gln Glu Leu Phe Ala Phe Asn Lys Thr Val Glu His Gly
            20                  25                  30

Phe Pro Asn Gln Pro Ser Ala Leu Ala Phe Asp Pro Glu Leu Arg Ile
        35                  40                  45

Met Ala Ile Gly Thr Arg Ser Gly Ala Val Lys Ile Tyr Gly Ala Pro
    50                  55                  60

Gly Val Glu Phe Thr Gly Leu His Arg Asp Ala Ala Thr Val Thr Gln
65                  70                  75                  80

Met His Phe Leu Thr Gly Gln Gly Arg Leu Leu Ser Leu Leu Asp Asp
                85                  90                  95

Ser Ser Leu His Leu Trp Glu Ile Val His His Asn Gly Cys Ala His
            100                 105                 110

Leu Glu Glu Ala Leu Ser Phe Gln Leu Pro Ser Arg Pro Gly Phe Asp
        115                 120                 125

Gly Ala Ser Ala Pro Leu Ser Leu Thr Arg Val Thr Val Val Leu Leu
    130                 135                 140

Val Ala Ala Ser Asp Ile Ala Ala Leu Gly Thr Glu Gly Ser Ser Val
145                 150                 155                 160

Phe Phe Leu Asp Val Thr Thr Leu Thr Leu Leu Glu Gly Gln Thr Leu
                165                 170                 175

Ala Pro Gly Glu Val Leu Arg Ser Val Pro Asp Asp Tyr Arg Cys Gly
            180                 185                 190

Lys Ala Leu Gly Pro Val Glu Ser Leu Gln Gly His Leu Arg Asp Pro
        195                 200                 205

Thr Lys Ile Leu Ile Gly Tyr Ser Arg Gly Leu Leu Val Ile Trp Asn
    210                 215                 220

Gln Ala Ser Gln Cys Val Asp His Ile Phe Leu Gly Asn Gln Gln Leu
225                 230                 235                 240

Glu Ser Leu Cys Trp Gly Arg Asp Ser Ser Thr Val Val Ser Ser His
                245                 250                 255

Ser Asp Gly Ser Tyr Ala Val Trp Ser Val Asp Ala Gly Ser Phe Pro
            260                 265                 270

Thr Leu Gln Pro Thr Val Ala Thr Thr Pro Tyr Gly Pro Phe Pro Cys
        275                 280                 285

Lys Ala Ile Asn Lys Ile Leu Trp Arg Asn Cys Glu Ser Gly Gly His
    290                 295                 300

Phe Ile Ile Phe Ser Gly Gly Met Pro Arg Ala Ser Tyr Gly Asp Arg
305                 310                 315                 320

His Cys Val Ser Val Leu Arg Ala Glu Thr Leu Val Thr Leu Asp Phe
                325                 330                 335

Thr Ser Arg Ile Ile Asp Phe Phe Thr Val His Ser Thr Arg Pro Glu
            340                 345                 350

Asp Glu Phe Asp Asp Pro Gln Ala Leu Ala Val Leu Leu Glu Glu Glu
        355                 360                 365

Leu Val Val Leu Asp Leu Gln Thr Pro Gly Trp Pro Ala Val Pro Ala
    370                 375                 380

Pro Tyr Leu Ala Pro Leu His Ser Ser Ala Ile Thr Cys Ser Ala His
385                 390                 395                 400

Val Ala Ser Val Pro Ala Lys Leu Trp Ala Arg Ile Val Ser Ala Gly
                405                 410                 415

Glu Gln Gln Ser Pro Gln Pro Val Ser Ser Ala Leu Ser Trp Pro Ile
            420                 425                 430
```

-continued

```
Thr Gly Gly Arg Asn Leu Ala Gln Glu Pro Ser Gln Arg Gly Leu Leu
        435                 440                 445

Leu Thr Gly His Glu Asp Gly Thr Val Arg Phe Trp Asp Ala Ser Gly
    450                 455                 460

Val Ala Leu Arg Pro Leu Tyr Lys Leu Ser Thr Ala Gly Leu Phe Gln
465                 470                 475                 480

Thr Asp Cys Glu His Ala Asp Ser Leu Ala Gln Ala Ala Glu Asp Asp
                485                 490                 495

Trp Pro Pro Phe Arg Lys Val Gly Cys Phe Asp Pro Tyr Ser Asp Asp
            500                 505                 510

Pro Arg Leu Gly Val Gln Lys Val Ala Leu Cys Lys Tyr Thr Ala Gln
        515                 520                 525

Met Val Val Ala Gly Thr Ala Gly Gln Val Leu Val Leu Glu Leu Ser
    530                 535                 540

Asp Val Pro Val Glu Gln Ala Val Ser Val Ala Ile Ile Asp Leu Leu
545                 550                 555                 560

Gln Asp Arg Glu Gly Phe Thr Trp Lys Gly His Glu Arg Leu Ser Pro
                565                 570                 575

Arg Thr Gly Pro Leu Pro Trp Pro Ala Gly Phe Gln Pro Arg Val Leu
            580                 585                 590

Val Gln Cys Leu Pro Pro Ala Ala Val Thr Ala Val Thr Leu His Thr
        595                 600                 605

Glu Trp Ser Leu Val Ala Phe Gly Thr Ser His Gly Phe Gly Leu Phe
    610                 615                 620

Asp Tyr Gln Arg Lys Ser Pro Val Leu Ala Arg Cys Thr Leu His Pro
625                 630                 635                 640

Asn Asp Ser Leu Ala Met Glu Gly Pro Leu Ser Arg Val Lys Ser Leu
                645                 650                 655

Lys Lys Ser Leu Arg Gln Ser Phe Arg Arg Ile Arg Lys Ser Arg Val
            660                 665                 670

Ser Gly Lys Lys Arg Ala Ala Asn Ala Ser Ser Lys Leu Gln Glu Ala
        675                 680                 685

Asn Ala Gln Leu Ala Glu Gln Ala Cys Pro His Asp Val Glu Met Thr
    690                 695                 700

Pro Val Gln Arg Arg Ile Glu Pro Arg Ser Ala Asp Asp Ser Leu Ser
705                 710                 715                 720

Gly Val Val Arg Cys Leu Tyr Phe Ala Asp Thr Phe Leu Arg Asp Gly
                725                 730                 735

Ala His His Gly Pro Thr Met Trp Ala Gly Thr Asn Ser Gly Ser Val
            740                 745                 750

Phe Ala Tyr Ala Leu Glu Val Pro Ala Ala Ala Val Gly Gly Glu Lys
        755                 760                 765

Arg Pro Glu Gln Ala Val Glu Ala Val Leu Gly Lys Glu Val Gln Leu
    770                 775                 780

Met His Arg Ala Pro Val Val Ala Ile Ala Val Leu Asp Gly Arg Gly
785                 790                 795                 800

Arg Pro Leu Pro Glu Pro Tyr Glu Ala Ser Arg Asp Leu Ala Gln Ala
                805                 810                 815

Pro Asp Met Gln Gly Gly His Ala Val Leu Ile Ala Ser Glu Glu Gln
            820                 825                 830

Phe Lys Val Phe Thr Leu Pro Lys Val Ser Ala Lys Thr Lys Phe Lys
        835                 840                 845

Leu Thr Ala His Glu Gly Cys Arg Val Arg Lys Val Ala Leu Ala Thr
```

-continued

```
    850                 855                 860

Phe Ala Ser Val Ala Cys Glu Asp Tyr Ala Glu Thr Cys Leu Ala Cys
865                 870                 875                 880

Leu Thr Asn Leu Gly Asp Val His Val Phe Ser Val Pro Gly Leu Arg
                885                 890                 895

Pro Gln Val His Tyr Ser Cys Ile Arg Lys Glu Asp Ile Ser Gly Ile
            900                 905                 910

Ala Ser Cys Val Phe Thr Arg His Gly Gln Gly Phe Tyr Leu Ile Ser
        915                 920                 925

Pro Ser Glu Phe Glu Arg Phe Ser Leu Ser Ala Arg Asn Ile Thr Glu
    930                 935                 940

Pro Leu Cys Ser Leu Asp Ile Asn Trp Pro Arg Asp Ala Thr Gln Ala
945                 950                 955                 960

Ser Tyr Arg Ile Arg Glu Ser Pro Lys Leu Ser Gln Ala Asn Gly Thr
                965                 970                 975

Pro Ser Ile Leu Leu Ala Pro Gln Ser Leu Asp Gly Ser Pro Asp Pro
            980                 985                 990

Ala His Ser Met Gly Pro Asp Thr  Pro Glu Pro Pro Glu  Ala Ala Leu
        995                 1000                1005

Ser Pro  Met Ser Ile Asp Ser  Ala Thr Ser Ala Asp  Thr Thr Leu
    1010                1015                1020

Asp Thr  Thr Gly Asp Val Thr  Val Glu Asp Val Lys  Asp Phe Leu
    1025                1030                1035

Gly Ser  Ser Glu Glu Ser Glu  Lys Asn Leu Arg Asn  Leu Ala Glu
    1040                1045                1050

Asp Glu  Ala His Ala Cys Ala  Ile Leu Ile Lys
    1055                1060


<210> SEQ ID NO 7
<211> LENGTH: 904
<212> TYPE: PRT
<213> ORGANISM: Homo sapiens

<400> SEQUENCE: 7

Met Pro Val Arg Lys Gln Asp Thr Gln Arg Ala Leu His Leu Leu Glu
1               5                   10                  15

Glu Tyr Arg Ser Lys Leu Ser Gln Thr Glu Asp Arg Gln Leu Arg Ser
            20                  25                  30

Ser Ile Glu Arg Val Ile Asn Ile Phe Gln Ser Asn Leu Phe Gln Ala
        35                  40                  45

Leu Ile Asp Ile Gln Glu Phe Tyr Glu Val Thr Leu Leu Asp Asn Pro
    50                  55                  60

Lys Cys Ile Asp Arg Ser Lys Pro Ser Glu Pro Ile Gln Pro Val Asn
65                  70                  75                  80

Thr Trp Glu Ile Ser Ser Leu Pro Ser Ser Thr Val Thr Ser Glu Thr
                85                  90                  95

Leu Pro Ser Ser Leu Ser Pro Ser Val Glu Lys Tyr Arg Tyr Gln Asp
            100                 105                 110

Glu Asp Thr Pro Pro Gln Glu His Ile Ser Pro Gln Ile Thr Asn Glu
        115                 120                 125

Val Ile Gly Pro Glu Leu Val His Val Ser Glu Lys Asn Leu Ser Glu
    130                 135                 140

Ile Glu Asn Val His Gly Phe Val Ser His Ser His Ile Ser Pro Ile
145                 150                 155                 160
```

-continued

```
Lys Pro Thr Glu Ala Val Leu Pro Ser Pro Pro Thr Val Pro Val Ile
                165                 170                 175

Pro Val Leu Pro Val Pro Ala Glu Asn Thr Val Ile Leu Pro Thr Ile
            180                 185                 190

Pro Gln Ala Asn Pro Pro Pro Val Leu Val Asn Thr Asp Ser Leu Glu
        195                 200                 205

Thr Pro Thr Tyr Val Asn Gly Thr Asp Ala Asp Tyr Glu Tyr Glu Glu
    210                 215                 220

Ile Thr Leu Glu Arg Gly Asn Ser Gly Leu Gly Phe Ser Ile Ala Gly
225                 230                 235                 240

Gly Thr Asp Asn Pro His Ile Gly Asp Asp Ser Ser Ile Phe Ile Thr
                245                 250                 255

Lys Ile Ile Thr Gly Gly Ala Ala Ala Gln Asp Gly Arg Leu Arg Val
            260                 265                 270

Asn Asp Cys Ile Leu Arg Val Asn Glu Val Asp Val Arg Asp Val Thr
        275                 280                 285

His Ser Lys Ala Val Glu Ala Leu Lys Glu Ala Gly Ser Ile Val Arg
    290                 295                 300

Leu Tyr Val Lys Arg Arg Lys Pro Val Ser Glu Lys Ile Met Glu Ile
305                 310                 315                 320

Lys Leu Ile Lys Gly Pro Lys Gly Leu Gly Phe Ser Ile Ala Gly Gly
                325                 330                 335

Val Gly Asn Gln His Ile Pro Gly Asp Asn Ser Ile Tyr Val Thr Lys
            340                 345                 350

Ile Ile Glu Gly Gly Ala Ala His Lys Asp Gly Lys Leu Gln Ile Gly
        355                 360                 365

Asp Lys Leu Leu Ala Val Asn Asn Val Cys Leu Glu Glu Val Thr His
    370                 375                 380

Glu Glu Ala Val Thr Ala Leu Lys Asn Thr Ser Asp Phe Val Tyr Leu
385                 390                 395                 400

Lys Val Ala Lys Pro Thr Ser Met Tyr Met Asn Asp Gly Tyr Ala Pro
                405                 410                 415

Pro Asp Ile Thr Asn Ser Ser Ser Gln Pro Val Asp Asn His Val Ser
            420                 425                 430

Pro Ser Ser Phe Leu Gly Gln Thr Pro Ala Ser Pro Ala Arg Tyr Ser
        435                 440                 445

Pro Val Ser Lys Ala Val Leu Gly Asp Asp Glu Ile Thr Arg Glu Pro
    450                 455                 460

Arg Lys Val Val Leu His Arg Gly Ser Thr Gly Leu Gly Phe Asn Ile
465                 470                 475                 480

Val Gly Gly Glu Asp Gly Glu Gly Ile Phe Ile Ser Phe Ile Leu Ala
                485                 490                 495

Gly Gly Pro Ala Asp Leu Ser Gly Glu Leu Arg Lys Gly Asp Arg Ile
            500                 505                 510

Ile Ser Val Asn Ser Val Asp Leu Arg Ala Ala Ser His Glu Gln Ala
        515                 520                 525

Ala Ala Ala Leu Lys Asn Ala Gly Gln Ala Val Thr Ile Val Ala Gln
    530                 535                 540

Tyr Arg Pro Glu Glu Tyr Ser Arg Phe Glu Ala Lys Ile His Asp Leu
545                 550                 555                 560

Arg Glu Gln Met Met Asn Ser Ser Ile Ser Ser Gly Ser Gly Ser Leu
                565                 570                 575

Arg Thr Ser Gln Lys Arg Ser Leu Tyr Val Arg Ala Leu Phe Asp Tyr
```

-continued

```
            580                 585                 590

Asp Lys Thr Lys Asp Ser Gly Leu Pro Ser Gln Gly Leu Asn Phe Lys
        595                 600                 605

Phe Gly Asp Ile Leu His Val Ile Asn Ala Ser Asp Asp Glu Trp Trp
    610                 615                 620

Gln Ala Arg Gln Val Thr Pro Asp Gly Glu Ser Asp Glu Val Gly Val
625                 630                 635                 640

Ile Pro Ser Lys Arg Arg Val Glu Lys Lys Glu Arg Ala Arg Leu Lys
                645                 650                 655

Thr Val Lys Phe Asn Ser Lys Thr Arg Asp Lys Gly Glu Ile Pro Asp
            660                 665                 670

Asp Met Gly Ser Lys Gly Leu Lys His Val Thr Ser Asn Ala Ser Asp
        675                 680                 685

Ser Glu Ser Ser Tyr Arg Gly Gln Glu Glu Tyr Val Leu Ser Tyr Glu
    690                 695                 700

Pro Val Asn Gln Gln Glu Val Asn Tyr Thr Arg Pro Val Ile Ile Leu
705                 710                 715                 720

Gly Pro Met Lys Asp Arg Ile Asn Asp Asp Leu Ile Ser Glu Phe Pro
                725                 730                 735

Asp Lys Phe Gly Ser Cys Val Pro His Thr Thr Arg Pro Lys Arg Asp
            740                 745                 750

Tyr Glu Val Asp Gly Arg Asp Tyr His Phe Val Thr Ser Arg Glu Gln
        755                 760                 765

Met Glu Lys Asp Ile Gln Glu His Lys Phe Ile Glu Ala Gly Gln Tyr
    770                 775                 780

Asn Asn His Leu Tyr Gly Thr Ser Val Gln Ser Val Arg Glu Val Ala
785                 790                 795                 800

Glu Lys Gly Lys His Cys Ile Leu Asp Val Ser Gly Asn Ala Ile Lys
                805                 810                 815

Arg Leu Gln Ile Ala Gln Leu Tyr Pro Ile Ser Ile Phe Ile Lys Pro
            820                 825                 830

Lys Ser Met Glu Asn Ile Met Glu Met Asn Lys Arg Leu Thr Glu Glu
        835                 840                 845

Gln Ala Arg Lys Thr Phe Glu Arg Ala Met Lys Leu Glu Gln Glu Phe
    850                 855                 860

Thr Glu His Phe Thr Ala Ile Val Gln Gly Asp Thr Leu Glu Asp Ile
865                 870                 875                 880

Tyr Asn Gln Val Lys Gln Ile Ile Glu Glu Gln Ser Gly Ser Tyr Ile
                885                 890                 895

Trp Val Pro Ala Lys Glu Lys Leu
            900


<210> SEQ ID NO 8
<211> LENGTH: 817
<212> TYPE: PRT
<213> ORGANISM: Homo sapiens

<400> SEQUENCE: 8

Met His Lys His Gln His Cys Cys Lys Cys Pro Glu Cys Tyr Glu Val
1               5                   10                  15

Thr Arg Leu Ala Ala Leu Arg Arg Leu Glu Pro Pro Gly Tyr Gly Asp
            20                  25                  30

Trp Gln Val Pro Asp Pro Tyr Gly Pro Gly Gly Gly Asn Gly Ala Ser
        35                  40                  45
```

-continued

```
Ala Gly Tyr Gly Gly Tyr Ser Ser Gln Thr Leu Pro Ser Gln Ala Gly
    50                  55                  60

Ala Thr Pro Thr Pro Arg Thr Lys Ala Lys Leu Ile Pro Thr Gly Arg
65                  70                  75                  80

Asp Val Gly Pro Val Pro Pro Lys Pro Val Pro Gly Lys Ser Thr Pro
                85                  90                  95

Lys Leu Asn Gly Ser Gly Pro Ser Trp Trp Pro Glu Cys Thr Cys Thr
            100                 105                 110

Asn Arg Asp Trp Tyr Glu Gln Val Asn Gly Ser Asp Gly Met Phe Lys
        115                 120                 125

Tyr Glu Glu Ile Val Leu Glu Arg Gly Asn Ser Gly Leu Gly Phe Ser
    130                 135                 140

Ile Ala Gly Gly Ile Asp Asn Pro His Val Pro Asp Asp Pro Gly Ile
145                 150                 155                 160

Phe Ile Thr Lys Ile Ile Pro Gly Gly Ala Ala Ala Met Asp Gly Arg
                165                 170                 175

Leu Gly Val Asn Asp Cys Val Leu Arg Val Asn Glu Val Asp Val Ser
            180                 185                 190

Glu Val Val His Ser Arg Ala Val Glu Ala Leu Lys Glu Ala Gly Pro
        195                 200                 205

Val Val Arg Leu Val Val Arg Arg Arg Gln Pro Pro Pro Glu Thr Ile
    210                 215                 220

Met Glu Val Asn Leu Leu Lys Gly Pro Lys Gly Leu Gly Phe Ser Ile
225                 230                 235                 240

Ala Gly Gly Ile Gly Asn Gln His Ile Pro Gly Asp Asn Ser Ile Tyr
                245                 250                 255

Ile Thr Lys Ile Ile Glu Gly Gly Ala Ala Gln Lys Asp Gly Arg Leu
            260                 265                 270

Gln Ile Gly Asp Arg Leu Leu Ala Val Asn Asn Thr Asn Leu Gln Asp
        275                 280                 285

Val Arg His Glu Glu Ala Val Ala Ser Leu Lys Asn Thr Ser Asp Met
    290                 295                 300

Val Tyr Leu Lys Val Ala Lys Pro Gly Ser Leu His Leu Asn Asp Met
305                 310                 315                 320

Tyr Ala Pro Pro Asp Tyr Ala Ser Thr Phe Thr Ala Leu Ala Asp Asn
                325                 330                 335

His Ile Ser His Asn Ser Ser Leu Gly Tyr Leu Gly Ala Val Glu Ser
            340                 345                 350

Lys Val Ser Tyr Pro Ala Pro Pro Gln Val Pro Pro Thr Arg Tyr Ser
        355                 360                 365

Pro Ile Pro Arg His Met Leu Ala Glu Glu Asp Phe Thr Arg Glu Pro
    370                 375                 380

Arg Lys Ile Ile Leu His Lys Gly Ser Thr Gly Leu Gly Phe Asn Ile
385                 390                 395                 400

Val Gly Gly Glu Asp Gly Glu Gly Ile Phe Val Ser Phe Ile Leu Ala
                405                 410                 415

Gly Gly Pro Ala Asp Leu Ser Gly Glu Leu Arg Arg Gly Asp Arg Ile
            420                 425                 430

Leu Ser Val Asn Gly Val Asn Leu Arg Asn Ala Thr His Glu Gln Ala
        435                 440                 445

Ala Ala Ala Leu Lys Arg Ala Gly Gln Ser Val Thr Ile Val Ala Gln
    450                 455                 460

Tyr Arg Pro Glu Glu Tyr Ser Arg Phe Glu Ser Lys Ile His Asp Leu
```

-continued

```
465                 470                 475                 480

Arg Glu Gln Met Met Asn Ser Ser Met Ser Ser Gly Ser Gly Ser Leu
                485                 490                 495

Arg Thr Ser Glu Lys Arg Ser Leu Tyr Val Arg Ala Leu Phe Asp Tyr
            500                 505                 510

Asp Arg Thr Arg Asp Ser Cys Leu Pro Ser Gln Gly Leu Ser Phe Ser
        515                 520                 525

Tyr Gly Asp Ile Leu His Val Ile Asn Ala Ser Asp Asp Glu Trp Trp
    530                 535                 540

Gln Ala Arg Leu Val Thr Pro His Gly Glu Ser Glu Gln Ile Gly Val
545                 550                 555                 560

Ile Pro Ser Lys Lys Arg Val Glu Lys Lys Glu Arg Ala Arg Leu Lys
                565                 570                 575

Thr Val Lys Phe His Ala Arg Thr Gly Met Ile Glu Ser Asn Arg Asp
            580                 585                 590

Phe Pro Gly Leu Ser Asp Asp Tyr Tyr Gly Ala Lys Asn Leu Lys Gly
        595                 600                 605

Gln Glu Asp Ala Ile Leu Ser Tyr Glu Pro Val Thr Arg Gln Glu Ile
    610                 615                 620

His Tyr Ala Arg Pro Val Ile Ile Leu Gly Pro Met Lys Asp Arg Val
625                 630                 635                 640

Asn Asp Asp Leu Ile Ser Glu Phe Pro His Lys Phe Gly Ser Cys Val
                645                 650                 655

Pro His Thr Thr Arg Pro Arg Arg Asp Asn Glu Val Asp Gly Gln Asp
            660                 665                 670

Tyr His Phe Val Val Ser Arg Glu Gln Met Glu Lys Asp Ile Gln Asp
        675                 680                 685

Asn Lys Phe Ile Glu Ala Gly Gln Phe Asn Asp Asn Leu Tyr Gly Thr
    690                 695                 700

Ser Ile Gln Ser Val Arg Ala Val Ala Glu Arg Gly Lys His Cys Ile
705                 710                 715                 720

Leu Asp Val Ser Gly Asn Ala Ile Lys Arg Leu Gln Gln Ala Gln Leu
                725                 730                 735

Tyr Pro Ile Ala Ile Phe Ile Lys Pro Lys Ser Ile Glu Ala Leu Met
            740                 745                 750

Glu Met Asn Arg Arg Gln Thr Tyr Glu Gln Ala Asn Lys Ile Tyr Asp
        755                 760                 765

Lys Ala Met Lys Leu Glu Gln Glu Phe Gly Glu Tyr Phe Thr Ala Ile
    770                 775                 780

Val Gln Gly Asp Ser Leu Glu Glu Ile Tyr Asn Lys Ile Lys Gln Ile
785                 790                 795                 800

Ile Glu Asp Gln Ser Gly His Tyr Ile Trp Val Pro Ser Pro Glu Lys
                805                 810                 815

Leu


<210> SEQ ID NO 9
<211> LENGTH: 721
<212> TYPE: PRT
<213> ORGANISM: Homo sapiens

<400> SEQUENCE: 9

Met Asp Cys Leu Cys Ile Val Thr Thr Lys Lys Tyr Arg Tyr Gln Asp
1               5                   10                  15

Glu Asp Thr Pro Pro Leu Glu His Ser Pro Ala His Leu Pro Asn Gln
```

-continued

```
            20                  25                  30

Ala Asn Ser Pro Pro Val Ile Val Asn Thr Asp Thr Leu Glu Ala Pro
        35                  40                  45

Gly Tyr Val Asn Gly Thr Glu Gly Glu Met Glu Tyr Glu Glu Ile Thr
    50                  55                  60

Leu Glu Arg Gly Asn Ser Gly Leu Gly Phe Ser Ile Ala Gly Gly Thr
65                  70                  75                  80

Asp Asn Pro His Ile Gly Asp Asp Pro Ser Ile Phe Ile Thr Lys Ile
                85                  90                  95

Ile Pro Gly Gly Ala Ala Ala Gln Asp Gly Arg Leu Arg Val Asn Asp
            100                 105                 110

Ser Ile Leu Phe Val Asn Glu Val Asp Val Arg Glu Val Thr His Ser
        115                 120                 125

Ala Ala Val Glu Ala Leu Lys Glu Ala Gly Ser Ile Val Arg Leu Tyr
    130                 135                 140

Val Met Arg Arg Lys Pro Pro Ala Glu Lys Val Met Glu Ile Lys Leu
145                 150                 155                 160

Ile Lys Gly Pro Lys Gly Leu Gly Phe Ser Ile Ala Gly Gly Val Gly
                165                 170                 175

Asn Gln His Ile Pro Gly Asp Asn Ser Ile Tyr Val Thr Lys Ile Ile
            180                 185                 190

Glu Gly Gly Ala Ala His Lys Asp Gly Arg Leu Gln Ile Gly Asp Lys
        195                 200                 205

Ile Leu Ala Val Asn Ser Val Gly Leu Glu Asp Val Met His Glu Asp
    210                 215                 220

Ala Val Ala Ala Leu Lys Asn Thr Tyr Asp Val Val Tyr Leu Lys Val
225                 230                 235                 240

Ala Lys Pro Ser Asn Ala Tyr Leu Ser Asp Ser Tyr Ala Pro Pro Asp
                245                 250                 255

Ile Thr Thr Ser Tyr Ser Gln His Leu Asp Asn Glu Ile Ser His Ser
            260                 265                 270

Ser Tyr Leu Gly Thr Asp Tyr Pro Thr Ala Met Thr Pro Thr Ser Pro
        275                 280                 285

Arg Arg Tyr Ser Pro Val Ala Lys Asp Leu Leu Gly Glu Glu Asp Ile
    290                 295                 300

Pro Arg Glu Pro Arg Arg Ile Val Ile His Arg Gly Ser Thr Gly Leu
305                 310                 315                 320

Gly Phe Asn Ile Val Gly Gly Glu Asp Gly Glu Gly Ile Phe Ile Ser
                325                 330                 335

Phe Ile Leu Ala Gly Gly Pro Ala Asp Leu Ser Gly Glu Leu Arg Lys
            340                 345                 350

Gly Asp Gln Ile Leu Ser Val Asn Gly Val Asp Leu Arg Asn Ala Ser
        355                 360                 365

His Glu Gln Ala Ala Ile Ala Leu Lys Asn Ala Gly Gln Thr Val Thr
    370                 375                 380

Ile Ile Ala Gln Tyr Lys Pro Glu Glu Tyr Ser Arg Phe Glu Ala Lys
385                 390                 395                 400

Ile His Asp Leu Arg Glu Gln Leu Met Asn Ser Ser Leu Gly Ser Gly
                405                 410                 415

Thr Ala Ser Leu Arg Ser Asn Pro Lys Arg Gly Phe Tyr Ile Arg Ala
            420                 425                 430

Leu Phe Asp Tyr Asp Lys Thr Lys Asp Cys Gly Phe Leu Ser Gln Ala
        435                 440                 445
```

```
Leu Ser Phe Arg Phe Gly Asp Val Leu His Val Ile Asp Ala Ser Asp
    450                 455                 460

Glu Glu Trp Trp Gln Ala Arg Arg Val His Ser Asp Ser Glu Thr Asp
465                 470                 475                 480

Asp Ile Gly Phe Ile Pro Ser Lys Arg Arg Val Glu Arg Arg Glu Trp
                485                 490                 495

Ser Arg Leu Lys Ala Lys Asp Trp Gly Ser Ser Ser Gly Ser Gln Gly
            500                 505                 510

Arg Glu Asp Ser Val Leu Ser Tyr Glu Thr Val Thr Gln Met Glu Val
        515                 520                 525

His Tyr Ala Arg Pro Ile Ile Ile Leu Gly Pro Thr Lys Asp Arg Ala
    530                 535                 540

Asn Asp Asp Leu Leu Ser Glu Phe Pro Asp Lys Phe Gly Ser Cys Val
545                 550                 555                 560

Pro His Thr Thr Arg Pro Lys Arg Glu Tyr Glu Ile Asp Gly Arg Asp
                565                 570                 575

Tyr His Phe Val Ser Ser Arg Glu Lys Met Glu Lys Asp Ile Gln Ala
            580                 585                 590

His Lys Phe Ile Glu Ala Gly Gln Tyr Asn Ser His Leu Tyr Gly Thr
        595                 600                 605

Ser Val Gln Ser Val Arg Glu Val Ala Glu Gln Gly Lys His Cys Ile
    610                 615                 620

Leu Asp Val Ser Ala Asn Ala Val Arg Arg Leu Gln Ala Ala His Leu
625                 630                 635                 640

His Pro Ile Ala Ile Phe Ile Arg Pro Arg Ser Leu Glu Asn Val Leu
                645                 650                 655

Glu Ile Asn Lys Arg Ile Thr Glu Glu Gln Ala Arg Lys Ala Phe Asp
            660                 665                 670

Arg Ala Thr Lys Leu Glu Gln Glu Phe Thr Glu Cys Phe Ser Ala Ile
        675                 680                 685

Val Glu Gly Asp Ser Phe Glu Glu Ile Tyr His Lys Val Lys Arg Val
    690                 695                 700

Ile Glu Asp Leu Ser Gly Pro Tyr Ile Trp Val Pro Ala Arg Glu Arg
705                 710                 715                 720

Leu


<210> SEQ ID NO 10
<211> LENGTH: 975
<212> TYPE: PRT
<213> ORGANISM: Homo sapiens

<400> SEQUENCE: 10

Met Gly Ile Phe Lys Ser Ser Leu Phe Gln Ala Leu Leu Asp Ile Gln
1               5                   10                  15

Glu Phe Tyr Glu Val Thr Leu Leu Asn Ser Gln Lys Ser Cys Glu Gln
            20                  25                  30

Lys Ile Glu Glu Ala Asn Gln Val Leu Gln Lys Trp Glu Lys Thr Ser
        35                  40                  45

Leu Leu Ala Pro Cys His Asp Arg Leu Gln Lys Ser Ser Glu Leu Thr
    50                  55                  60

Asp Cys Ser Gly Ser Lys Glu Asn Ala Ser Cys Ile Glu Gln Asn Lys
65                  70                  75                  80

Glu Asn Gln Ser Phe Glu Asn Glu Thr Asp Glu Thr Thr Thr Gln Asn
                85                  90                  95
```

-continued

```
Gln Gly Arg Cys Pro Ala Gln Asn Cys Ser Val Glu Ala Pro Ala Trp
            100                 105                 110

Met Pro Val His His Cys Thr Lys Tyr Arg Tyr Gln Asp Glu Asp Ala
        115                 120                 125

Pro His Asp His Ser Leu Pro Arg Leu Thr His Glu Val Arg Gly Pro
    130                 135                 140

Glu Leu Val His Val Ser Glu Lys Asn Leu Ser Gln Ile Glu Asn Val
145                 150                 155                 160

His Gly Tyr Val Leu Gln Ser His Ile Ser Pro Leu Lys Ala Ser Pro
                165                 170                 175

Ala Pro Ile Ile Val Asn Thr Asp Thr Leu Asp Thr Ile Pro Tyr Val
            180                 185                 190

Asn Gly Thr Glu Ile Glu Tyr Glu Phe Glu Glu Ile Thr Leu Glu Arg
        195                 200                 205

Gly Asn Ser Gly Leu Gly Phe Ser Ile Ala Gly Gly Thr Asp Asn Pro
    210                 215                 220

His Ile Gly Asp Asp Pro Gly Ile Phe Ile Thr Lys Ile Ile Pro Gly
225                 230                 235                 240

Gly Ala Ala Ala Glu Asp Gly Arg Leu Arg Val Asn Asp Cys Ile Leu
                245                 250                 255

Arg Val Asn Glu Val Asp Val Ser Glu Val Ser His Ser Lys Ala Val
            260                 265                 270

Glu Ala Leu Lys Glu Ala Gly Ser Ile Val Arg Leu Tyr Val Arg Arg
        275                 280                 285

Arg Arg Pro Ile Leu Glu Thr Val Val Glu Ile Lys Leu Phe Lys Gly
    290                 295                 300

Pro Lys Gly Leu Gly Phe Ser Ile Ala Gly Gly Val Gly Asn Gln His
305                 310                 315                 320

Ile Pro Gly Asp Asn Ser Ile Tyr Val Thr Lys Ile Ile Asp Gly Gly
                325                 330                 335

Ala Ala Gln Lys Asp Gly Arg Leu Gln Val Gly Asp Arg Leu Leu Met
            340                 345                 350

Val Asn Asn Tyr Ser Leu Glu Glu Val Thr His Glu Glu Ala Val Ala
        355                 360                 365

Ile Leu Lys Asn Thr Ser Glu Val Val Tyr Leu Lys Val Gly Lys Pro
    370                 375                 380

Thr Thr Ile Tyr Met Thr Asp Pro Tyr Gly Pro Pro Asp Ile Thr His
385                 390                 395                 400

Ser Tyr Ser Pro Pro Met Glu Asn His Leu Leu Ser Gly Asn Asn Gly
                405                 410                 415

Thr Leu Glu Tyr Lys Thr Ser Leu Pro Pro Ile Ser Pro Gly Arg Tyr
            420                 425                 430

Ser Pro Ile Pro Lys His Met Leu Val Asp Asp Asp Tyr Thr Arg Pro
        435                 440                 445

Pro Glu Pro Val Tyr Ser Thr Val Asn Lys Leu Cys Asp Lys Pro Ala
    450                 455                 460

Ser Pro Arg His Tyr Ser Pro Val Glu Cys Asp Lys Ser Phe Leu Leu
465                 470                 475                 480

Ser Ala Pro Tyr Ser His Tyr His Leu Gly Leu Leu Pro Asp Ser Glu
                485                 490                 495

Met Thr Ser His Ser Gln His Ser Thr Ala Thr Arg Gln Pro Ser Met
            500                 505                 510
```

-continued

```
Thr Leu Gln Arg Ala Val Ser Leu Glu Gly Glu Pro Arg Lys Val Val
        515                 520                 525

Leu His Lys Gly Ser Thr Gly Leu Gly Phe Asn Ile Val Gly Gly Glu
    530                 535                 540

Asp Gly Glu Gly Ile Phe Val Ser Phe Ile Leu Ala Gly Gly Pro Ala
545                 550                 555                 560

Asp Leu Ser Gly Glu Leu Gln Arg Gly Asp Gln Ile Leu Ser Val Asn
                565                 570                 575

Gly Ile Asp Leu Arg Gly Ala Ser His Glu Gln Ala Ala Ala Ala Leu
            580                 585                 590

Lys Gly Ala Gly Gln Thr Val Thr Ile Ile Ala Gln Tyr Gln Pro Glu
        595                 600                 605

Asp Tyr Ala Arg Phe Glu Ala Lys Ile His Asp Leu Arg Glu Gln Met
    610                 615                 620

Met Asn His Ser Met Ser Ser Gly Ser Gly Ser Leu Arg Thr Asn Gln
625                 630                 635                 640

Lys Arg Ser Leu Tyr Val Arg Ala Met Phe Asp Tyr Asp Lys Ser Lys
                645                 650                 655

Asp Ser Gly Leu Pro Ser Gln Gly Leu Ser Phe Lys Tyr Gly Asp Ile
            660                 665                 670

Leu His Val Ile Asn Ala Ser Asp Asp Glu Trp Trp Gln Ala Arg Arg
        675                 680                 685

Val Met Leu Glu Gly Asp Ser Glu Glu Met Gly Val Ile Pro Ser Lys
    690                 695                 700

Arg Arg Val Glu Arg Lys Glu Arg Ala Arg Leu Lys Thr Val Lys Phe
705                 710                 715                 720

Asn Ala Lys Pro Gly Val Ile Asp Ser Lys Gly Ser Phe Asn Asp Lys
                725                 730                 735

Arg Lys Lys Ser Phe Ile Phe Ser Arg Lys Phe Pro Phe Tyr Lys Asn
            740                 745                 750

Lys Glu Gln Ser Glu Gln Glu Thr Ser Asp Pro Glu Arg Gly Gln Glu
        755                 760                 765

Asp Leu Ile Leu Ser Tyr Glu Pro Val Thr Arg Gln Glu Ile Asn Tyr
    770                 775                 780

Thr Arg Pro Val Ile Ile Leu Gly Pro Met Lys Asp Arg Ile Asn Asp
785                 790                 795                 800

Asp Leu Ile Ser Glu Phe Pro Asp Lys Phe Gly Ser Cys Val Pro His
                805                 810                 815

Thr Thr Arg Pro Lys Arg Asp Tyr Glu Val Asp Gly Arg Asp Tyr His
            820                 825                 830

Phe Val Ile Ser Arg Glu Gln Met Glu Lys Asp Ile Gln Glu His Lys
        835                 840                 845

Phe Ile Glu Ala Gly Gln Tyr Asn Asp Asn Leu Tyr Gly Thr Ser Val
    850                 855                 860

Gln Ser Val Arg Phe Val Ala Glu Arg Gly Lys His Cys Ile Leu Asp
865                 870                 875                 880

Val Ser Gly Asn Ala Ile Lys Arg Leu Gln Val Ala Gln Leu Tyr Pro
                885                 890                 895

Ile Ala Ile Phe Ile Lys Pro Arg Ser Leu Glu Pro Leu Met Glu Met
            900                 905                 910

Asn Lys Arg Leu Thr Glu Glu Gln Ala Lys Lys Thr Tyr Asp Arg Ala
        915                 920                 925

Ile Lys Leu Glu Gln Glu Phe Gly Glu Tyr Phe Thr Ala Ile Val Gln
```

-continued

```
    930                 935                 940

Gly Asp Thr Leu Glu Asp Ile Tyr Asn Gln Cys Lys Leu Val Ile Glu
945                 950                 955                 960

Glu Gln Ser Gly Pro Phe Ile Trp Ile Pro Ser Lys Glu Lys Leu
                965                 970                 975
```